(12) United States Patent
Nagase et al.

(10) Patent No.: US 7,494,499 B2
(45) Date of Patent: Feb. 24, 2009

(54) SURGICAL THERAPEUTIC INSTRUMENT

(75) Inventors: Toru Nagase, Tachikawa (JP); Katsumi Sasaki, Tokyo (JP)

(73) Assignee: Olympus Corporation, Tokyo (JP)

( * ) Notice: Subject to any disclaimer, the term of this patent is extended or adjusted under 35 U.S.C. 154(b) by 348 days.

(21) Appl. No.: 10/367,538

(22) Filed: Feb. 14, 2003

(65) Prior Publication Data

US 2003/0158576 A1  Aug. 21, 2003

(30) Foreign Application Priority Data

| Feb. 15, 2002 | (JP) | ............................. 2002-039132 |
| Feb. 15, 2002 | (JP) | ............................. 2002-039133 |
| Feb. 15, 2002 | (JP) | ............................. 2002-039134 |
| Mar. 29, 2002 | (JP) | ............................. 2002-097880 |

(51) Int. Cl.
*A61B 17/00* (2006.01)

(52) U.S. Cl. ...................................... 606/205

(58) Field of Classification Search ......... 606/205–211, 606/170, 174, 37, 39, 45, 46, 51, 52, 167, 606/190–193, 105, 90, 119, 120, 151; 600/201, 600/214–216; 700/245
See application file for complete search history.

(56) References Cited

U.S. PATENT DOCUMENTS

| 2,028,635 | A | * | 1/1936 | Wappler ....................... 606/46 |
| 5,275,608 | A | * | 1/1994 | Forman et al. ............... 606/170 |
| 5,314,445 | A | * | 5/1994 | Heidmueller nee Degwitz et al. ........................... 606/208 |
| 5,330,502 | A | * | 7/1994 | Hassler et al. ............... 606/205 |
| 5,350,391 | A | * | 9/1994 | Iacovelli ..................... 606/170 |
| 5,417,203 | A | * | 5/1995 | Tovey et al. ................. 600/106 |
| 5,454,827 | A | * | 10/1995 | Aust et al. ................... 606/170 |
| 5,468,250 | A | * | 11/1995 | Paraschac et al. ........... 606/205 |
| 5,607,450 | A | * | 3/1997 | Zvenyatsky et al. ......... 606/206 |
| 5,702,408 | A | * | 12/1997 | Wales et al. ................. 606/139 |
| 5,782,859 | A | * | 7/1998 | Nicholas et al. ............. 600/564 |
| 5,810,879 | A | * | 9/1998 | de Guillebon ............... 606/205 |
| 5,860,995 | A | * | 1/1999 | Berkelaar .................... 606/174 |
| 5,908,436 | A |   | 6/1999 | Cuschieri et al. |
| 6,063,098 | A | * | 5/2000 | Houser et al. ............... 606/169 |
| 6,093,155 | A | * | 7/2000 | Ouchi ......................... 600/569 |
| 6,193,737 | B1 | * | 2/2001 | Ouchi ......................... 606/174 |
| 6,213,957 | B1 | * | 4/2001 | Milliman et al. ............ 600/566 |
| 6,592,572 | B1 | * | 7/2003 | Suzuta .......................... 606/1 |
| 6,817,974 | B2 | * | 11/2004 | Cooper et al. ............... 600/142 |
| 6,936,061 | B2 | * | 8/2005 | Sasaki ......................... 606/205 |
| 2002/0156497 | A1 | * | 10/2002 | Nagase et al. ............... 606/205 |
| 2004/0193212 | A1 | * | 9/2004 | Taniguchi et al. ........... 606/205 |
| 2005/0075664 | A1 | * | 4/2005 | Nagase et al. ............... 606/205 |

* cited by examiner

*Primary Examiner*—Todd E Manahan
*Assistant Examiner*—Elizabeth Houston
(74) *Attorney, Agent, or Firm*—Scully, Scott, Murphy & Presser, P.C.

(57) ABSTRACT

The disclosed invention relates to an improvement in a surgical therapeutic instrument which includes an inserting part, a manipulating part, and a therapeutic part. In a link mechanism having a transmission shaft for transmitting a driving force applied to the manipulating part to the therapeutic part, the position of the transmission shaft is restricted, and a joint is provided in the transmission shaft to reduce the strain of the transmission shaft. A sheath is also provided in the inserting part to facilitate cleaning thereof. A mechanism is provided for immovably locking the movable portion. A circular arc centered about a turning shaft is introduced into the shape of the manipulating part to improve the manipulability thereof. Further, the structure of a gripping portion of the manipulating part is improved.

4 Claims, 42 Drawing Sheets

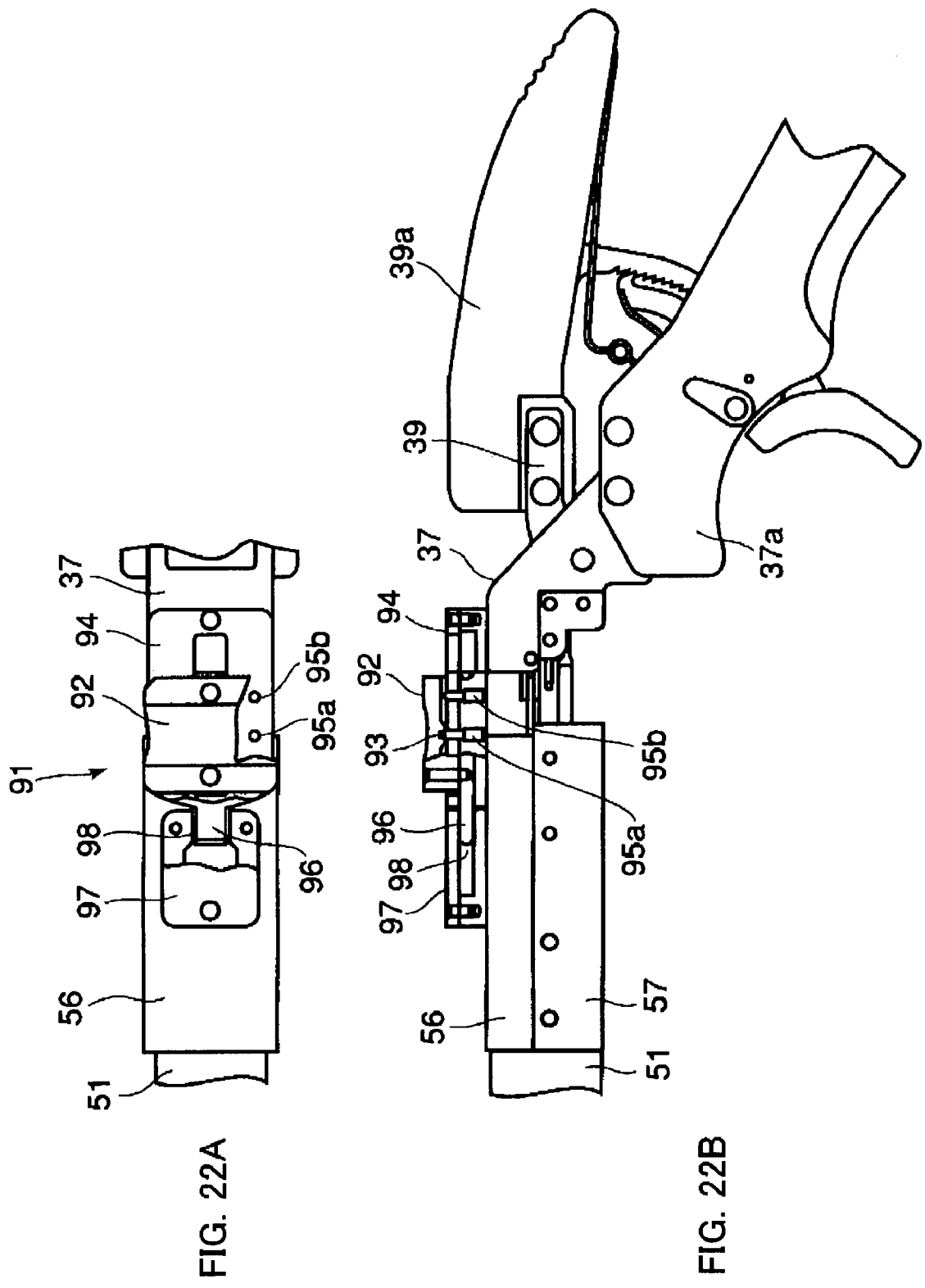

SURGICAL THERAPEUTIC INSTRUMENT

CROSS-REFERENCE TO RELATED APPLICATIONS

This application is based upon and claims the benefit of priority from prior Japanese Patent Application Nos. 2002-039132, filed Feb. 15, 2002, 2002-039133, filed Feb. 15, 2002, 2002-039134, filed Feb. 15, 2002, and 2002-097880, filed Feb. 29, 2002, the entire contents of the applications are incorporated herein by reference.

BACKGROUND OF THE INVENTION

1. Field of the Invention

The invention relates to a surgical therapeutic instrument which includes an inserting part to be inserted into a body, a manipulating part provided at a proximal end of the inserting part and constructed to be gripped by an operator, and a therapeutic part provided at a distal tip of the inserting part and constructed to be manipulated by the manipulating part.

2. Description of the Related Art

A surgical therapeutic instrument which includes an inserting part to be inserted into a body, a manipulating part provided at a proximal end of the inserting part and constructed to be gripped by an operator, and a therapeutic part provided at a distal tip of the inserting part and constructed to be manipulated by the manipulating part has been disclosed in several patent publications.

In the surgical therapeutic instrument disclosed in U.S. Pat. No. 5,314,445, its therapeutic part disposed at the distal tip of the surgical therapeutic instrument and its manipulating part are connected by a cable, and the therapeutic part is turned in one plane by a manipulation for turning the manipulating part in one plane, and the therapeutic part is opened and closed by manipulations for opening and closing the manipulating part.

In the surgical therapeutic instrument disclosed in U.S. Pat. No. 5,275,608, its therapeutic part can be manipulated to turn in one plane, and the therapeutic part can also be manipulated to open and close. A handle portion which constitutes a manipulating part and a tool portion that constitutes the therapeutic part are constructed to constantly maintain a mutually parallel state at an arbitrary turning position. Namely, it is possible to turn the therapeutic part by turning the handle portion.

In the surgical therapeutic instrument disclosed in U.S. Pat. No. 5,908,436, its therapeutic part can be turned by turning the grip of the manipulating part about two vertical and horizontal shafts which are perpendicular to each other and corresponds to a wrist position.

BRIEF SUMMARY OF THE INVENTION

The invention relates to an improvement in a surgical therapeutic instrument which includes an inserting part to be inserted into a body, a manipulating part provided at a proximal end of the inserting part and constructed to be gripped by an operator, and a therapeutic part provided at a distal tip of the inserting part and constructed to be manipulated by the manipulating part.

According to one feature of the invention, the surgical therapeutic instrument includes a mechanical link mechanism having at least one transmission shaft for transmitting to the therapeutic part a driving force for manipulation given from the manipulating part, the transmission shaft having a joint at an intermediate position. In addition, a position restricting member for restricting a position of the transmission shaft on a plane perpendicular to a longitudinal direction of the inserting part is provided in a predetermined portion of the transmission shaft.

Accordingly, the inserting part can be thinned by restricting the position of the transmission shaft, and the strain of the transmission shaft that accompanies the restriction of the position can be reduced by the motion of a joint portion.

According to another feature of the invention, the surgical therapeutic instrument includes a sheath for covering the inserting part, and during cleaning, the sheath is removed in the axial direction of the inserting part and the interior of the inserting part is cleaned. Accordingly, it is possible to easily clean the transmission shaft and the like in the interior of the inserting part.

According to another feature of the invention, the surgical therapeutic instrument includes a mechanism for locking a movable portion of the surgical therapeutic instrument. Accordingly, the manipulability of the surgical therapeutic instrument is improved.

According to another feature of the invention, in the surgical therapeutic instrument, a circular arc (or a similar shape) centered about a turning shaft disposed in the manipulating part is adopted as a portion of the external shape of the manipulating part. Accordingly, it is possible to reduce the amount of movement of each portion of a hand in the manipulating part during manipulation.

According to another feature of the invention, the surgical therapeutic instrument includes an improved gripping portion. For example, the turning shaft of the gripping portion and gripping surfaces thereof are made non-parallel, or an engagement structure between a concave portion and a convex portion is formed on the gripping surface. Accordingly, gripping becomes far easier.

BRIEF DESCRIPTION OF THE SEVERAL VIEWS OF THE DRAWINGS

These and other features, aspects, and advantages of the apparatus and methods of the present invention will become better understood with regard to the following description, appended claims, and accompanying drawings where:

FIG. 22A is a plan view of handle fixing portion of the manipulating part which is in a locked state;

FIG. 22B is a side view of the handle fixing portion shown in FIG. 22A;

DETAILED DESCRIPTION OF THE INVENTION

Preferred embodiments of the present invention will be described hereinafter with reference to the drawings.

A first embodiment of the invention will be described below with reference to FIGS. 1 to 23.

Figure 1:
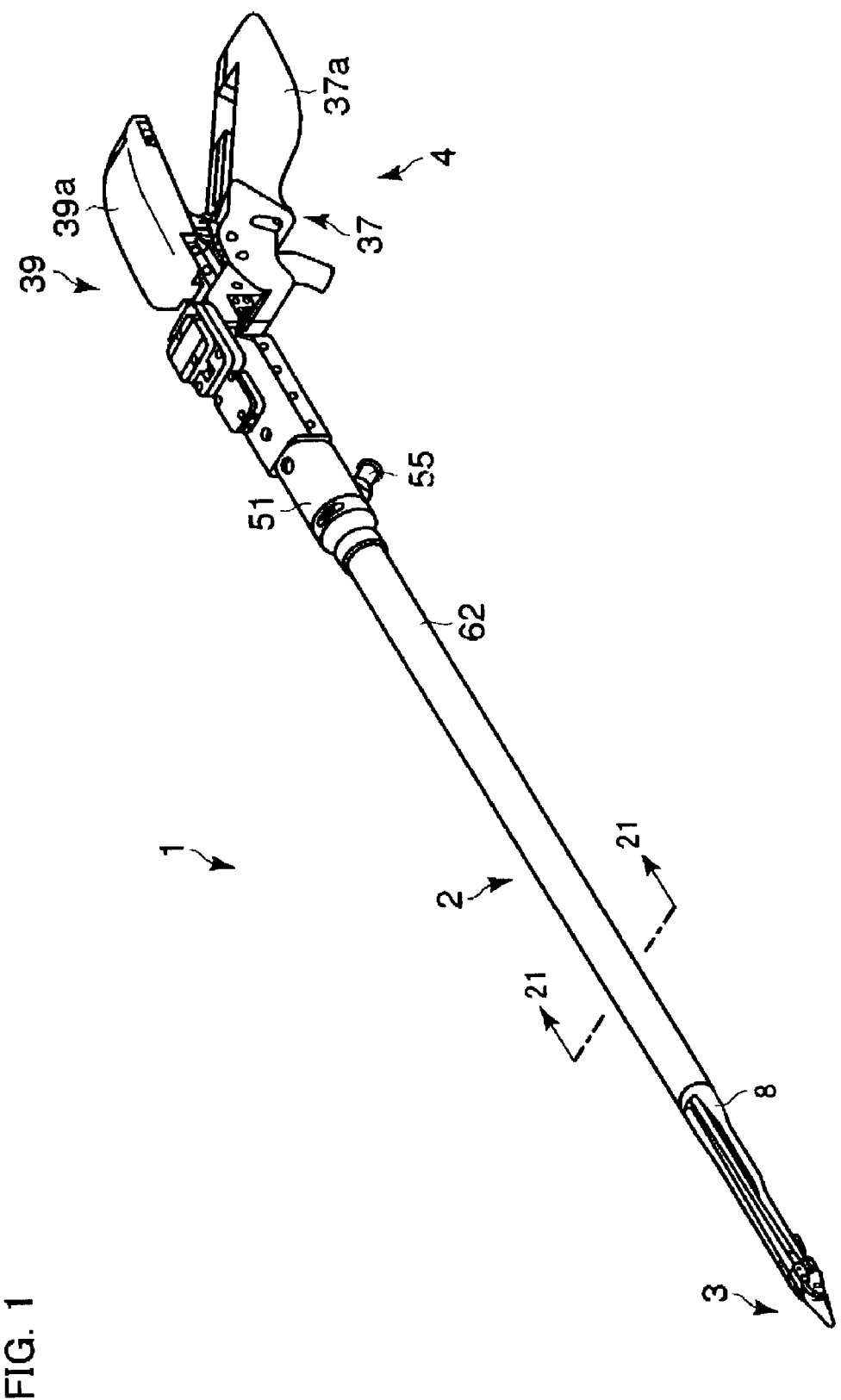
FIG. 1 is a perspective view showing the entire construction of a surgical therapeutic instrument according to a first embodiment of the invention.

FIG. 1 is a perspective view showing the entire construction of a surgical therapeutic instrument 1. As shown in FIG. 1, the surgical therapeutic instrument 1 includes an inserting part 2, a therapeutic part 3 provided at a distal tip portion of the inserting part 2, and a manipulating part 4 provided at a proximal end of the inserting part 2. A first supporting part 8 which protrudes distally and has rigidity is provided at the distal tip portion of the inserting part 2, and the portion of the inserting part 2 that extends proximally from the first supporting part 8 is covered with a sheath 62. A connecting portion 51 to which the sheath 62 is secured is provided on the proximal side of the inserting part 2. A cleaning port 55 through which water or the like is introduced for cleaning an interior of the inserting part 2, the connecting portion 51, or the like is provided on a side surface of the inserting part 2.

The manipulating part 4 has a first handle 37 fitted with a first grip 37a and a second handle 39 fitted with a second grip 39a.

Figure 21:
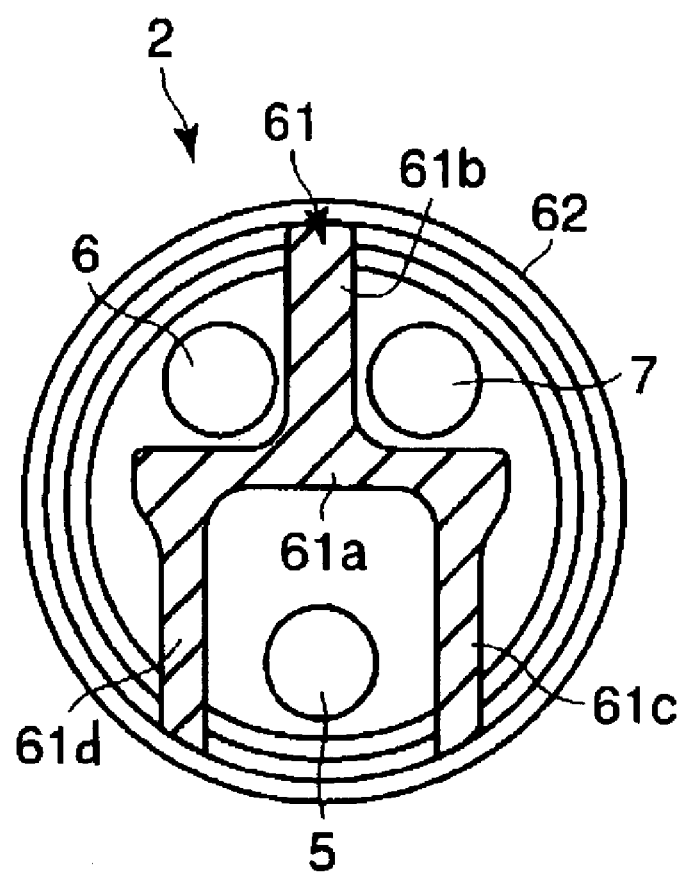
FIG. 21 is a cross-sectional view taken along line 21-21 of FIG. 1.

The inserting part 2 will be described below. FIG. 21 is a cross-sectional view taken along line 21-21 of FIG. 1. As shown in FIG. 21, a first driving rod 5, a second driving rod 6 and a third driving rod 7, each of which is a rod of small diameter, are inserted through the interior of the inserting part 2 in the state of being parallel or approximately parallel to one another. The first driving rod 5 is an element of an opening and closing link mechanism which opens and closes the therapeutic part 3, and the second driving rod 6 and the third driving rod 7 are elements of a turning link mechanism which turns the therapeutic part 3.

As is apparent from FIG. 21, the first driving rod 5 is arranged to be deviated to one side (in the first embodiment, the bottom side) of the inserting part 2 with respect to the longitudinal central axis thereof. The second driving rod 6 and the third driving rod 7 are arranged horizontally symmetrically on the opposite side to the first driving rod 5 (in the first embodiment, on the top side) with respect to the longitudinal central axis of the inserting part 2. Each of the driving rods 5, 6 and 7 is movable axially back and forth.

Figure 2:
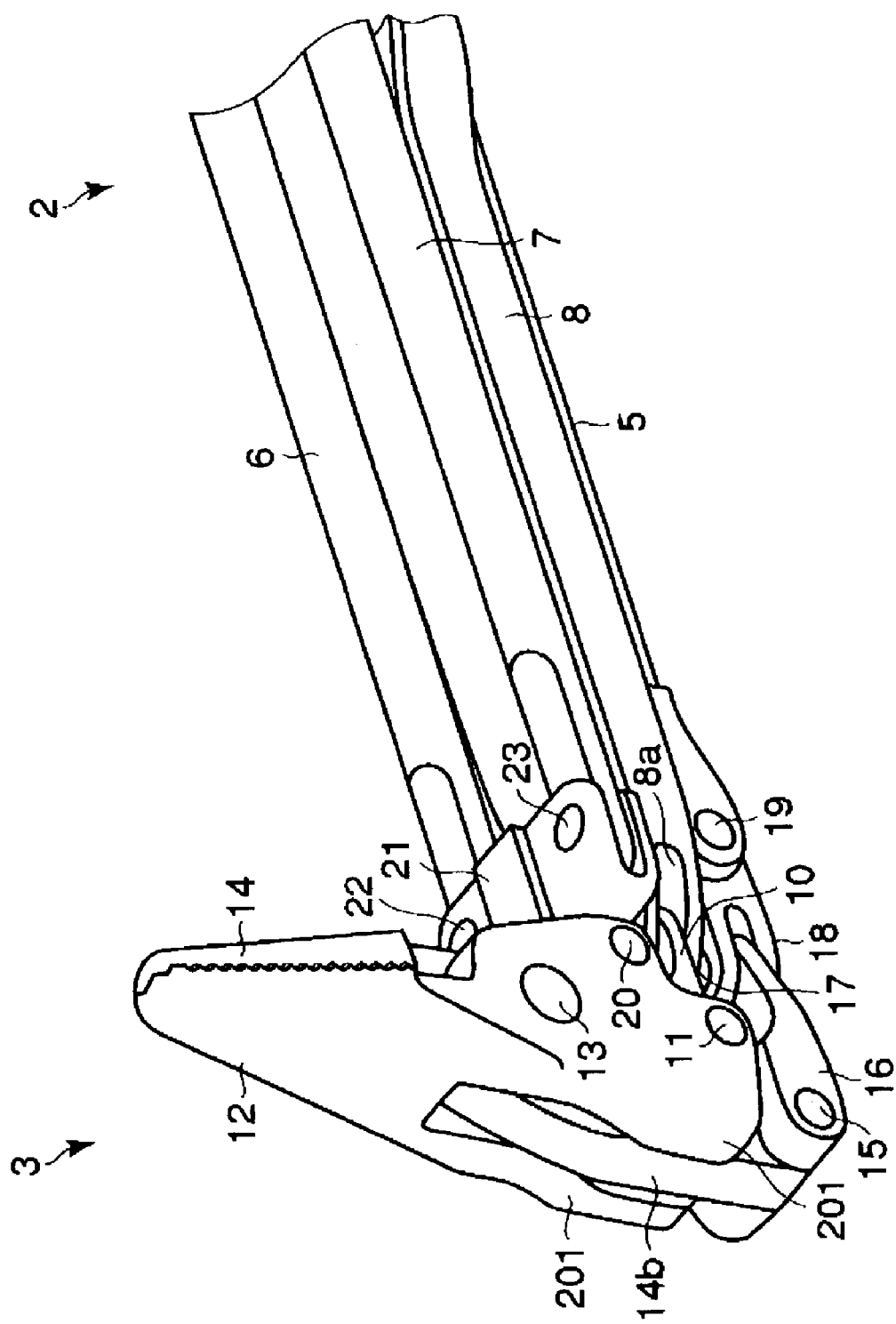
FIG. 2 is a perspective view (viewed from above) of a therapeutic part of the surgical therapeutic instrument shown in FIG. 1.
Figure 3:
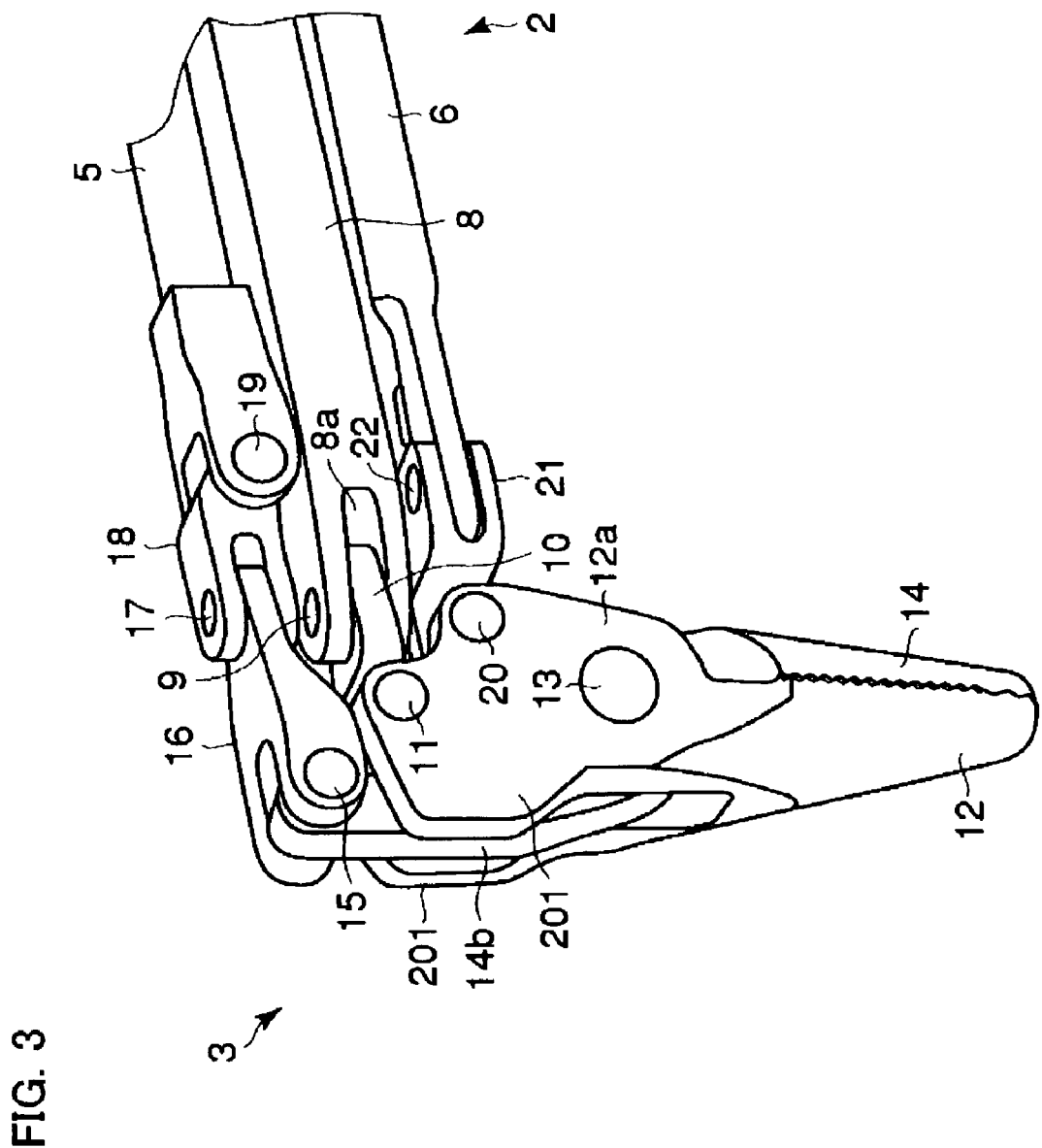
FIG. 3 is a perspective view (viewed from below) of the therapeutic part of the surgical therapeutic instrument shown in FIG. 1.
Figure 4:
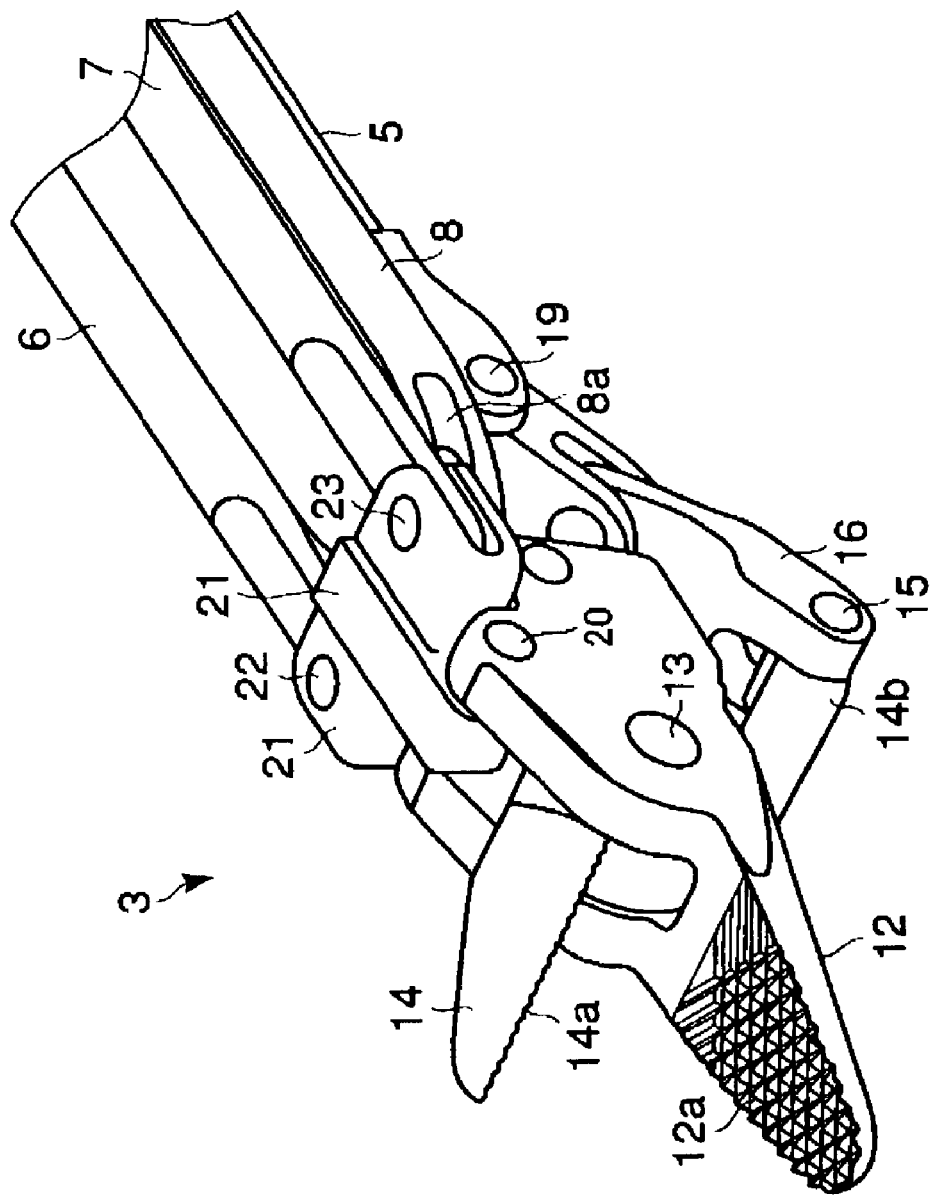
FIG. 4 is a perspective view (viewed from above) of the therapeutic part, which is in an opened state, of the surgical therapeutic instrument shown in FIG. 1.

The therapeutic part 3 will be described below. FIGS. 2 to 4 show the therapeutic part 3. FIG. 2 is a perspective view of the therapeutic part 3 as viewed from above, FIG. 3 is a perspective view of the therapeutic part 3 as viewed from below, and FIG. 4 is a perspective view of the therapeutic part 3 in which a pair of therapeutic halves is opened as viewed from above.

As shown in FIG. 3, a slotted portion 8a is formed in a distal tip portion of the first supporting part 8 provided at the distal tip portion of the inserting part 2. A first turning plate 10 which is turnable to the right and left is connected to the slotted portion 8a by a pivotal shaft 9 which extends vertically (perpendicularly to the axial direction of the inserting part 2). A first pivotal pin 11 which extends to the right and left (in a direction perpendicular to the pivotal shaft 9) is secured to the first turning plate 10, and a proximal portion of a first therapeutic half 12 is upwardly and downwardly pivotally supported by the first pivotal pin 11.

The portion of the first therapeutic half 12 that is near to the first pivotal pin 11 is formed as a bent portion 12a. The second driving rod 6 and the third driving rod 7 are connected to the bent portion 12a by a mechanism which will be described later.

A second therapeutic half 14 is upwardly and downwardly turnably connected to an intermediate portion of the first therapeutic half 12 by a first opening and closing pivotal pin 13. Accordingly, the first therapeutic half 12 and the second therapeutic half 14 are capable of turning with respect to each other about the first opening and closing pivotal pin 13.

One end of a first connecting member 16 is turnably connected to the proximal portion of the second therapeutic half 14 by a first connecting pin 15 which extends to the right and left (in a direction perpendicular to the axial direction of the inserting part 2). The other end of the first connecting member 16 is connected to a second connecting member 18 by a second connecting pin 17 which extends vertically (perpendicularly to the inserting part 2). The other end of the second connecting member 18 is turnably connected to a distal tip portion of the first driving rod 5 by a third connecting pin 19 which extends to the right and left.

As shown in FIG. 2, a second turning plate 21 is connected to the bent portion 12a of the first therapeutic half 12 by a second pivotal pin 20 which extends to the right and left. The proximal side of the second turning plate 21 is widened to the right and left, and a first turning pin 22 and a second turning pin 23 each of which extends vertically (perpendicularly to the axial direction of the inserting part 2) are provided in the state of being spaced part from each other between the right side and the left side of the proximal side of the second turning plate 21. The first turning pin 22 is connected to the second driving rod 6, while the second turning pin 23 is connected to the third driving rod 7.

Incidentally, the space between each of the first driving rod 5, the second driving rod 6 and the third driving rod 7 is restricted to a constant distance in such a manner that the positions of the respective driving rods 5, 6 and 7 are restricted on a plane perpendicular to the longitudinal direction of the inserting part 2 by a first space restricting portion (for example, guide holes (not shown)) provided on the proximal side of the first supporting part 8 (the driving rods 5, 6 and 7 are allowed to move back and forth, but their upward, downward, rightward and leftward motions are. restricted). In addition, a second supporting part 31 (refer to FIG. 8) which will be described later is provided on the proximal side of the inserting part 2, and the space between each of the driving rods 5, 6 and 7 is also restricted to the constant distance by a second space restricting portion (for example, guide holes (not shown)) provided on the distal tip side of the second supporting part 31. Furthermore, the backbone 61 shown in FIG. 21 also serves as a third space restricting portion at its proximal portion (a portion connected to the connecting portion 51). Accordingly, the first driving rod 5, the second driving rod 6 and the third driving rod 7 are constructed to constantly maintain a mutually parallel state. Accordingly, for example, a gastightness retaining member (not shown) can be easily disposed in a portion where the driving rods 5, 6 and 7 run parallel to one another. Therefore, the gastightness of a surgical therapeutic instrument having a plurality of driving rods movable back and forth can be realized by a simple construction.

As shown in FIG. 4, the first therapeutic half 12 has a gripping surface 12a, and the second therapeutic half 14 has a gripping surface 14a. When in a closed state, the gripping surfaces 12a and 14a are positioned to be parallelly opposed to each other, and can cooperate to grip a target object. Incidentally, the gripping surfaces 12a and 14a are worked into uneven surfaces, as required, so that the gripping surfaces 12a and 14a can reliably grip target objects such as a needle, a suture and a living tissue.

Figure 16:
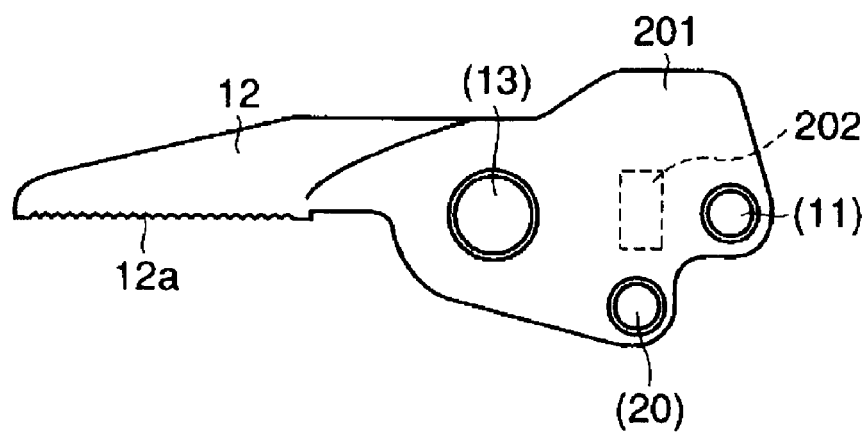
FIG. 16 is a side view of a first therapeutic half of the surgical therapeutic instrument shown in FIG. 1.
Figure 17:
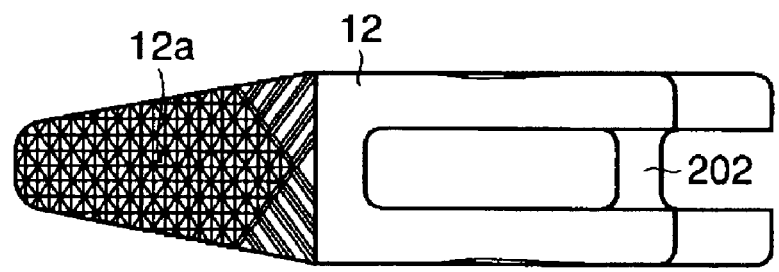
FIG. 17 is a plan view of a first therapeutic half of the surgical therapeutic instrument of FIG. 1.
Figure 18:
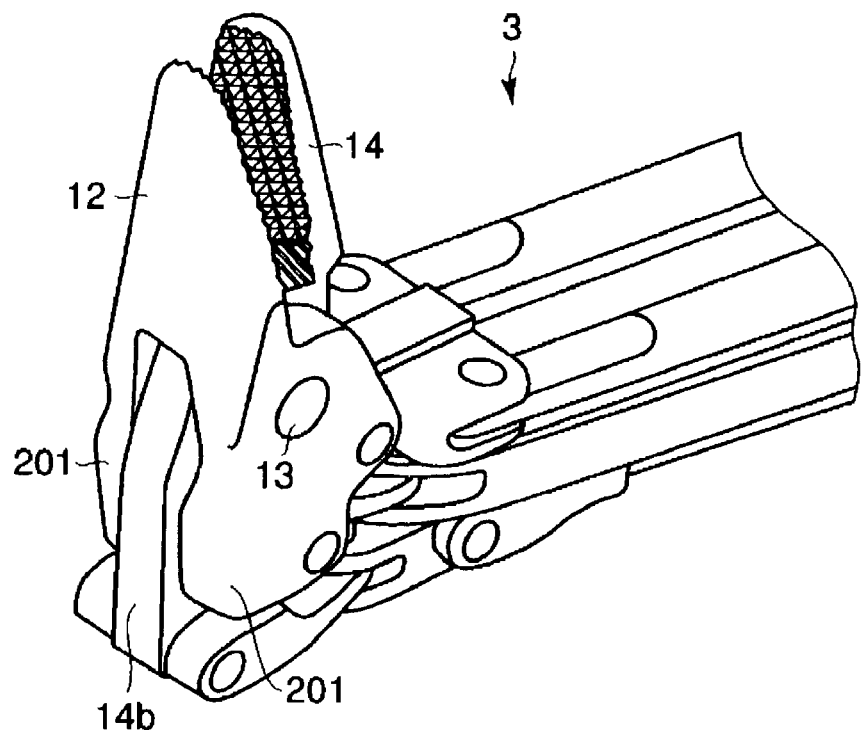
FIG. 18 is a perspective view (viewed from above) of the state in which the therapeutic part of the surgical therapeutic instrument shown in FIG. 1 is fully opened.

FIGS. 16 and 17 show the shape of the first therapeutic half 12 of the therapeutic part 3 of the surgical therapeutic instrument 1 according to the first embodiment. As shown, the first therapeutic half 12 has right and left walls 201 each of which forms an outwardly protruding peripheral portion of an external shape lying on the back side of the gripping surface 12a. In an actually assembled state, a second therapeutic half arm 14b which is on the proximal side of the second therapeutic half 14 is arranged to be disposed between the right and left walls 201 as shown in FIG. 18. Furthermore, the first therapeutic half 12 has an inner wall 202 near its proximal portion in which the first pivotal pin 11 and the second pivotal pin 20 are inserted.

Figure 5:
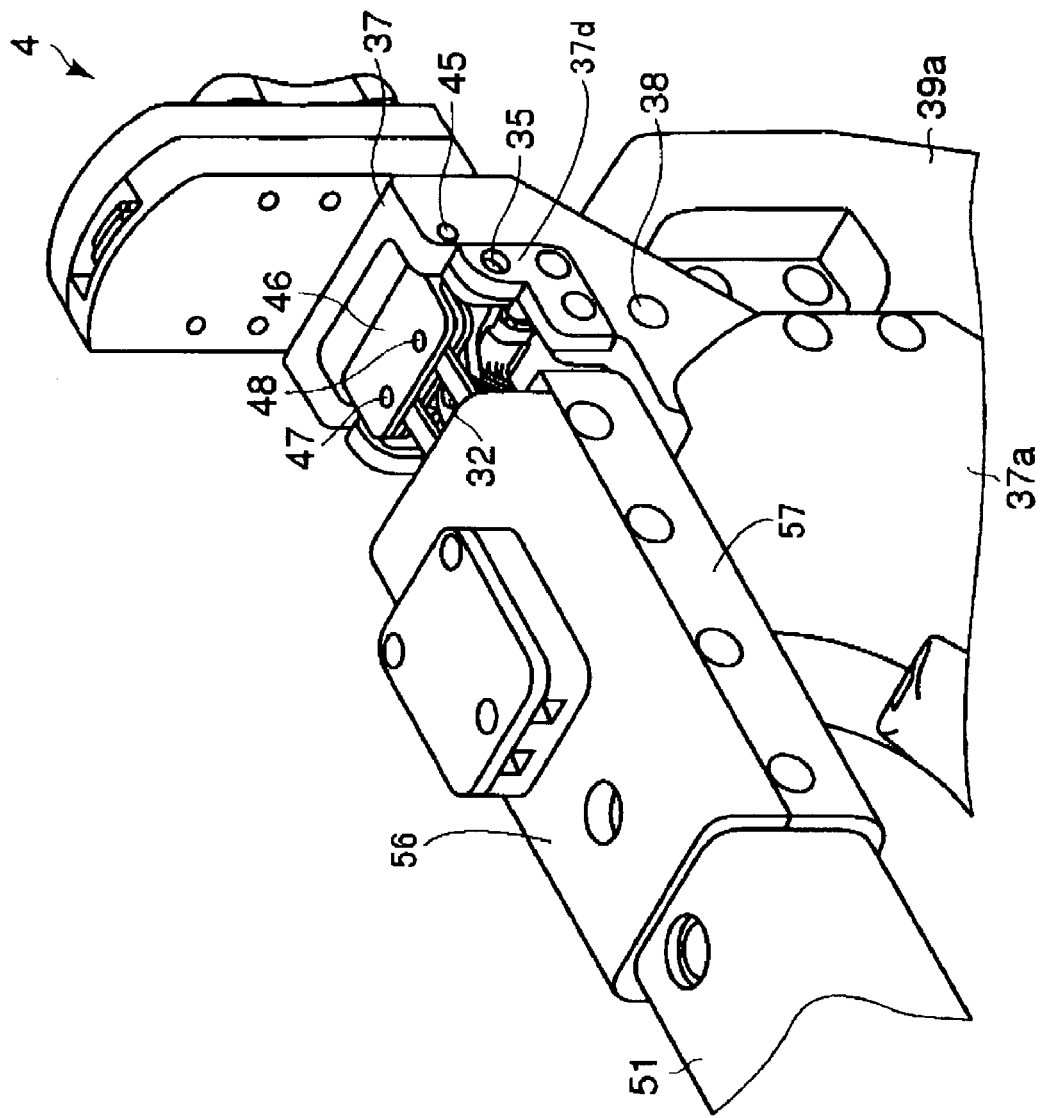
FIG. 5 is a perspective view (viewed from above) of a manipulating part of the surgical therapeutic instrument shown in FIG. 1.
Figure 6:
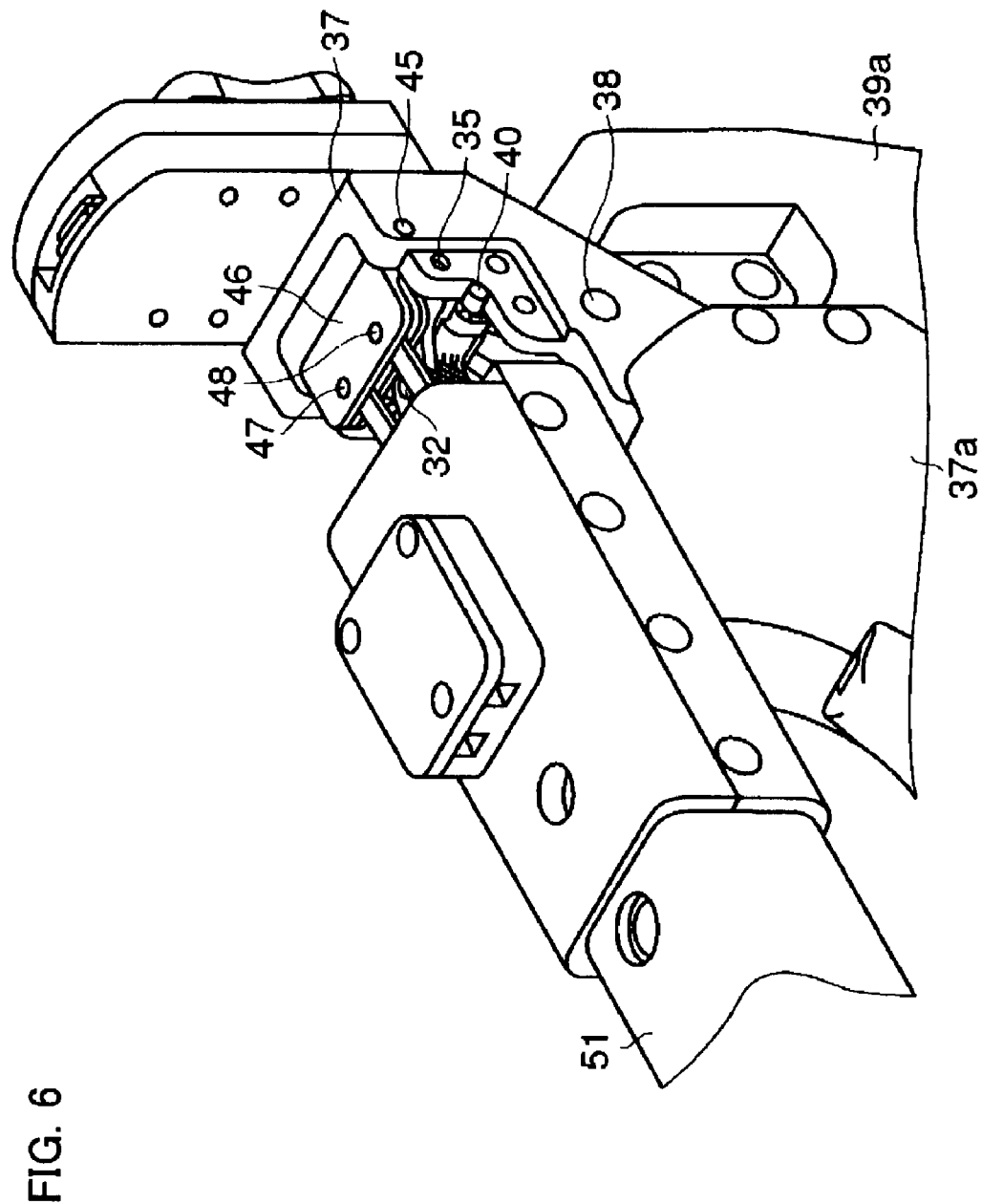
FIG. 6 is a perspective view (viewed from above) showing the manipulating part of the surgical therapeutic instrument of FIG. 1 with the guard of the manipulating part removed.
Figure 7:
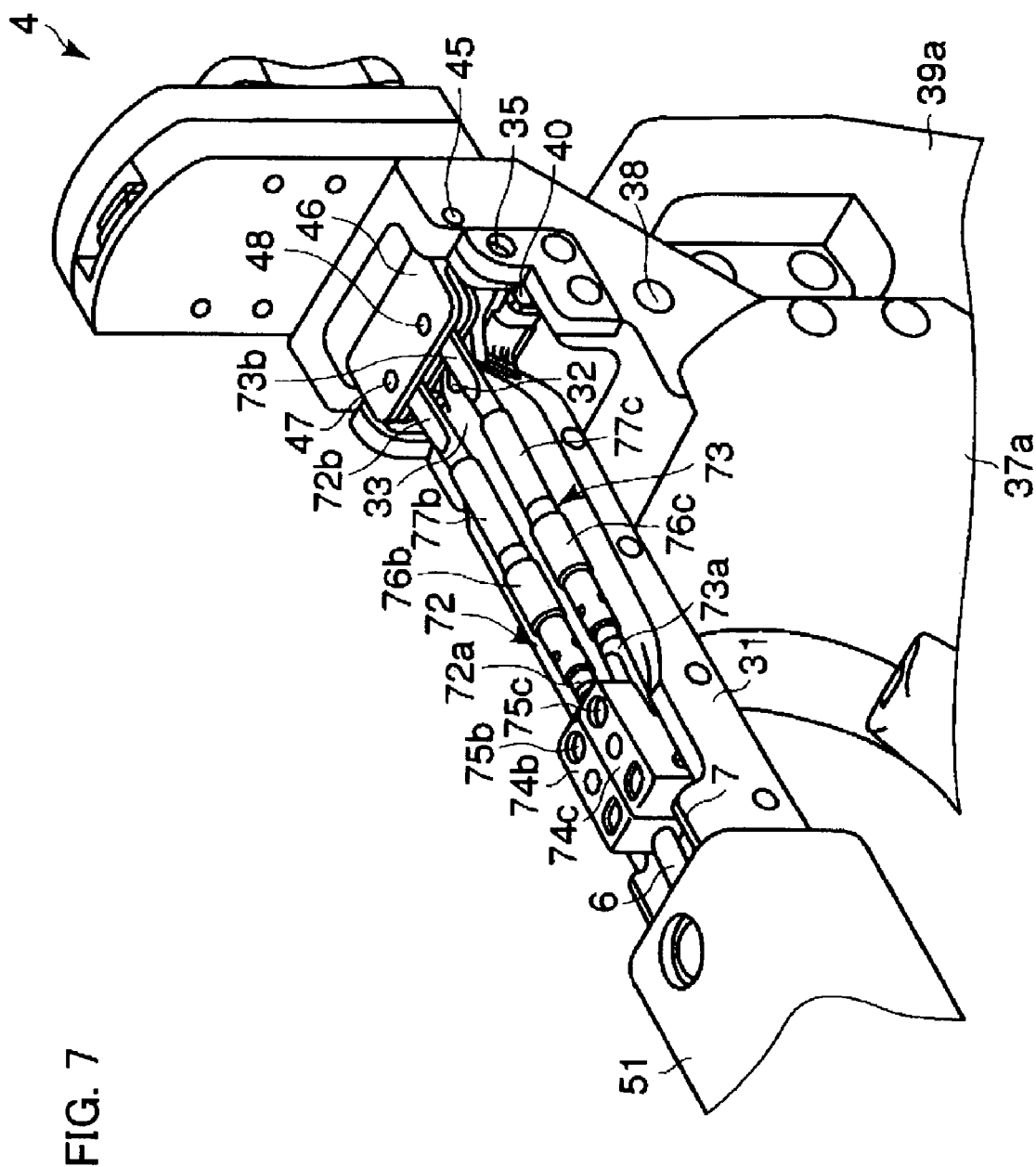
FIG. 7 is a perspective view (viewed from above) showing the manipulating part of the surgical therapeutic instrument of FIG. 1 with the guard of the manipulating part removed.
Figure 8:
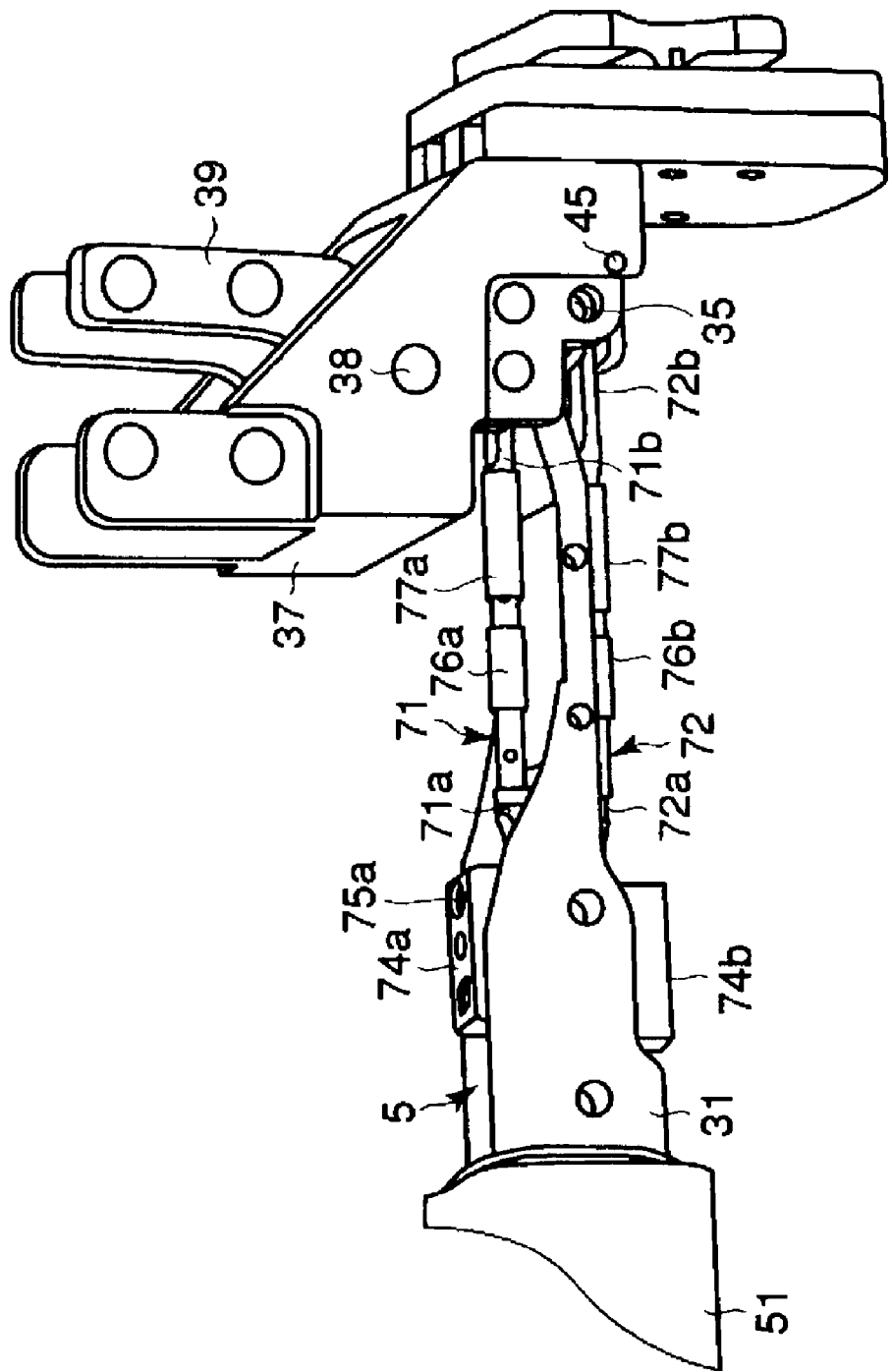
FIG. 8 is a perspective view (viewed from below) showing the manipulating part of the surgical therapeutic instrument of FIG. 1 with the guard and the grip of the manipulating part removed.
Figure 9:
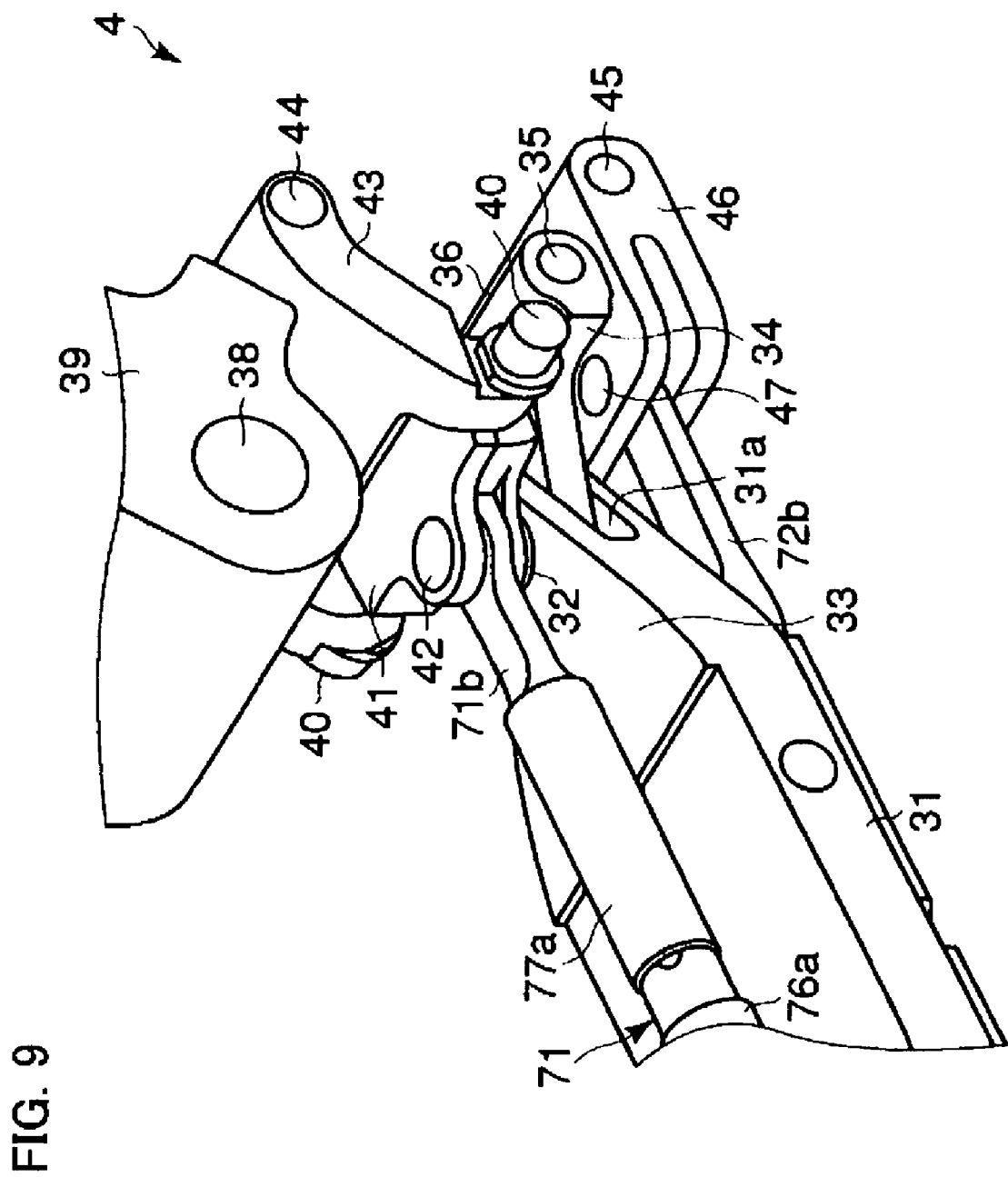
FIG. 9 is a perspective view (viewed from below) showing the manipulating part of the surgical therapeutic instrument of FIG. 1 with the guard of the manipulating part removed.
Figure 12:
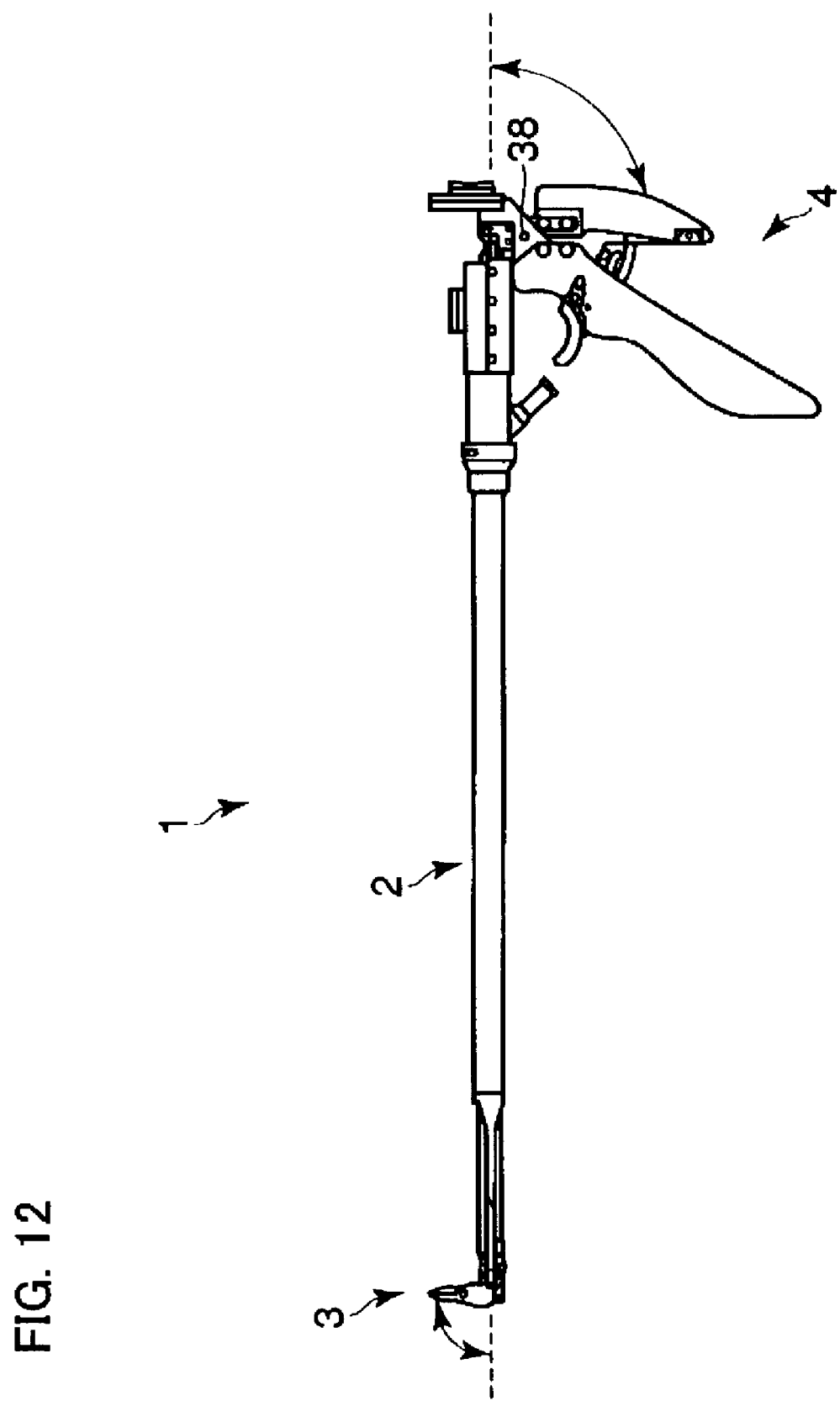
FIG. 12 is a side view of the surgical therapeutic instrument of FIG. 1 in which the therapeutic part is turned up.

The manipulating part 4 will be described below with reference to FIGS. 5 to 9. FIG. 5 is a perspective view of the manipulating part 4 of the surgical therapeutic instrument 1 as viewed from above. FIG. 5 shows the state in which the first handle 37 and the second handle 39 are turned down as shown in FIG. 12. FIG. 6 shows the state in which a portion 37d of a cover for the first handle 37 is removed from the manipulating part 4 placed in the state of FIG. 5. FIG. 7 shows the state in which a top guard 56 and a bottom guard 57 are removed from the manipulating part 4 placed in the state of FIG. 5. Incidentally, the top guard 56 and the bottom guard 57 serve to cover and protect a portion which extends toward a more proximal side from the connecting portion 51 of the inserting part 2. FIG. 8 is a perspective view (viewed from below) of the state in which a first grip 37a is removed from the first handle 37 and a second grip 39a is removed from the second handle 39 in the manipulating part 4 placed in the state of FIG. 7. FIG. 9 is a perspective view (viewed from below) showing the manipulating part 4 of the surgical therapeutic instrument 1 with the first handle 37 removed from the manipulating part 4 placed in the state of FIG. 8. The inner structure of the manipulating part 4 can be understood from FIGS. 5 to 9.

As can be seen from FIG. 8 which is a perspective view viewed from below, at the proximal portion of the inserting part 2 as well, the proximal portion of the first driving rod 5 is arranged to be deviated to a side below the longitudinal central axis of the inserting part 2. As can be seen from FIG. 7 which is a perspective view viewed from above, at the proximal portion of the inserting part 2 as well, the second driving rod 6 and the third driving rod 7 are arranged horizontally symmetrically on a side above the longitudinal central axis of the inserting part 2.

As shown in FIGS. 7 and 8, the second supporting part 31 which protrudes rearwardly (toward the proximal side) and has rigidity is connected to the proximal portion of the inserting part 2 through the connecting portion 51. As shown in FIG. 9, the second supporting part 31 is provided with a first pivotal portion 33 having a second pivotal shaft 32 which extends vertically. A third turning plate 34 is rightwardly and leftwardly turnably connected to the first pivotal portion 33 by the second pivotal shaft 32. The third turning plate 34 is provided with a second pivotal portion 36 having a third pivotal pin 35 which extends to the right and left. The first handle 37 is upwardly and downwardly turnably connected to the second pivotal portion 36 by the third pivotal pin 35 (since FIG. 9 shows the state in which the first handle 37 is removed, the first handle 37 is not illustrated in FIG. 9). Furthermore, the second handle 39 is upwardly and downwardly turnably connected to the first handle 37 by a second opening and closing pivotal pin 38 which extends to the right and left.

In this manner, the first handle 37 is connected to the second supporting part 31 which is disposed at the proximal portion of the inserting part 2, by the third turning plate 34 so that the first handle 37 can be turned upwardly, downwardly, rightwardly and leftwardly. Furthermore, the second handle 39 is upwardly and downwardly turnably connected to the first handle 37.

As shown in FIG. 1, the first handle 37 is provided with the first grip 37a which an operator grips with a finger other than a thumb during manipulation. The second handle 39 is provided with the second grip 39a which the operator manipulates with the thumb during manipulation.

A mechanism which transmits the motion of the second handle 39 to the first driving rod 5 to move the first driving rod 5 back and forth will be described below. As shown in FIG. 8, the proximal portion of the first driving rod 5 is connected to one end of a connector 74a which is movable back and forth in a groove provided in the second supporting part 31 (refer to FIGS. 15A to 15D). The other end of the connector 74a is provided with a connector pin 75a which extends vertically (which extends in a direction perpendicular to the axial direction of the inserting part 2 that is the direction in which the connector 74a moves back and forth). A tip portion 71a of a fourth driving rod 71 is rightwardly and leftwardly turnably connected to the connector pin 75a.

The fourth driving rod 71 has the tip portion 71a, an adjusting member 76a for adjusting the entire length of the fourth driving rod 71, a reinforcing member 77a and a proximal portion 71b in named order from the tip of the fourth driving rod 71. In this manner, the first driving rod 5 and the fourth driving rod 71 constitute a transmission shaft which can be moved back and forth to transmit the manipulation force of the manipulating part 4 to the therapeutic part 3. This transmission shaft is given the degree of freedom that allows the transmission shaft to turn in (to the right or left) at a joint realized by the connector pin 75a, and is also capable of coping with both the case in which the direction of transmission is not linear and the case in which the direction of transmission is variable.

As shown in FIG. 9, a third connecting member 41 is rightwardly and leftwardly turnably connected to the proximal portion 71b of the fourth driving rod 71 by a fourth connecting pin 42 which extends vertically (which extends in a direction perpendicular to the axial direction of the inserting part 2). The third connecting member 41 is upwardly and downwardly turnably connected to a fourth connecting member 43 by a fifth connecting pin 40 which extends to the right and left. The other end of the fourth connecting member 43 is upwardly and downwardly turnably connected to the second handle 39 by a sixth connecting pin 44 which extends to the right and left. In this manner, the first driving rod 5 is connected to the second handle 39 through the connector 74a, the fourth driving rod 71, the third connecting member 41 and the fourth connecting member 43.

A mechanism which transmits the motion of the first handle 37 to the second driving rod 6 and the third driving rod 7 to move the second driving rod 6 and the third driving rod 7 back and forth will be described below. As shown in FIG. 7, the proximal portion of the second driving rod 6 is connected to one end of a connector 74b which is movable back and forth in the groove provided in the second supporting part 31 (refer to FIGS. 14A to 14D). The other end of the connector 74b is provided with a connector pin 75b which extends vertically (which extends in a direction perpendicular to the axial direction of the inserting part 2 that is the direction in which the connector 74b moves back and forth). A tip portion 72a of a fifth driving rod 72 is rightwardly and leftwardly turnably connected to the connector pin 75b.

The fifth driving rod 72 has the tip portion 72a, an adjusting member 76b for adjusting the entire length of the fifth driving rod 72, a reinforcing member 77b and a proximal portion 72b in named order from the tip of the fifth driving rod 72. In this manner, the second driving rod 6 and the fifth driving rod 72 constitute a transmission shaft which can be moved back and forth to transmit the manipulation force of the manipulating part 4 to the therapeutic part 3. This transmission shaft is given the degree of freedom that allows the transmission shaft to turn in (to the right or left) at a joint realized by the connector pin 75b, and is also capable of coping with both the case in which the direction of transmission is not linear and the case in which the direction of transmission is variable.

The proximal portion of the third driving rod 7 is connected to one end of a connector 74c which is movable back and forth in the groove provided in the second supporting part 31 (refer to FIGS. 14A to 14D). The other end of the connector 74c is provided with a connector pin 75c which extends vertically (which extends in a direction perpendicular to the axial direction of the inserting part 2 that is the direction in which the connector 74c moves back and forth). A tip portion 73a of a sixth driving rod 73 is rightwardly and leftwardly turnably connected to the connector pin 75c.

The sixth driving rod 73 has the tip portion 73a, an adjusting member 76c for adjusting the entire length of the sixth driving rod 73, a reinforcing member 77c and a proximal portion 73b in named order from the tip of the sixth driving rod 73. In this manner, the third driving rod 7 and the sixth driving rod 73 constitute a transmission shaft which can be moved back and forth to transmit the manipulation force of the manipulating part 4 to the therapeutic part 3. This transmission shaft is given the degree of freedom that allows the transmission shaft to turn in (to the right or left) at a joint realized by the connector pin 75c, and is also capable of coping with both the case in which the direction of transmission is not linear and the case in which the direction of transmission is variable.

The proximal portion 72b of the fifth driving rod 72 is rightwardly and leftwardly turnably connected to a fourth turning plate 46 by a third connecting pin 47 which extends vertically (which extends in a direction perpendicular to the axial direction of the inserting part 2). Similarly, the proximal portion 73b of the sixth driving rod 73 is rightwardly and leftwardly turnably connected to the fourth turning plate 46 by a fourth connecting pin 48 which extends vertically (which extends in a direction perpendicular to the axial direction of the inserting part. 2). The third connecting pin 47 and the fourth connecting pin 48 are provided in the fourth turning plate 46 in such a manner as to be spaced a predetermined distance part from each other between the right side and the left side of the fourth turning plate 46, and the proximal side of the fourth turning plate 46 is provided with a fourth pivotal pin 45 which extends to the right and left. The first handle 37 is upwardly and downwardly turnably connected to the fourth pivotal pin 45.

In this manner, the second driving rod 6 is connected to the second handle 39 by the connector 74b, the fifth driving rod 72 and the fourth turning plate 46. The third driving rod 7 is connected to the second handle 39 by the connector 74c, the sixth driving rod 73 and the fourth turning plate 46. Incidentally, in the first embodiment, the respective transmission shafts can turn in (to the right or left) by means of the joints realized by the connector pins 75a, 75b and 75c, but each of the transmission shafts may also be constructed to turn in more directions at the same time. Namely, the respective joints provided in the transmission shafts may also be constructed to allow the transmission shafts to turn in not only one direction but also two or more directions.

The construction of a handle fixing mechanism provided on the top of the manipulating part 4 will be described below. As shown in detail in FIGS. 22A, 22B, 23A and 23B, the manipulating part 4 is provided with a handle fixing mechanism 91 which serves as a turn restricting part for restricting (fixing) the turn of each of the handles 37 and 39. The handle fixing mechanism 91 has, as elements provided on the first handle 37 having the first grip 37a, a slide lever (manipulating lever) 92, a slide key 96 connected to the slide lever 92, and a slide housing 94 in which the slide key 96 is accommodated in the state of being movable back and forth. The handle fixing mechanism 91 further has a pair of housing pins 95a and 95b protruded from the slide housing 94 toward the slide lever 92 and spaced apart from each other in the direction in which the slide lever 92 moves, and one lever groove 93 provided on the bottom of the slide lever 92 and capable of engaging with and disengaging from the housing pins 95a and 95b.

The distal tip side of the handle fixing mechanism 91 has, as elements fixedly provided on a guard 56 (on the proximal side of the inserting part 2), a key accommodating housing 97, and a key accommodating portion 98 provided on the proximal side of the key accommodating housing 97 and constructed to accommodate the distal tip portion of the slide key 96.

The sheath 62 of the inserting part 2 will be described below. As shown in FIGS. 1 and 20A, the inserting part 2 has the sheath 62 which externally covers the constituent elements of the inserting part 2 such as the driving rods 5, 6 and 7 between the first supporting part 8 and the connecting portion 51. FIG. 20A shows the state in which the sheath 62 is removed from the inserting part 2. As can be seen from FIG. 20A, the proximal portion of the sheath 62 is removably attached to the connecting portion 51 by means of a bayonet structure. Specifically, a lock pin 65 provided in the connecting portion 51 is capable of engaging with and disengaging from a lock groove 64 provided in a sheath flange 63 of the proximal portion of the sheath 62.

Figure 20B:
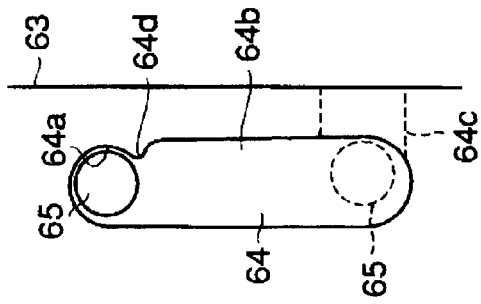
FIG. 20B is a developed view viewed in the direction of an arrow B of FIG. 20A.
Figure 20A:
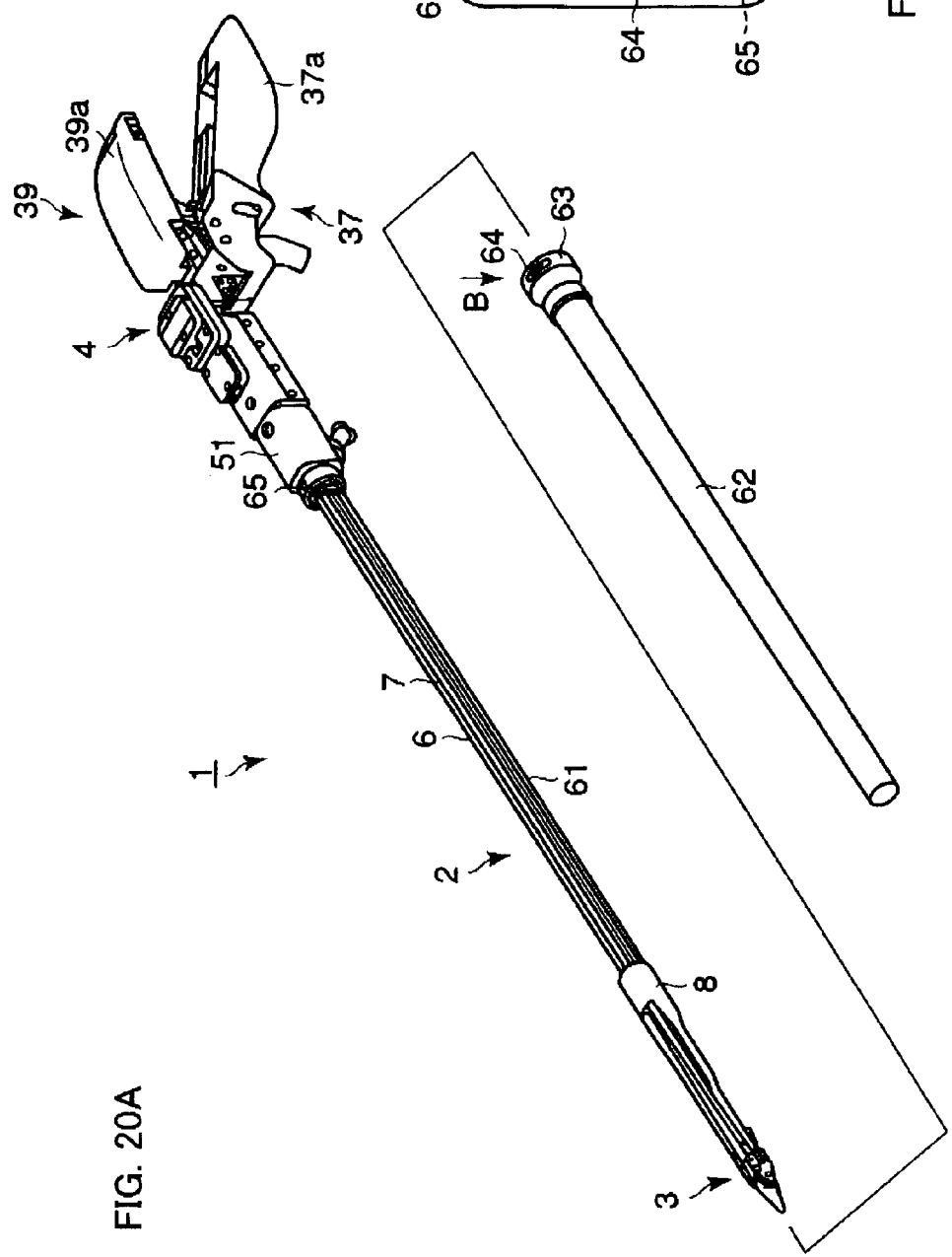
FIG. 20A is a perspective view showing the entire construction of the surgical therapeutic instrument of FIG. 1 with a sheath removed.

As shown in FIG. 20B, the lock groove 64 has a main groove portion 64b which extends in the circumferential direction of the sheath flange 63, an engaging/disengaging groove 64c which extends in the axial direction from one end of the main groove portion 64b and opens at the peripheral end of the sheath flange 63, and a circular-arc-shaped locking groove portion 64a which is formed at the other end of the main groove portion 64b and into which the lock pin 65 locks. A convex portion 64d which protrudes into the inside of the main groove portion 64b is provided between the locking groove portion 64a and the main groove portion 64b on the proximal side of the lock groove 64. The sheath flange 63 is normally urged toward the proximal side by an urging member which is not shown, for example, an elastic member such as rubber, or a spring.

As shown in FIGS. 20A and 21, the backbone (supporting structure) 61 which supports each of the driving rods 5, 6 and 7 along the length thereof is disposed in the interior of the sheath 62. The backbone 61 is formed of, for example, a metal such as SUS (stainless steel), Ti (titanium) or a titanium alloy, or a resin such as PEEK (polyetherketone) or PPSF (polyphenylsulfone). The backbone 61 is constructed to support the above-described space restricting portions and the driving rods 5, 6 and 7, and to restrict the space between each of the driving rods 5, 6 and 7 to the constant distance and constantly maintain the mutually parallel state of the driving rods 5, 6 and 7.

As shown in FIG. 21, the backbone 61 has a shape which allows each of the driving rods 5, 6 and 7 to be exposed when the sheath 62 is removed. Namely, the backbone 61 is formed in a shape which has a first separating wall 61a for providing separation between a space through which the first driving rod 5 extends and a space through which the second driving rod 6 and the third driving rod 7 extend, a second separating wall 61b for providing separation between a space through which the second driving rod 6 extends and a space through which the third driving rod 7 extends, and a pair of third separating wall 61c and fourth separating wall 61d which define the space through which the first driving rod 5 extends, on the opposite sides thereof. Accordingly, when the sheath 62 is attached in the state shown in FIG. 21, the second and third driving rods 6 and 7 are surrounded by a portion of the first separating wall 61a, the second separating wall 61b and the sheath 62, while the first driving rod 5 is surrounded by the third and fourth separating walls 61c and 61d, the first separating wall 61a and the sheath 62 (namely, the respective driving rods 5, 6 and 7 are disposed in three grooves formed by the separating walls 61a to 61d and are covered with the sheath 62). On the other hand, when the sheath 62 is removed in the state shown in FIG. 20A, the respective driving rods 5, 6 and 7 are exposed over approximately their full axial lengths while being supported by the backbone 61.

Incidentally, in the first embodiment, the backbone 61 supports each of the driving rods 5, 6 and 7 along the longitudinal direction thereof except the distal tip side and the proximal side of each of the driving rods 5, 6 and 7. However, the backbone 61 may also be constructed to support each of the driving rods 5, 6 and 7 over approximately the full length thereof. Similarly, in the first embodiment, the sheath 62 externally covers the driving rods 5, 6 and 7 and the backbone 61 except the distal side of the inserting part 2. However, the backbone 61 may also be constructed to cover the driving rods 5, 6 and 7 and the backbone 61 over approximately the full length of the inserting part 2.

The function of the surgical therapeutic instrument 1 constructed in the above-described manner will be described below. When the therapeutic part 3 is in the state of being turned up as shown in FIGS. 2 and 3, the second and third driving rods 6 and 7 are moved forwardly at the same time. At this time, the bent portion 12a of the first therapeutic half 12 is forced forwardly through the second turning plate 21, whereby the first therapeutic half 12 is turned. The second therapeutic half 14 connected to the first therapeutic half 12 by the first opening and closing pivotal pin 13 is also turned in the same direction as the first therapeutic half 12. Accordingly, the first and second therapeutic halves 12 and 14 can turn to an approximately horizontal position about the first pivotal pin 11 which extends to the right and left (perpendicularly to the longitudinal central axis of the inserting part 2).

Then, the second driving rod 6 is moved backwardly, while the third driving rod 7 is moved forwardly. At this time, the first turning plate 10 is turned about the first pivotal shaft 9 to the right (as viewed from the side of the manipulating part 4), whereby the first and second therapeutic halves 12 and 14 (the entire therapeutic part 3) are turned to the right about the first pivotal shaft 9.

Contrarily, the second driving rod 6 is moved forwardly, while the third driving rod 7 is moved backwardly. At this time, the first turning plate 10 is turned about the first pivotal shaft 9 to the left (as viewed from the side of the manipulating part 4), whereby the first and second therapeutic halves 12 and 14 (the entire therapeutic part 3) are turned to the left about the first pivotal shaft 9.

In the case where the first therapeutic half 12 and the second therapeutic half 14 are closed, when the first driving rod 5 is moved forwardly, the proximal portion of the second therapeutic half 14 is forced forwardly through the first connecting member 16 and the second connecting member 18. Accordingly, the second therapeutic half 14 is turned about the first opening and closing pivotal pin 13 with respect to the first therapeutic half 12, whereby the therapeutic part 3 is opened. Contrarily, in the case where the therapeutic part 3 is opened, when the first driving rod 5 is moved backwardly, the proximal portion of the second therapeutic half 14 is pulled backwardly by the first connecting member 16 and the second connecting member 18. Accordingly, the second therapeutic half 14 is turned about the first opening and closing pivotal pin 13 with respect to the first therapeutic half 12, whereby the therapeutic part 3 is closed.

As described above, according to the first embodiment, the entire therapeutic part 3 provided with the first therapeutic half 12 and the second therapeutic half 14 which can be opened and closed can be turned in the upward and downward directions and in the rightward and leftward directions.

Accordingly, the first and second therapeutic halves 12 and 14 can be easily made to approach an objective area, whereby the degree of therapeutic freedom can be improved.

An actual manipulation of the manipulating part 4 will first be described below with reference to the case of turning up and down the therapeutic part 3. First of all, the operator grips the first grip 37a of the first handle 37 of the manipulating part 4 shown in FIG. 1, by using any finger other than the thumb, and grips the second grip 39a of the second handle 39 with the thumb. Then, the operator turns the first handle 37 and the second handle 39 at the same time by 90 degrees downwardly from the horizontal position shown in FIGS. 10 and 11 about the third pivotal pin 35. During this time, the second and third driving rods 6 and 7 are moved backwardly along the inserting part 2 at the same time by the fourth turning plate 46 and the fifth and sixth driving rods 72 and 73 (refer to FIG. 7). In synchronism with this backward movement, the first driving rod 5 is moved forwardly toward the therapeutic part 3 by the fourth connecting member 43, the third connecting member 41 and the fourth driving rod 71 (refer to FIG. 9)

Accordingly, the first connecting pin 15 is protruded toward the distal tip side by the first connecting member 16 connected to the first driving rod 5 in the therapeutic part 3, and at the same time, the bent portion 12a of the first therapeutic half 12 is pulled backwardly by the second turning plate 21 (refer to FIG. 3). Accordingly, the first and second therapeutic halves 12 and 14 are turned about the first pivotal pin 11 without relatively turning and while maintaining their closed state, until the first and second therapeutic halves 12 and 14 are turned up at 90 degrees. This state is shown in FIG. 12.

Figure 10:
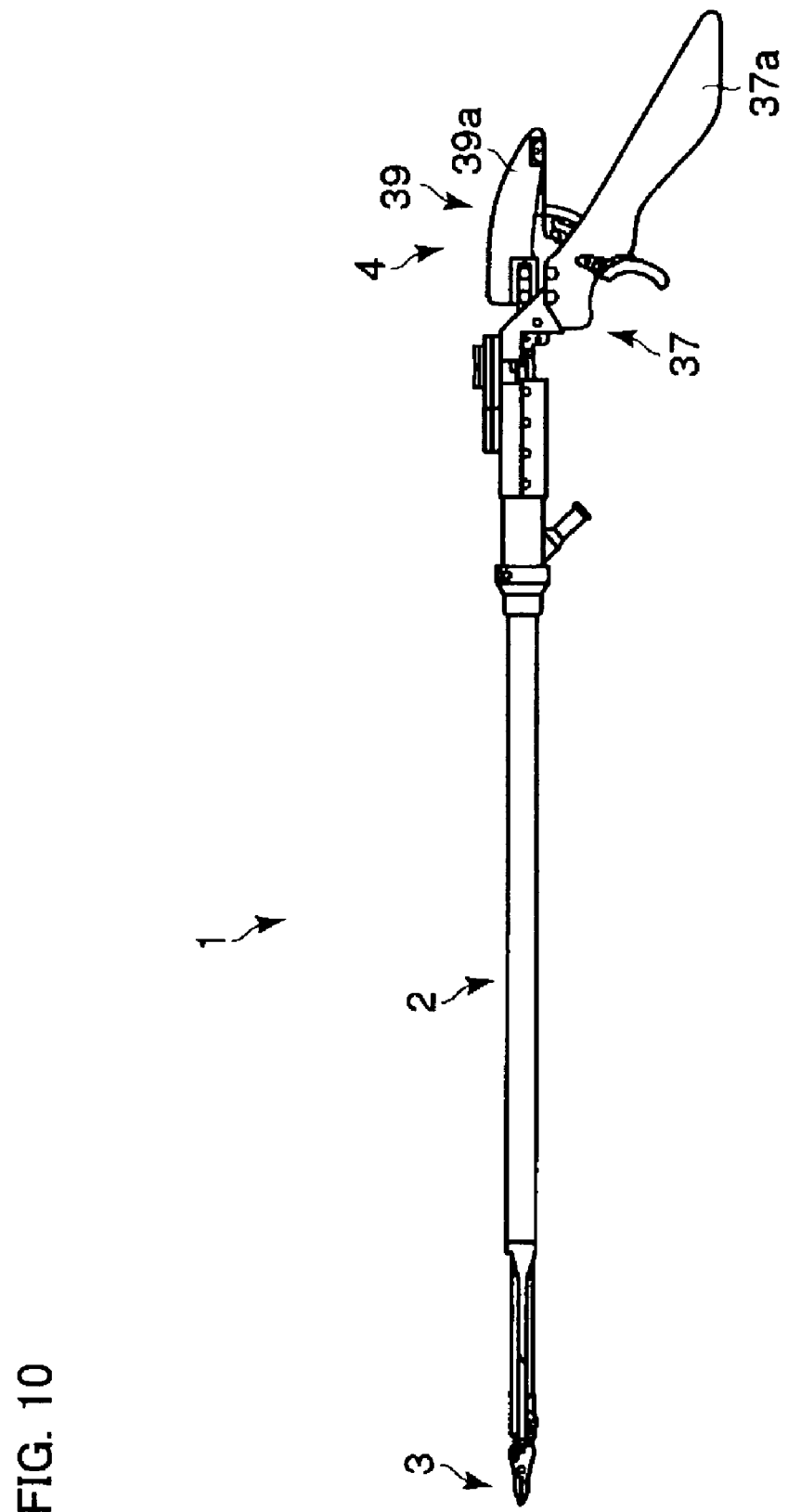
FIG. 10 is a side view of the surgical therapeutic instrument of FIG. 1 in which the therapeutic part is made horizontal.
Figure 11:
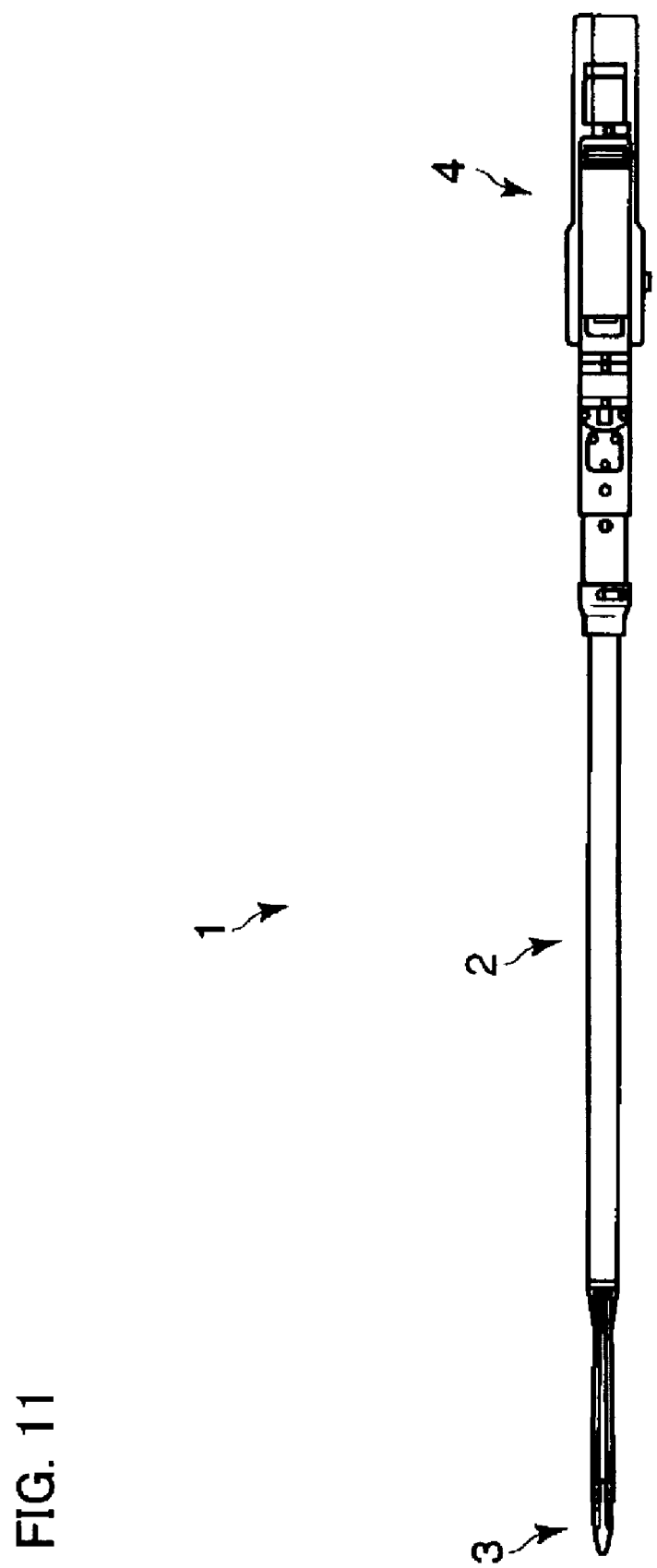
FIG. 11 is a plan view of the surgical therapeutic instrument of FIG. 1 in which the therapeutic part is made horizontal.

Contrarily, the operator turns the first handle 37 and the second handle 39 about the third pivotal pin 35 about the third pivotal pin 35 upwardly from the position shown in FIG. 12, and makes horizontal the first handle 37 and the second handle 39. At this time, the first driving rod 5 is moved backwardly toward the manipulating part 4 by the fourth connecting member 43, the third connecting member 41 and the fourth driving rod 71 (refer to FIG. 9). In addition, the second and third driving rods 6 and 7 are moved backwardly along the inserting part 2 at the same time by the fourth turning plate 46 and the fifth and sixth driving rods 72 and 73 (refer to FIG. 7). Accordingly, the first connecting pin 15 is pulled toward the manipulating part 4 by the first connecting member 16 connected to the first driving rod 5 in the therapeutic part 3, and the bent portion 12a of the first therapeutic half 12 is forced forwardly by the second turning plate 21 (refer to FIG. 3). Accordingly, the first and second therapeutic halves 12 and 14 are turned about the first pivotal pin 11 without relatively turning and while maintaining their closed state, until the first and second therapeutic halves 12 and 14 become approximately horizontal (horizontally straight). This state is shown in FIGS. 10 and 11.

In this manner, in the surgical therapeutic instrument 1 according to the first embodiment, the first handle 37 and the second handle 39 of the manipulating part 4 can be turned upwardly or downwardly about the third pivotal pin 35 to position the therapeutic part 3 straight along the axial direction of the inserting part 2 or to incline the therapeutic part 3 at angles relative to the axis of the inserting part 2.

In addition, when the first manipulating handle 37 and the second manipulating handle 39 are relatively turned, the first and second therapeutic halves 12 and 14 relatively turn, whereby the therapeutic part 3 can be opened (or closed). Namely, when the second handle 39 is turned about the second opening and closing pivotal pin 38 with respect to the first handle 37 (when the first handle 37 and the second handle 39 are opened or closed), the first driving rod 5 is moved forwardly or backwardly by the fourth connecting member 43 and the third connecting member 41. Accordingly, the first connecting pin 15 is moved forwardly or backwardly by the first connecting member 16 connected to the first driving rod 5 in the therapeutic part 3 and the second therapeutic half 14 is turned about the first opening and closing pivotal pin 13 with respect to the first therapeutic half 12, whereby the therapeutic part 3 is opened or closed.

Figure 13:
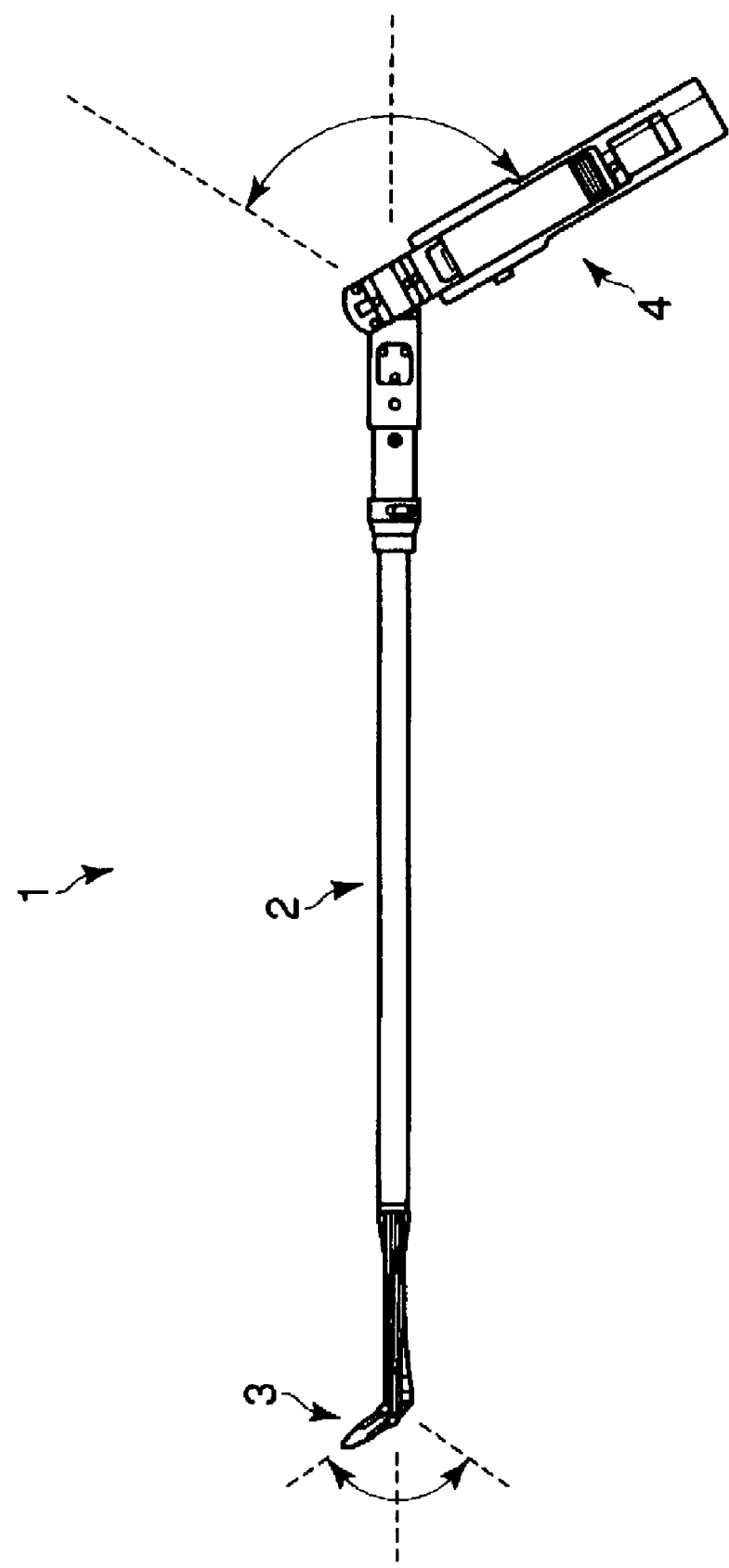
FIG. 13 is a plan view of the surgical therapeutic instrument of FIG. 1 in which the therapeutic part is made horizontal and is turned to the right or left.

A manipulation for turning the therapeutic part 3 to the right and left will be described below. FIG. 13 shows the state in which both the first handle 37 and the second handle 39 are turned horizontally to the left at 60 degrees (as viewed from the side of the manipulating part 4). In this state, the first therapeutic half 12 and the second therapeutic half 14 are turned horizontally to the right at 60 degrees in a closed state according to the turn of the first handle 37 and the second handle 39. Namely, when the first handle 37 and the second handle 39 are turned to the left about the second pivotal shaft 32 at the same time, the second driving rod 6 is moved backwardly and the third driving rod 7 is moved forwardly by the fourth turning plate 46 (refer to FIG. 7). Accordingly, in the therapeutic part 3, the first turning pin 22 is moved backwardly and the second turning pin 23 is moved forwardly, and the first therapeutic half 12 is turned to the right about the first pivotal shaft 9 by the second turning plate 21, whereby the entire therapeutic part 3 is turned to the right (refer to FIG. 2).

Contrarily, when the first handle 37 and the second handle 39 are turned to the right about the second pivotal shaft 32 at the same time, the second driving rod 6 is moved forwardly and the third driving rod 7 is moved backwardly by the fourth turning plate 46 (refer to FIG. 7). Accordingly, in the therapeutic part 3, the first turning pin 22 is moved forwardly and the second turning pin 23 is moved backwardly, and the first therapeutic half 12 is turned to the left about the first pivotal shaft 9 by the second turning plate 21, whereby the entire therapeutic part 3 is turned to the left (refer to FIG. 2).

In this manner, in the surgical therapeutic instrument 1 according to the first embodiment, in synchronism with the rightward movement of the first and second handles 37 and 39, the first and second therapeutic halves 12 and 14 are turned to the left while maintaining the state of being approximately parallel to the first and second handles 37 and 39. In synchronism with the leftward movement of the first and second handles 37 and 39, the first and second therapeutic halves 12 and 14 are turned to the right while maintaining the state of being approximately parallel to the first and second handles 37 and 39. Namely, the therapeutic part 3 can be turned in an arbitrary direction by the manipulation of turning the first and second handles 37 and 39 in the upward, downward, rightward and leftward directions.

Incidentally, during the above-described turning and opening and closing manipulations, the space between each of the driving rods 5, 6 and 7 is constantly restricted by the above-described space restricting portions which are respectively provided at the proximal side of the first supporting part 8 and at the distal tip side of the second supporting part 31. Accordingly, during the above-described period, the driving rods 5, 6 and 7 are relatively moved back and forth in the state of being constantly maintained in a mutually parallel relationship.

Figure 14A:
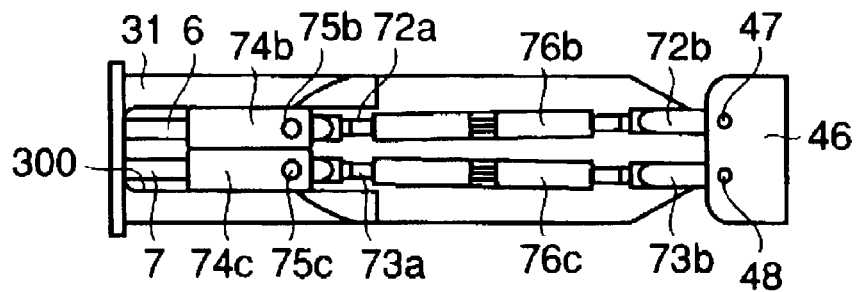
FIGS. 14A to 14D are plan views showing different link arrangements of upper transmission shafts for different states of turning of the surgical therapeutic instrument shown in FIG. 1.

The role of a link of the second driving rod 6 and the fifth driving rod 72 and a link of the third driving rod 7 and the sixth driving rod 73 (the role of an upper link of the manipulating part 4) will be described below. FIGS. 14A to 14D show the functional state of the upper link of the manipulating part 4. Namely, FIG. 14A shows a link arrangement which is formed when the therapeutic part 3 is turned up at 45 degrees and is also turned in a neutral direction between its most rightward and leftward directions. In this state, the link which extends from the second driving rod 6 to the proximal portion 72b of the fifth driving rod 72 and the link which extends from the third driving rod 7 to the proximal portion 73b of the sixth driving rod 73 are horizontally symmetrical and approximately parallel to each other.

Figure 14B:
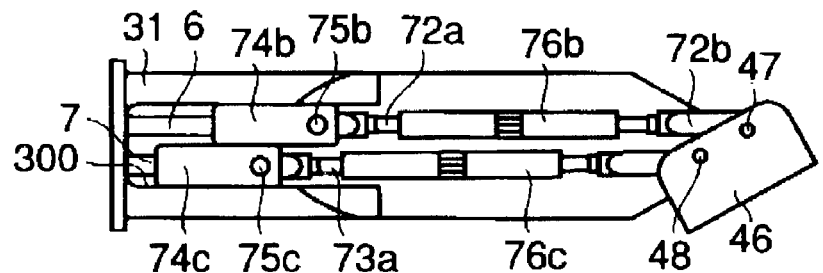
Figure 14C:
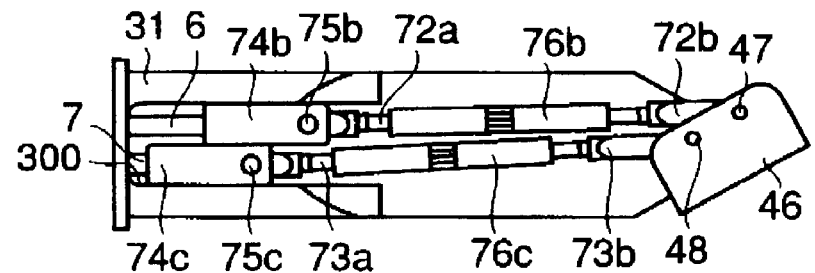
Figure 14D:
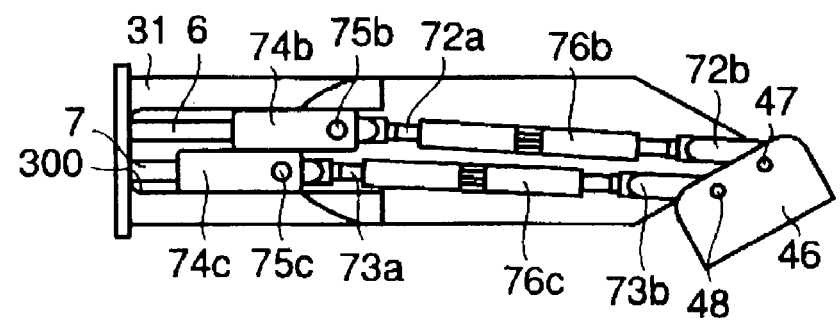

FIG. 14B shows a link arrangement which is formed when the therapeutic part 3 is turned up at 45 degrees and turned to the right at 60 degrees. FIG. 14C shows a link arrangement which is formed when the therapeutic part 3 is made horizontal and turned to the right at 60 degrees. FIG. 14D shows a link arrangement which is formed when the therapeutic part 3 is turned up at 90 degrees and turned to the right at 60 degrees.

In any of these three states (as particularly clearly shown in FIGS. 14C and 14D), the two links are arranged at a position which is horizontally asymmetrical or greatly deviated. In addition, in any of the states, the space between the second driving rod 6 and the third driving rod 7 is restricted by the space restricting portion provided at the distal tip side of the second supporting part 31. However, the tip portion 72a of the fifth driving rod 72 and the tip portion 73a of the sixth driving rod 73 can turn to the right and left to a great extent, respectively, with respect to the connector pins 75b and 75c which are respectively disposed on the connectors 74b and 74c connected to the proximal ends of the second and third driving rods 6 and 7. Accordingly, the proximal-side parts from the tip portion 72a to the third connecting pin 47 and the proximal-side parts from the tip portion 73a to the fourth connecting pin 48 can be rigidly interconnected, and can smoothly transmit turning manipulations.

If the turning links using the connector pins 75b and 75c do not exist, there is a possibility that strain or distortion occurs in the driving rods 6, 7, 72 and 73, because the driving rods 6, 7, 72 and 73 are made of a rigid material over their full lengths. This possibility makes it difficult to design the portion from the turning links to the manipulating part 4 as an arbitrarily short construction. However, in the first embodiment, owing to the joints realized by the connector pins 75b and 75c, it is possible to shorten the length of the portion from the second and third driving rods 6 and 7 to the manipulating part 4 by means of a comparatively simple construction.

Figure 15A:
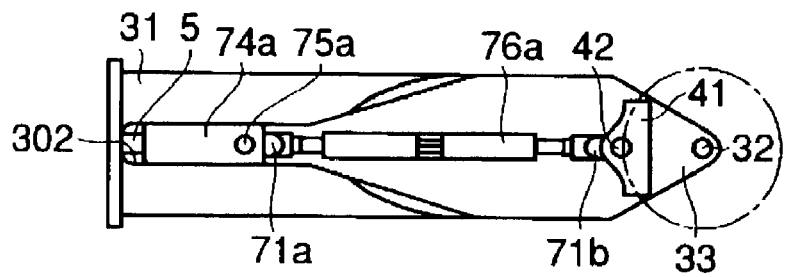
FIGS. 15A to 15D are plan views showing different link arrangements of a lower transmission shaft for different states of turning of the surgical therapeutic instrument shown in FIG. 1.

In addition, the role of a link of the first driving rod 5 and the fourth driving rod 71 (a lower link of the manipulating part 4) will be described below. FIGS. 15A to 15D show the functional state of the lower link of the manipulating part 4. Namely, FIG. 15A shows a link arrangement which is formed when the therapeutic part 3 is turned up at 90 degrees, turned in a neutral direction between the most rightward and leftward directions, and fully opened. FIG. 15C shows a link arrangement which is formed when the therapeutic part 3 is made horizontal, turned in the neutral direction, and closed. In either of these states, the link which extends from the first driving rod 5 to the proximal portion 71b of the fourth driving rod 71 is positioned in the neutral direction between the most rightward and leftward directions.

Figure 15B:
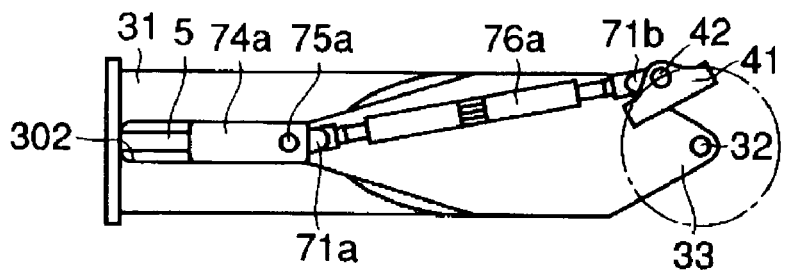
Figure 15C:
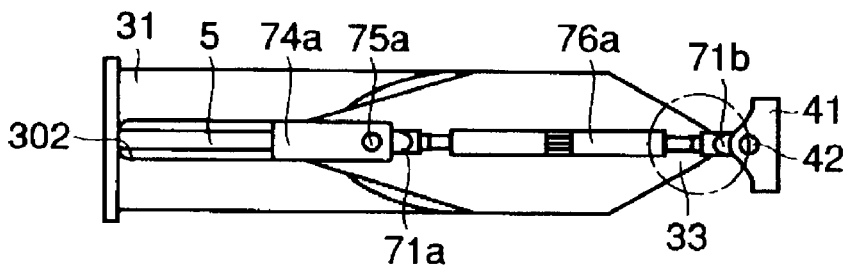
Figure 15D:
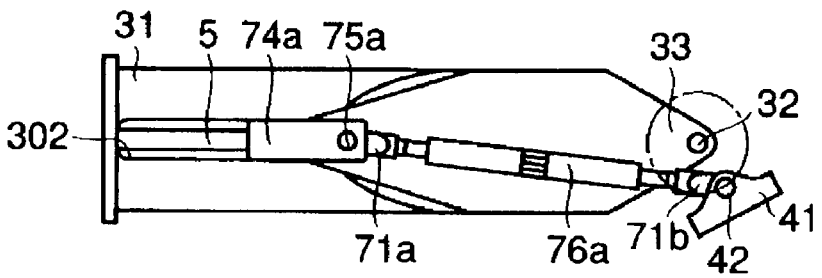

FIG. 15B shows a link arrangement which is formed when the therapeutic part 3 is turned up at 90 degrees, turned to the left at 60 degrees, and fully opened. FIG. 15D shows a link arrangement which is formed when the therapeutic part 3 is made horizontal, turned to the left at 60 degrees, and closed. In any of these two states, the link is arranged at a position which is greatly deviated in one direction. In addition, in any of the states, the position of the first driving rod 5 is restricted by the space restricting portion provided at the distal tip side of the second supporting part 31, but the tip portion 71a of the fourth driving rod 71 can turn to the right and left to a great extent with respect to the connector pin 75*a* disposed on the connector 74*a* connected to the proximal end of the first driving rod 5. Accordingly, the proximal-side part from the tip portion 71*a* to the fourth connecting pin 42 can be rigidly interconnected, and can smoothly transmit turning manipulations.

If the turning link using the connector pin 75*a* does not exist, there is a possibility that strain or distortion occurs in the driving rods 5 and 71, because the driving rods 5 and 71 are made of a rigid material over their full lengths. This possibility makes it difficult to design the portion from the turning link to the manipulating part 4 as an arbitrarily short construction. However, in the first embodiment, owing to the joint realized by the connector pin 75*a*, it is possible to shorten the length of the portion from the driving rod 5 to the manipulating part 4 by means of a comparatively simple construction.

As described above, the surgical therapeutic instrument 1 according to the invention has a position restricting portion for restricting the space between each of a plurality of transmission shafts (the driving rods 5, 6 and 7) (for example, keeping the transmission shafts parallel to one another, and also has joints each turnable in at least one direction. Accordingly, it is possible to restrict the position of each of the transmission shafts (links), and even if the distance between the position restricting portion and the ends of the transmission shafts is shortened, an excessive force does not act on the transmission shafts owing to the action of the joints.

Namely, in the first embodiment, in the case where upward, downward, rightward and leftward turns are combined, the tip portions or the proximal portions of the links are displaced to positions deviated (shifted) from the longitudinal axes of the links themselves (refer to FIGS. 14A to 14D and 15A to 15D). In this case, forces acting to bend the rigid transmission shafts occur between the ends of the transmission shafts and the position restricting means, but in the case of the first embodiment, these forces can be allowed to escape through the joints realized by the connector pins 75*a*, 75*b* and 75*c*. Namely, the problem that the bendings of the transmission shafts exceed their elastic limits owing to the above-described forces does not occur, whereby the lengths of the transmission shafts can be shortened.

In the first embodiment, shaft structures each turnable in one direction are used as the joints. However, it is also possible to adopt other shaft structures such as a joint turnable in more directions and a universal joint turnable in arbitrary directions. Instead of such a mechanical joint, it is also possible to adopt a joint made of, for example, an elastic material (such as silicone rubber or a spring) which interconnects rods having rigidity.

As described above, according to the first embodiment, it is possible to shorten the length of the manipulating part 4 without impairing the range of turning nor decreasing rigidity, by means of a comparatively simple construction. Accordingly, it is possible to improve manipulability in actual use (it is possible to shorten an externally exposed portion led from the proximal end of a trocar to the outside of the body of a patient, thereby improving the manipulability of the surgical therapeutic instrument 1).

The function of the outer peripheral walls 201 and the inner wall 202 arranged in the first therapeutic half 12 will be described below.

Figure 19:
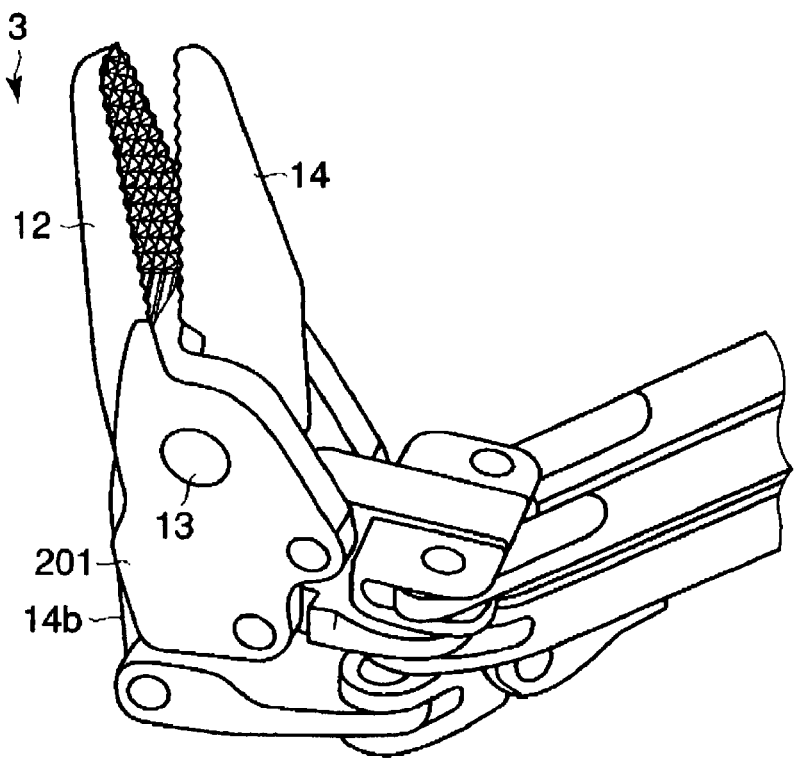
FIG. 19 is a perspective view (viewed from above) of the state in which the therapeutic part is turned to the right from the state shown in FIG. 18.

In the case where the second therapeutic half 14 is opened and closed with respect to the first therapeutic half 12, a force constantly acts on the second therapeutic half arm 14*b* in the longitudinal axial direction of the surgical therapeutic instrument 1. Namely, as shown in FIG. 19, if the second therapeutic half arm 14*b* is to be opened with the therapeutic part 3 turned to the right, an opening force acts on the first opening and closing pivotal pin 13 in an oblique direction (in the longitudinal axial direction of the inserting part 2). Accordingly, a twisting force acts on the second therapeutic half arm 14*b*. As a result, if a very large force acts on the second therapeutic half arm 14*b* during opening or closure, a deviation may occur in the engagement between the first therapeutic half 12 and the second therapeutic half 14.

However, in the case of the construction of the first embodiment, the outer peripheral walls 201 of the first therapeutic half 12 act to restrict the twisting motion of the second therapeutic half arm 14*b* (the outer peripheral walls 201 act to keep the first therapeutic half 12 and the second therapeutic half 14 in a correct positional relationship against the twisting force), whereby it is possible to prevent a deviation from occurring in the engagement between the distal tip portions of the gripping surfaces of the first and second therapeutic halves 12 and 14. In addition, since the first therapeutic half 12 itself to which the twisting force is transmitted has the inner wall 202 (the strength of the first therapeutic half 12 increases), the first therapeutic half 12 can fully tolerate the twisting force, whereby the proximal portion of the first therapeutic half 12 can be prevented from being deformed.

The function of attaching and removing the sheath 62 to and from the inserting part 2 will be described below with reference to FIGS. 20A and 20B.

When the sheath 62 is to be connected to the connecting portion 51, the sheath 62 is fitted onto the surgical therapeutic instrument 1 from the distal tip side thereof. Then, the lock pin 65 of the connecting portion 51 is introduced into the main groove portion 64*b* through the engaging/disengaging groove 64*c* of the lock groove 64 while the sheath flange 63 is being pressed on the end surface of the connecting portion 51 against the urging force of the above-described urging means. The state of the engagement between the lock pin 65 and the main groove portion 64*b* is shown by a broken line in FIG. 20B. Then, the sheath 62 is rotated with respect to the connecting portion 51 to move the lock pin 65 toward the locking groove portion 64*a* in the main groove portion 64*b*. At this time, when the lock pin 65 climbs over the convex portion 64*d* against the urging force of the urging portion which is urging the sheath flange 63 toward the proximal side, the lock pin 65 locks into the locking groove portion 64*a* and the sheath 62 is fixed to the connecting portion 51.

On the other hand, when the sheath 62 is to be disconnected from the connecting portion 51, the sheath 62 needs only to be rotated in the opposite direction to the direction of rotation for connecting the sheath 62 to the connecting portion 51, while an axial force acting to press the sheath flange 63 on the end surface of the connecting portion 51 is being applied to the sheath 62. Accordingly, the lock pin 65 disengages from the locking groove portion 64*a* and climbs over the convex portion 64*d*, so that the engagement between the lock pin 65 and the lock groove 64 is released and the sheath 62 can be removed from the surgical therapeutic instrument 1 on the distal tip thereof.

When the sheath 62 is removed in this manner, the backbone (supporting structure) 61, the first driving rod 5 (which is not shown in FIG. 20A), the second driving rod 6 and the third driving rod 7 are exposed (refer to FIG. 21).

Accordingly, in the case of the surgical therapeutic instrument 1 according to the first embodiment, after use, the interior of the inserting part 2 can be cleaned with ease in a short time. Namely, by removing the sheath 62 to expose the backbone 61 and the driving rods 5, 6 and 7, it is possible to directly clean the backbone 61 and the driving rods 5, 6 and 7 with a brush or the like. In this case, since the driving rods 5, 6 and 7 are supported by the backbone 61 (during cleaning, the inserting part 2 does not only have the driving rods 5, 6 and 7), the driving rods 5, 6 and 7 can be prevented from being deformed during cleaning. Incidentally, if the operator is performing an operation or the like and cannot remove the sheath 62, the operator can easily clean the interior of the inserting part 2 by feeding water into the inserting part 2 from the cleaning port 55.

Accordingly, since the sheath 62 which externally covers the driving rods 5, 6 and 7 and the backbone 61 is constructed to be removable, it is possible to externally expose the driving rods 5, 6 and 7 and the backbone 61 along the longitudinal direction thereof, whereby it is possible to directly clean the driving rods 5, 6 and 7 and the backbone 61 with a brush or the like. Accordingly, cleaning can be performed with ease in a short time.

In addition, since the inserting part 2 has the backbone 61 which supports the driving rods 5, 6 and 7 along the longitudinal direction thereof, the strength of the inserting part 2 is not impaired even if the sheath 62 is removed to expose the interior of the inserting part 2. Namely, even if the sheath 62 is removed, the driving rods 5, 6 and 7 are supported by the backbone 61 (during cleaning, the inserting part 2 does not contain only the driving rods 5, 6 and 7), whereby the driving rods 5, 6 and 7 are not prevented from being deformed during cleaning.

In particular, the backbone 61 of the first embodiment is constructed to support the driving rods 5, 6 and 7 and to restrict the space between each of the driving rods 5, 6 and 7 to a constant distance and constantly maintain the parallel state of the driving rods 5, 6 and 7. Namely, the driving rods 5, 6 and 7 are positioned over the full length of the inserting part 2. Accordingly, the driving rods 5, 6 and 7 are prevented from interfering with one another in the interior of the inserting part 2. Incidentally, it is possible to realize far higher strength by forming the backbone 61 from a metal, and it is also possible to realize far lighter weight by forming the backbone 61 from a resin.

In addition, the surgical therapeutic instrument 1 according to the first embodiment is very simple in structure because the first driving rod 5, the second driving rod 6 and the third driving rod 7 are only supported by the backbone 61 which forms a backbone structure.

The function of the handle fixing mechanism 91 which restricts the turn of the first and second handles 37 and 39 will be described below.

FIGS. 22A and 22B show the state in which the handle fixing mechanism 91 is placed when the surgical therapeutic instrument 1 is in the state of the turn shown in FIGS. 10 and 11; that is to say, the therapeutic part 3 is made horizontal and is turned in the neutral direction between the most rightward and leftward directions. In this state, the slide key 96 is accommodated in the key accommodating portion 98, and the lever groove 93 of the slide lever 92 to which the slide key 96 is connected is engaged with the housing pin 95a disposed on the tip side, whereby the forward and backward movements of the slide key 96 are fixed. Accordingly, all the upward, downward, forward and backward turning movements of the first handle 37 are restricted, whereby the first handle 37 is placed in a substantially fixed state.

In this fixed state, the surgical therapeutic instrument 1 is equivalent to the state of an ordinary surgical therapeutic instrument in which the therapeutic part 3 does not turn. This fixed state can be used in cases such as the case where the degree of turning freedom of the therapeutic part 3 is not needed during an actual surgical manipulation, the case where the surgical therapeutic instrument 1 is to be passed through a trocar to insert or remove the surgical therapeutic instrument 1 into or from a cavity inside a living body, and the case where the therapeutic part 3 and the manipulating part 4 are to be prevented from being damaged by their unnecessary turns during a maintenance process such as cleaning or sterilization after use.

Figures 23A, 23B:
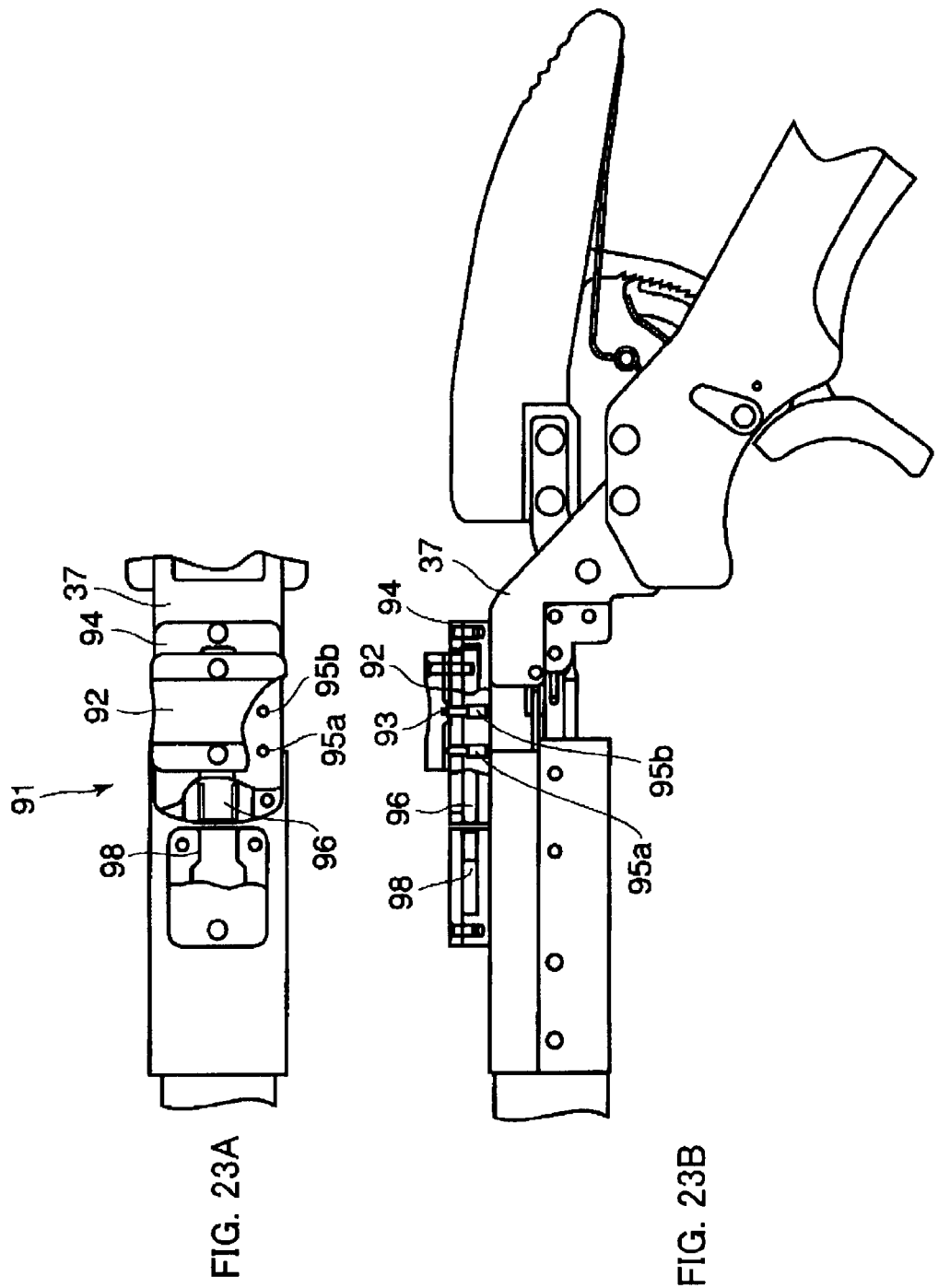
FIG. 23A is a plan view of the handle fixing portion of the manipulating portion which is in a fully opened state.
FIG. 23B is a side view of the handle fixing portion shown in FIG. 23A.

FIGS. 23A and 23B show the state in which the slide lever 92 is moved to the proximal side, unlike in FIGS. 22A and 22B. In this state, the lever groove 93 is engaged with the housing pin 95b disposed on the proximal side and the forward and backward movements of the slide lever 92 are fixed. At this time, the slide key 96 is accommodated in the interior of the slide housing 94, and is completely separated from the key accommodating portion 98. Accordingly, the operator can execute the manipulation of freely turning the first handle 37. This state can be used in the case where the original degree of turning freedom is needed during an actual surgical manipulation.

Furthermore, the slide lever 92 is disposed on the first handle 37. This position is a position where the operator can manipulate the slide lever 92 with a finger of a hand with which to manipulate the manipulating part 4, for example, a position near the front of the second handle 39 and the second grip 39a for opening and closing manipulation (a position on a prolonged line of the external shape of the handles 37 and 39). Therefore, the operator can easily manipulate the slide lever 92 with a thumb with which the operator generally manipulates the second grip 39a. Accordingly, the operator can execute with one hand all the manipulations of the surgical therapeutic instrument 1, such as turning manipulation, opening and closing manipulation, turn restriction, and turn-restriction canceling manipulation (releasing manipulation). Accordingly, a construction of high manipulability can be achieved.

As described above, the surgical therapeutic instrument 1 according to the first embodiment includes the manipulating part 4 and the therapeutic part 3 each of which is turnable in at least two planes, and the turn restricting mechanism 91 which restricts the turn of the manipulating part 4 in at least one plane by the concave-and-convex engagement between the proximal side of the inserting part 2 and the manipulating part 4. Accordingly, the surgical therapeutic instrument 1 can be switched between a first state in which the turn of each of the manipulating part 4 and the therapeutic part 3 is allowed in at least two planes, and a second state in which the turn of each of the manipulating part 4 and the therapeutic part 3 in at least one plane is restricted by the turn restricting mechanism 91. Accordingly, when the surgical therapeutic instrument 1 according to the first embodiment is in the state of normal use, the operator can freely turn the manipulating part 4 (and hence the therapeutic part 3) upwardly, downwardly, rightwardly and leftwardly. In addition, since the operator can utilize the turn restricting means as required, the degree of freedom of manipulation which the surgical therapeutic instrument 1 originally has is not impaired. Namely, during use, the manipulating part 4 (the therapeutic part 3) can be turned with multiple degrees of freedom, whereas the turning position of the manipulating part 4 (the therapeutic part 3) can be fixed as required. Accordingly, the surgical therapeutic instrument 1 is greatly superior in manipulability, and enables the operator to perform efficiently and easily a manipulation containing a series of complicated motions, such as a suturing manipulation.

In addition, the surgical therapeutic instrument 1 according to the first embodiment includes the manipulating lever 92 for manipulating the turn restricting mechanism 91, and the manipulating lever 92 is disposed at a position where the operator can manipulate the slide lever 92 with a finger of a hand with which to manipulate the manipulating part 4 (without removing the hand from the manipulating part 4). Accordingly, the operator can satisfactorily execute the manipulation of starting and canceling the utilization of the turn restricting mechanism 91 with only one hand with which the operator holds the surgical therapeutic instrument 1, whereby the operator can use the surgical therapeutic instrument 1 with greatly superior manipulability.

A second embodiment of the invention will be described below with reference to FIG. 24. The second embodiment relates to a modification of the therapeutic part 3 of the first embodiment. Incidentally, in the following description of the second embodiment, the same reference numerals are used to denote constituent parts common to the first embodiment, and the description of the same constituent parts is omitted.

Figure 24:
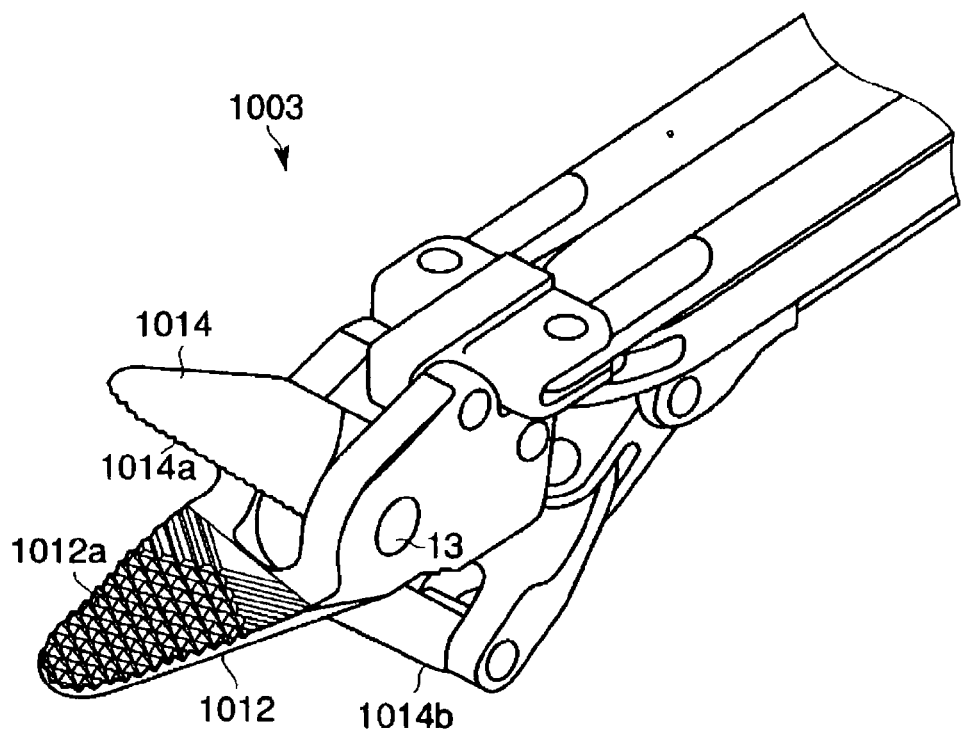
FIG. 24 is a perspective view of the therapeutic part of a second embodiment of the invention (a perspective view showing the fully opened state of the therapeutic part as viewed from above)

The therapeutic part 1003 shown in FIG. 24 has a first therapeutic half 1012, the first opening and closing pivotal pin 13 provided on the first therapeutic half 1012, and a second therapeutic half 1014 turnably connected to the first therapeutic half 1012 by the first opening and closing pivotal pin 13. A gripping surface 1012a is formed on a twisted surface nonparallel to the first opening and closing pivotal pin 13 on a distal tip of the first therapeutic half 1012. A second gripping surface 1014a which is opposed to the first gripping surface 1012a is formed on a distal tip of the second therapeutic half 1014. A second therapeutic half arm 1014b extends to the proximal side beyond the first opening and closing pivotal pin 13.

In the case of the second embodiment, the mutually opposed gripping surfaces 1012a and 1014a of the therapeutic part 1003 are disposed in a twisted positional relationship to the first opening and closing pivotal pin 13 which is an opening and closing shaft for each of the gripping surfaces 1012a and 1014a (that is to say, the gripping surfaces 1012a and 1014a are nonparallel to the opening and closing shaft). Accordingly, the second embodiment makes it possible to hold a needle at a different angle compared to a suturing needle which is held by the gripping surfaces 12a and 14a in the first embodiment. Namely, in the second embodiment, when the operator is to manipulate a circular-arc-shaped needle for use in general endoscopic operation, the operator can appropriately set a sticking angle at which to stick the needle into a living tissue or the like.

For example, in the case where a so-called needle handling manipulation for sticking and extracting a needle into and from a living tissue while holding the needle with the surgical therapeutic instrument 1 placed in the attitude shown in FIG. 12 is to be executed in the longitudinal axial direction of the surgical therapeutic instrument 1, the sticking angle of the needle may not suffice in the case of general non-twisted gripping surfaces of the type used in the first embodiment. In this case, the needle handling manipulation can be executed efficiently and easily, by appropriately setting the twist angle of each of the gripping surfaces 1012a and 1014a. Actually, it is desirable to set a twist angle of ±45 degrees, preferably, approximately ±20 to ±30 degrees (the (+) and (−) signs are signs to be selected according to, for example, whether the operator manipulates the surgical therapeutic instrument with the right hand or the left hand).

As described above, according to the second embodiment, since it is possible to appropriately hold a suturing needle, it is possible to improve the manipulability of the surgical therapeutic instrument.

A third embodiment of the invention will be described below with reference to FIG. 25. The third embodiment relates to another modification of the therapeutic part 3 of the first embodiment. Incidentally, in the following description of the third embodiment, the same reference numerals are used to denote constituent parts common to the first embodiment, and the description of the same constituent parts is omitted.

Figure 25:
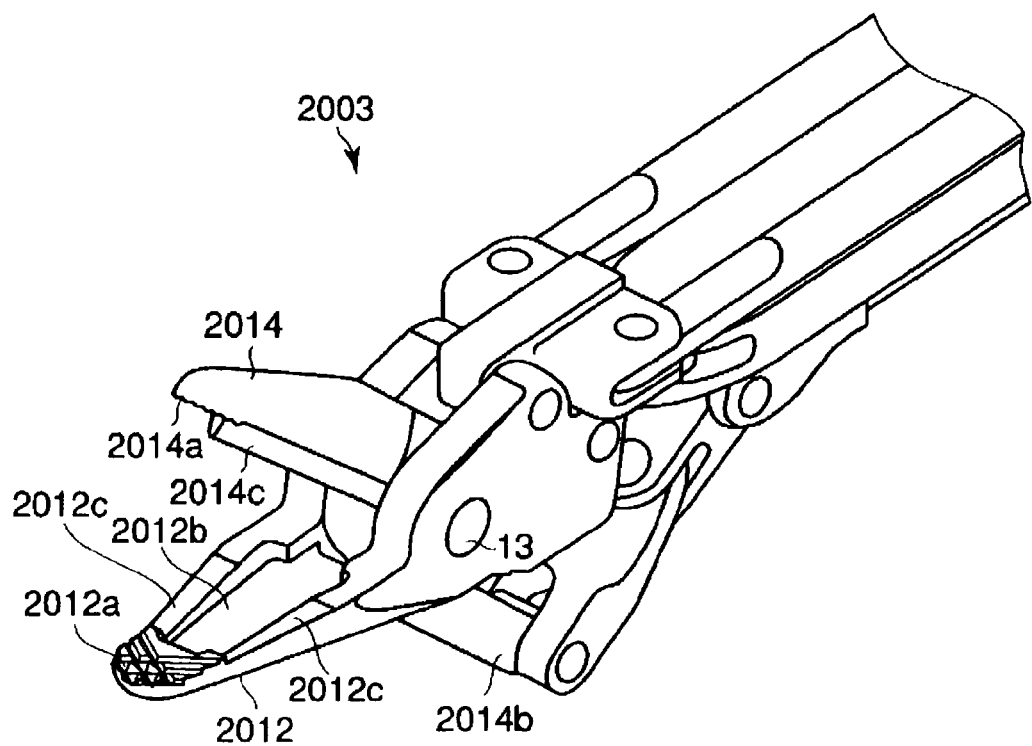
FIG. 25 is a perspective view of the therapeutic part of a third embodiment of the invention (a perspective view showing the fully opened state of the therapeutic part as viewed from above)

The therapeutic part 2003 shown in FIG. 25 has a first therapeutic half 2012, the first opening and closing pivotal pin 13 provided on the first therapeutic half 2012, and a second therapeutic half 2014 turnably connected to the first therapeutic half 2012 by the first opening and closing pivotal pin 13. A gripping surface 2012a is provided on a distal tip of the first therapeutic half 2012, a concave portion 2012b is provided in the gripping surface 2012a on the proximal side thereof, and side walls 2012c which are constructed along the external shape of the first therapeutic half 2012 and are inclined toward the distal tip are provided on the opposite sides of the concave portion 2012b. In this case, the concave portion 2012b may be a through-hole or a bottomed hole. A second gripping surface 2014a which is opposed to the first gripping surface 2012a is provided on a distal tip of the second therapeutic half 2014, and a convex portion 2014c which can be accommodated into the concave portion 2012b of the first therapeutic half 2012 is provided on the proximal portion of the second gripping surface 2014a. A second therapeutic half arm 2014b extends to the proximal side beyond the first opening and closing pivotal pin 13.

In the case of the third embodiment, the two mutually opposed side walls 2012c and the convex portion 2014c of the therapeutic part 2003 can reliably support a bent suturing needle at three points (a point on one of the side walls 2012c, a point on the convex portion 2014c, and a point on the other of the side walls 2012c). Namely, when the operator performs the manipulation of opening and closing the first therapeutic half 2012 and the second therapeutic half 2014, a bent suturing needle can be automatically erected. In addition, since the mutually opposed gripping surfaces 2012a and 2014a are provided on the distal tip, the operator can easily pick up a suture in a living body.

As described above, according to the third embodiment, since it is possible to appropriately hold a suturing needle, it is possible to improve the manipulability of the surgical therapeutic instrument.

A fourth embodiment of the invention will be described below with reference to FIG. 26. The fourth embodiment relates to another modification of the therapeutic part 3 of the first embodiment. Incidentally, in the following description of the fourth embodiment, the same reference numerals are used to denote constituent parts common to the first embodiment, and the description of the same constituent parts is omitted.

Figure 26:
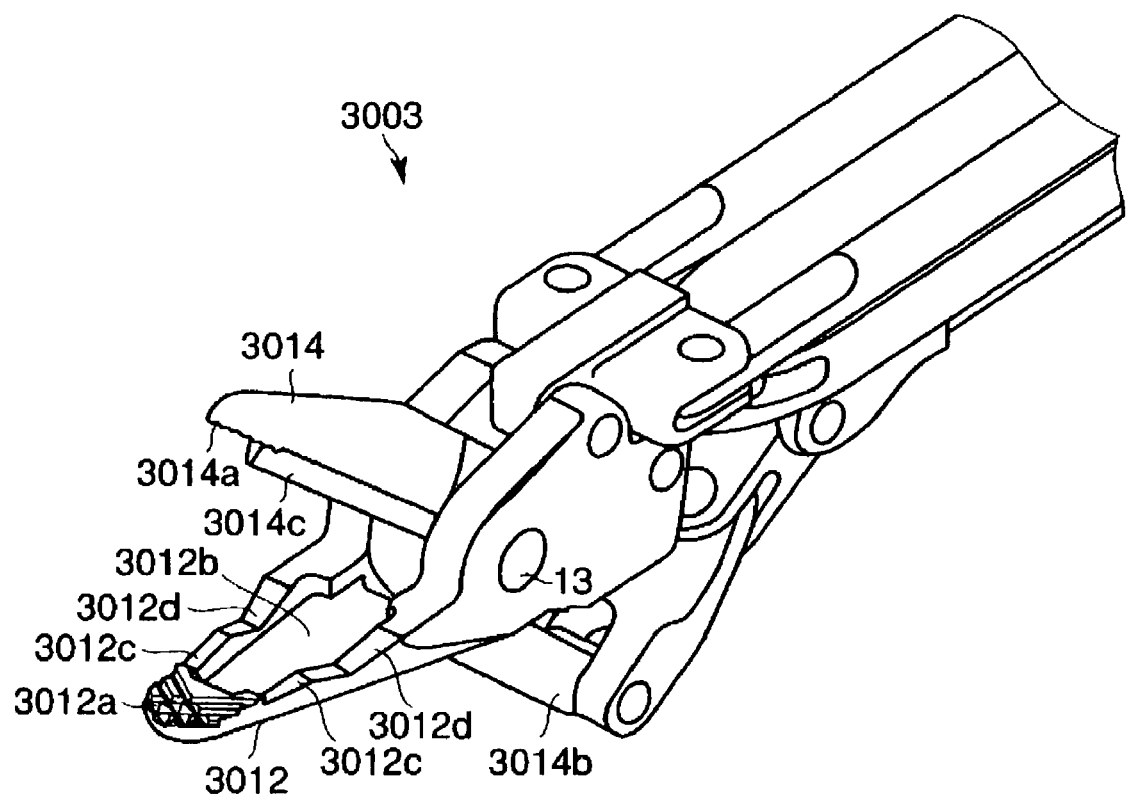
FIG. 26 is a perspective view of the therapeutic part of a fourth embodiment of the invention (a perspective view showing the fully opened state of the therapeutic part as viewed from above)

The therapeutic part 3003 shown in FIG. 26 has a first therapeutic half 3012, the first opening and closing pivotal pin 13 provided on the first therapeutic half 3012, and a second therapeutic half 3014 turnably connected to the first therapeutic half 3012 by the first opening and closing pivotal pin 13. A gripping surface 3012a is provided on a distal tip of the first therapeutic half 3012, a concave portion 3012b is provided in the gripping surface 3012a on the proximal side thereof, and side walls 3012c which are constructed along the external shape of the first therapeutic half 3012 and are inclined toward the distal tip are provided on the opposite sides of the concave portion 3012b. V-shaped side wall concave portions 3012d are provided in portions of the side walls 3012c, respectively. A second gripping surface 3014a which is opposed to the first gripping surface 3012a is provided on a distal tip of the second therapeutic half 3014, and a convex portion 3014c which can be accommodated into the concave portion 3012b of the first therapeutic half 3012 is provided on the proximal portion of the second gripping surface 3014a. A second therapeutic half arm 3014b extends to the proximal side beyond the first opening and closing pivotal pin 13.

In the case of the fourth embodiment, the two mutually opposed V-shaped side wall concave portions 3012d and the convex portion 3014c of the therapeutic part 3003 can reliably support a bent suturing needle at three points. Namely, when the operator performs the manipulation of opening and closing the first therapeutic half 3012 and the second therapeutic half 3014, a bent suturing needle can be automatically erected and can also be held in a constant state in a direction perpendicular to the longitudinal central axis of the first and second therapeutic halves 3012 and 3014. In addition, since the mutually opposed gripping surfaces 3012a and 3014a are provided on the distal tip, the operator can easily pick up a suture in a living body.

As described above, according to the fourth embodiment, since it is possible to appropriately hold a suturing needle, it is possible to improve the manipulability of the surgical therapeutic instrument.

Figure 27:
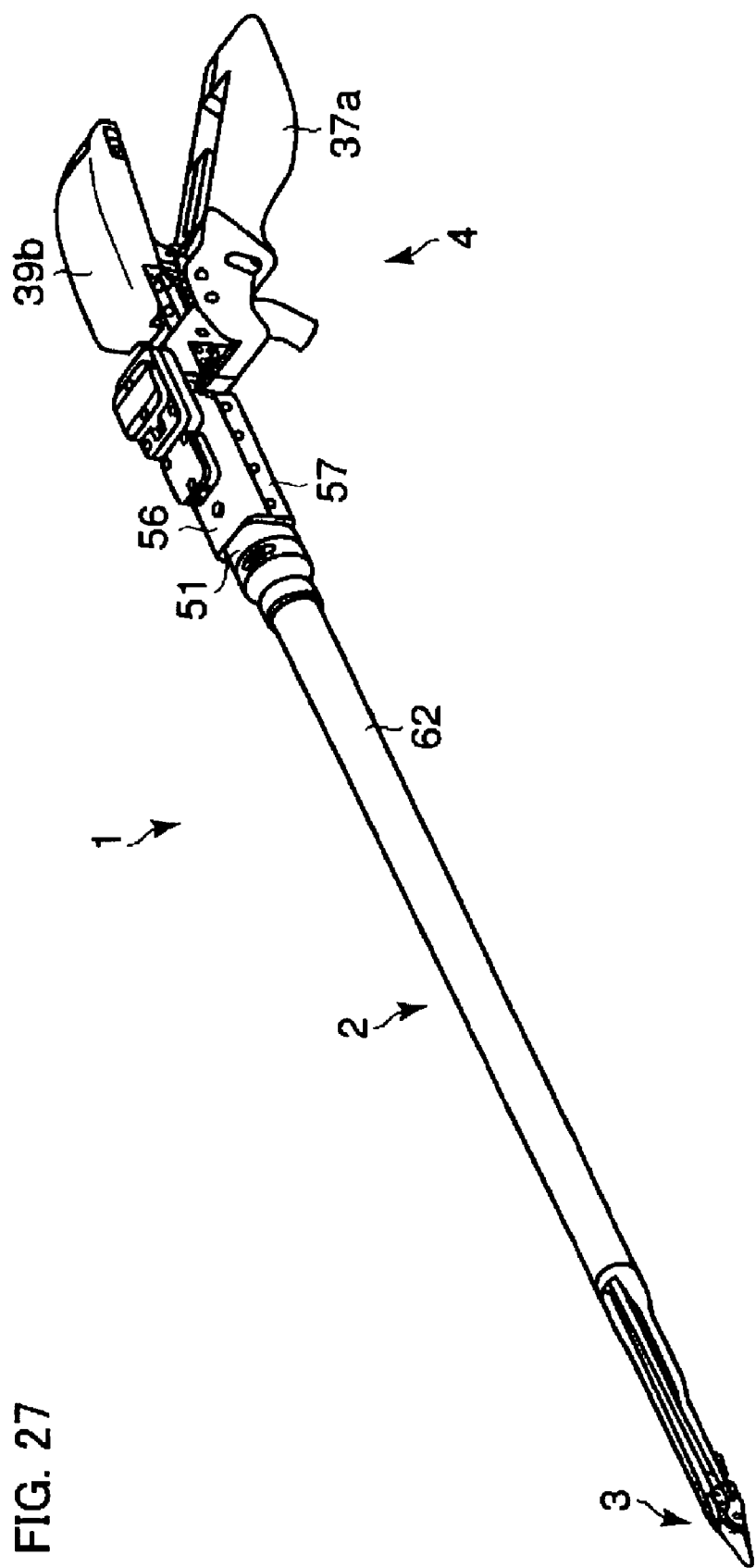
FIG. 27 is a perspective view of the entire construction of a surgical therapeutic instrument according to a fifth embodiment of the invention.
Figure 28:
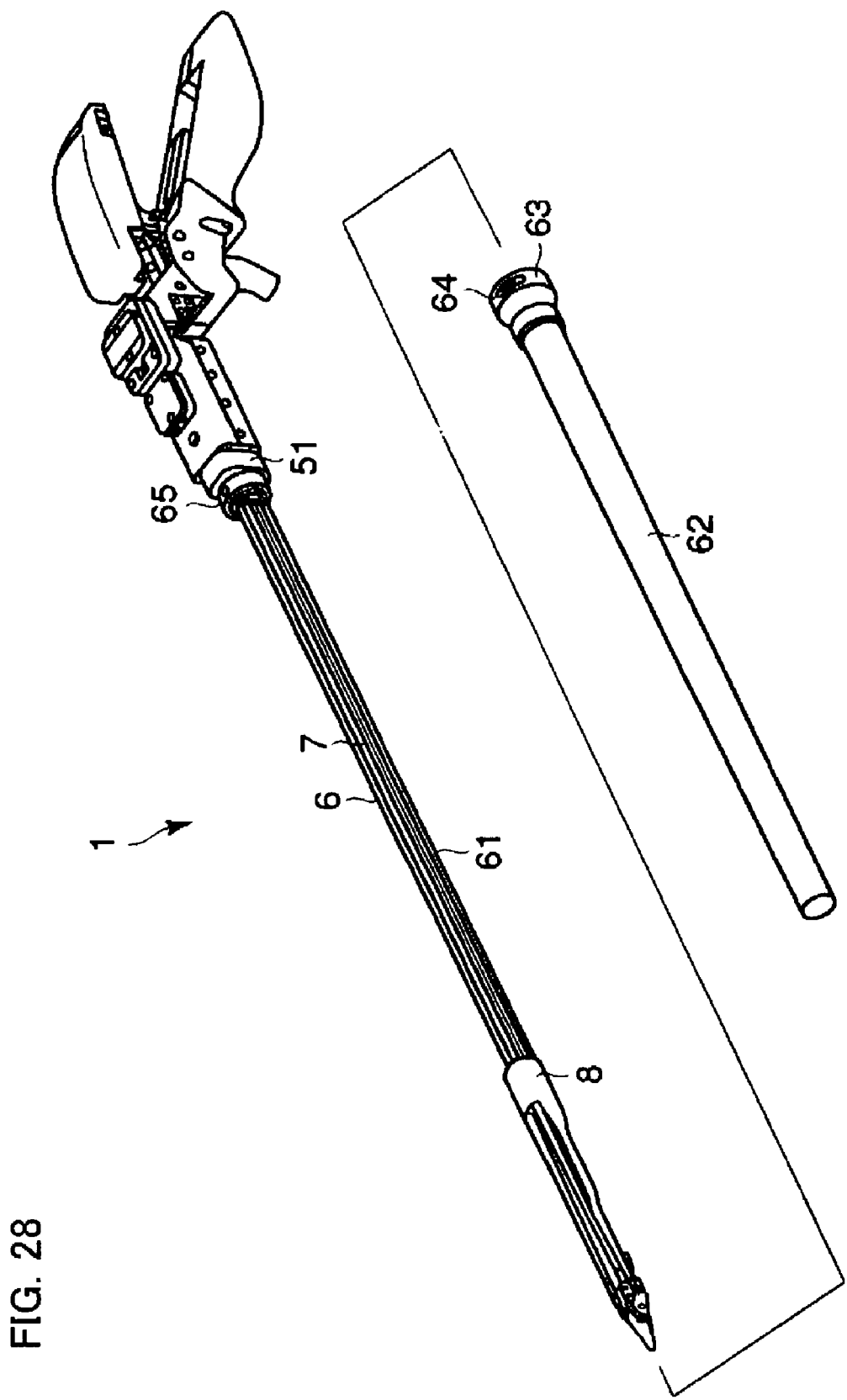
FIG. 28 is a perspective view showing the entire construction of the surgical therapeutic instrument shown in FIG. 27 with a sheath removed.

A fifth embodiment of the invention will be described below with reference to FIGS. 27 and 28. The fifth embodiment has a construction in which the cleaning port 55 is omitted from the first embodiment. Incidentally, in the following description of the fifth embodiment, the same reference numerals are used to denote constituent parts common to the first embodiment, and the description of the same constituent parts is omitted.

As shown, the connecting portion 51 of the surgical therapeutic instrument 1 according to the fifth embodiment does not have the cleaning port 55 provided in the first embodiment. Incidentally, the other constructions are the same as those of the first embodiment. Accordingly, in the fifth embodiment, it is possible to obtain functions equivalent to those of the first embodiment except the function of the cleaning port 55.

As described above, in the case where the cleaning port 55 is not provided in the connecting portion 51, the length of the connecting portion 51 can be made shorter than in the case of the first embodiment. Accordingly, the weight of the surgical therapeutic instrument 1 can be reduced. In addition, when the surgical therapeutic instrument 1 is to be introduced into the body of a patient through the trocar, it is possible to reduce the length of the surgical therapeutic instrument 1 that is to be led out (exposed) from the operator side of the trocar. Accordingly, the manipulability of the surgical therapeutic instrument 1 is improved.

In addition, since the cleaning port 55 is omitted, gastight means for the portion of the cleaning port 55 (generally a cap or the like with which to cover the cleaning port 55) can be omitted, and the entire structure of the surgical therapeutic instrument 1 can be made simple.

A sixth embodiment of the invention will be described below with reference to FIGS. 29 to 32. The sixth embodiment resides in an improvement of the handle fixing mechanism according to the first embodiment. Incidentally, in the following description of the sixth embodiment, the same reference numerals are used to denote constituent parts common to the first embodiment, and the description of the same constituent parts is omitted.

Figure 29:
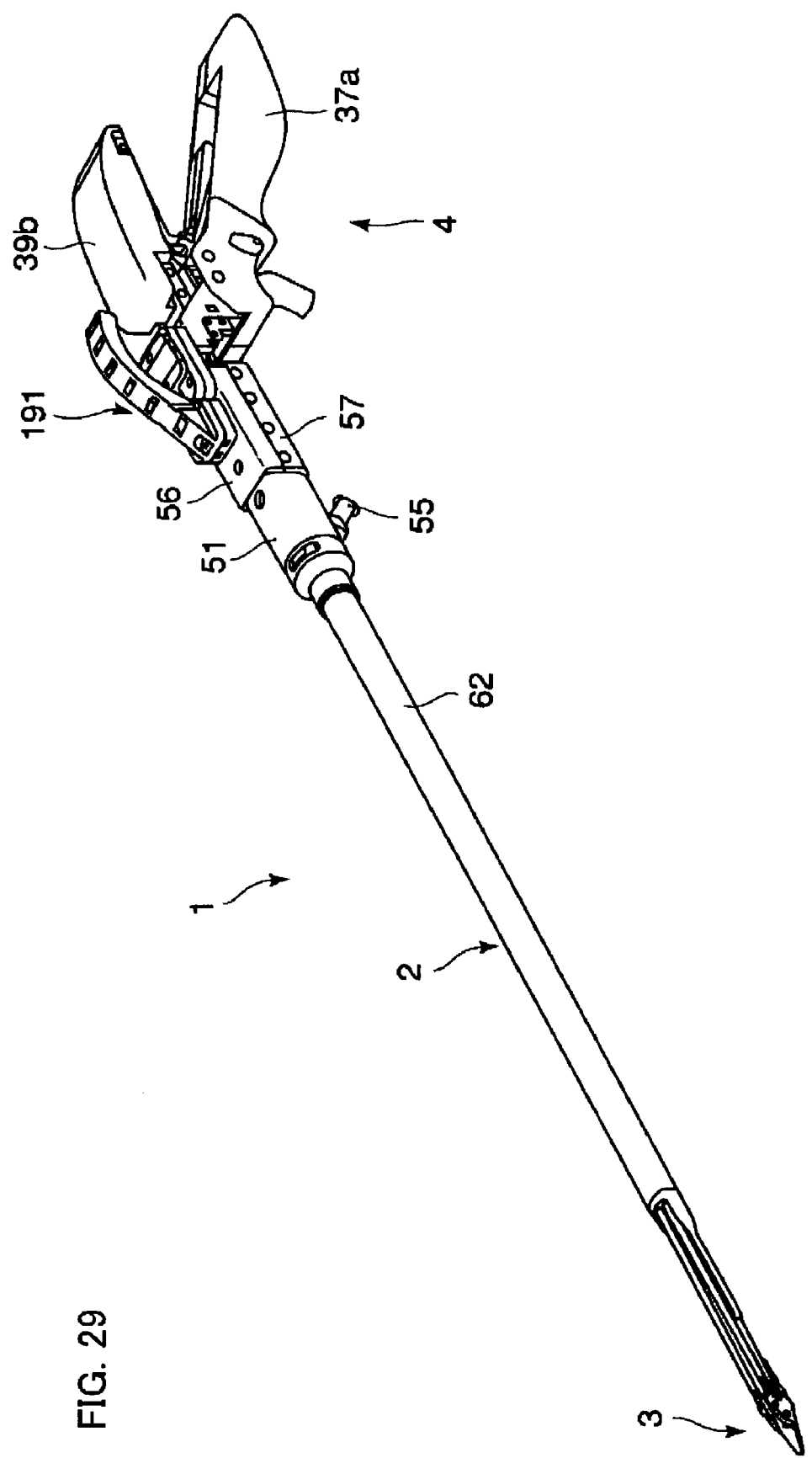
FIG. 29 is a perspective view showing the entire construction of the surgical therapeutic instrument according to a sixth embodiment of the invention.

As shown in FIG. 29, a handle fixing mechanism (turn restricting part) 191 which differs in form from that of the first embodiment is provided on the manipulating part 4 of the surgical therapeutic instrument 1 according to the sixth embodiment. As shown in detail in FIGS. 30 to 32, the turn restricting part 191 has: (1) housing pins 195a, 195b and 195c provided on the slide housing 94 and spaced part from one another in the moving direction of the slide lever 92 in such a manner as to be respectively positioned on the tip side, at an intermediate location and on the proximal side; (2) a key accommodating housing 197 extended in an arch-like shape from the top of the guard 56 on the tip side of the slide housing 94 (the proximal side of the inserting part 2) toward a position above the proximal side; (3) a plurality of key accommodating portions 198a to 198f formed in the key accommodating housing 197 and spaced a predetermined distance apart from one another along the extending direction of the key accommodating housing 197; and (4) a concave groove 199 formed in the key accommodating housing 197 along the inner periphery thereof.

The plurality of key accommodating portions 198a to 198f and the key accommodating portion 98 are arranged from a horizontal state to a 90-degree state at a pitch of 15 degrees along the vertical turning path of the first handle 37 about the third pivotal pin 35. The pitch of the key accommodating portions 198a to 198f and 98 and the angular range in which the key accommodating portions 198a to 198f and 98 are arranged are not limited to those shown in FIGS. 30 to. 32, and may also be arbitrarily set. Incidentally, the other constructions are the same as those of the first embodiment.

Figure 30:
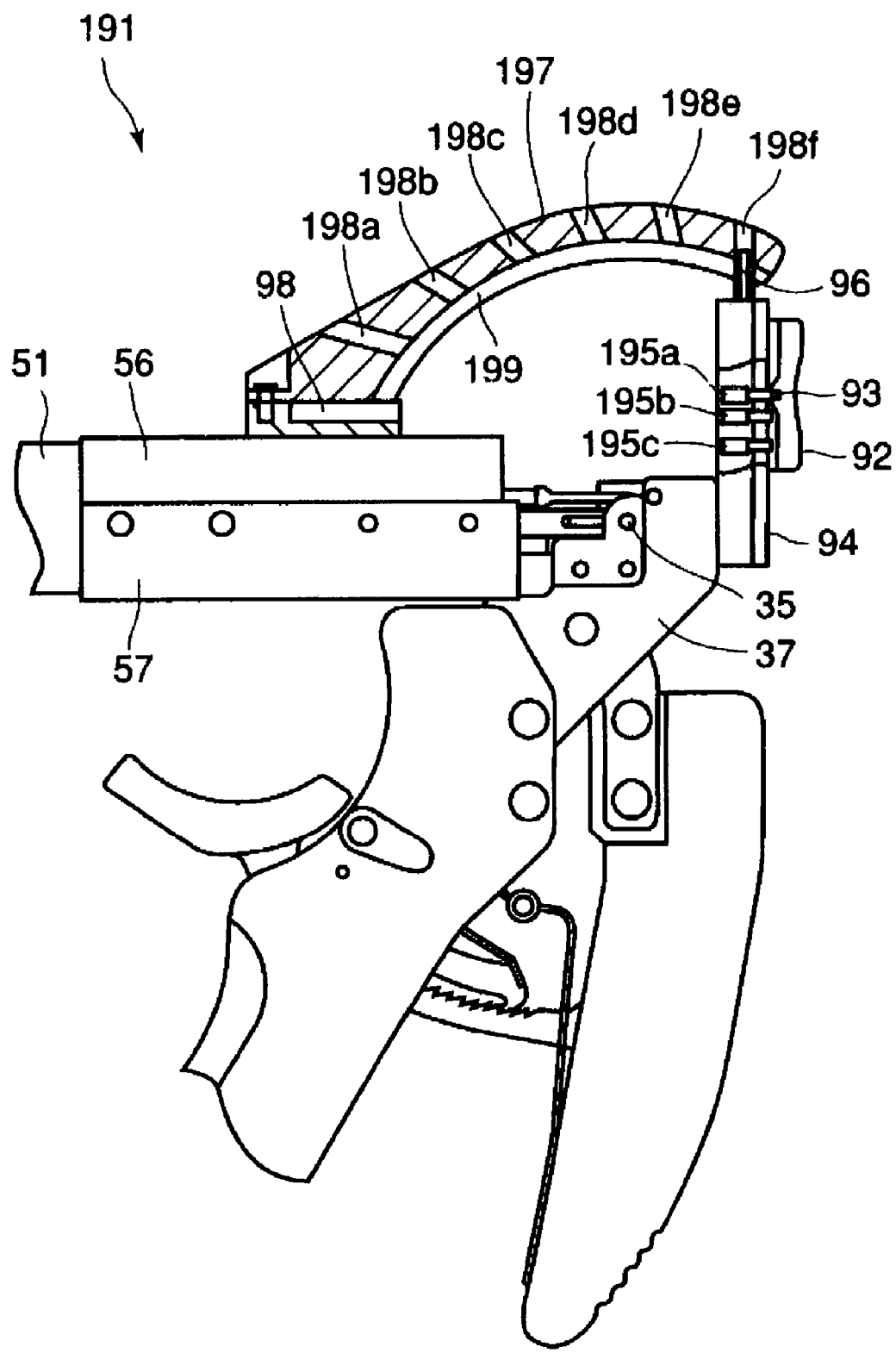
FIG. 30 is a side view showing the locked state of the handle fixing portion of the manipulating part of the surgical therapeutic instrument shown in FIG. 29.

The function of the turn restricting part 191 having the above-described construction will be described below. FIG. 30 shows the state where the surgical therapeutic instrument 1 is in the state of being turned as shown in FIG. 12; that is to say, the therapeutic part 3 is turned up at 90 degrees and is also turned in a neutral direction between its most rightward and leftward directions. In this state, the slide key 96 is accommodated in the key accommodating portion 198f on the most proximal side of the key accommodating housing 197, and the lever groove 93 of the slide lever 92 to which the slide key 96 is connected is engaged with the housing pin 195a positioned on the tip side. In this manner, the forward and backward movements of the slide key 96 is fixed. Accordingly, the upward, downward, rightward and leftward motions of the first handle 37 are restricted, whereby the first handle 37 is placed in a substantially fixed state.

Similarly, the slide key 96 can fixedly engage with the key accommodating portions 198e, 198d, 198c, 198b, 198a and 98. Accordingly, the first handle 37 can be fixed at any of the corresponding angular positions centered about the third pivotal pin 35. Each of the fixed states can be used in cases such as the case where the degree of turning freedom of the therapeutic part 3 is not needed during an actual surgical manipulation and the case where the therapeutic part 3 and the manipulating part 4 are to be prevented from being damaged by their unnecessary turns during a maintenance process such as cleaning or sterilization after use.

Figure 31:
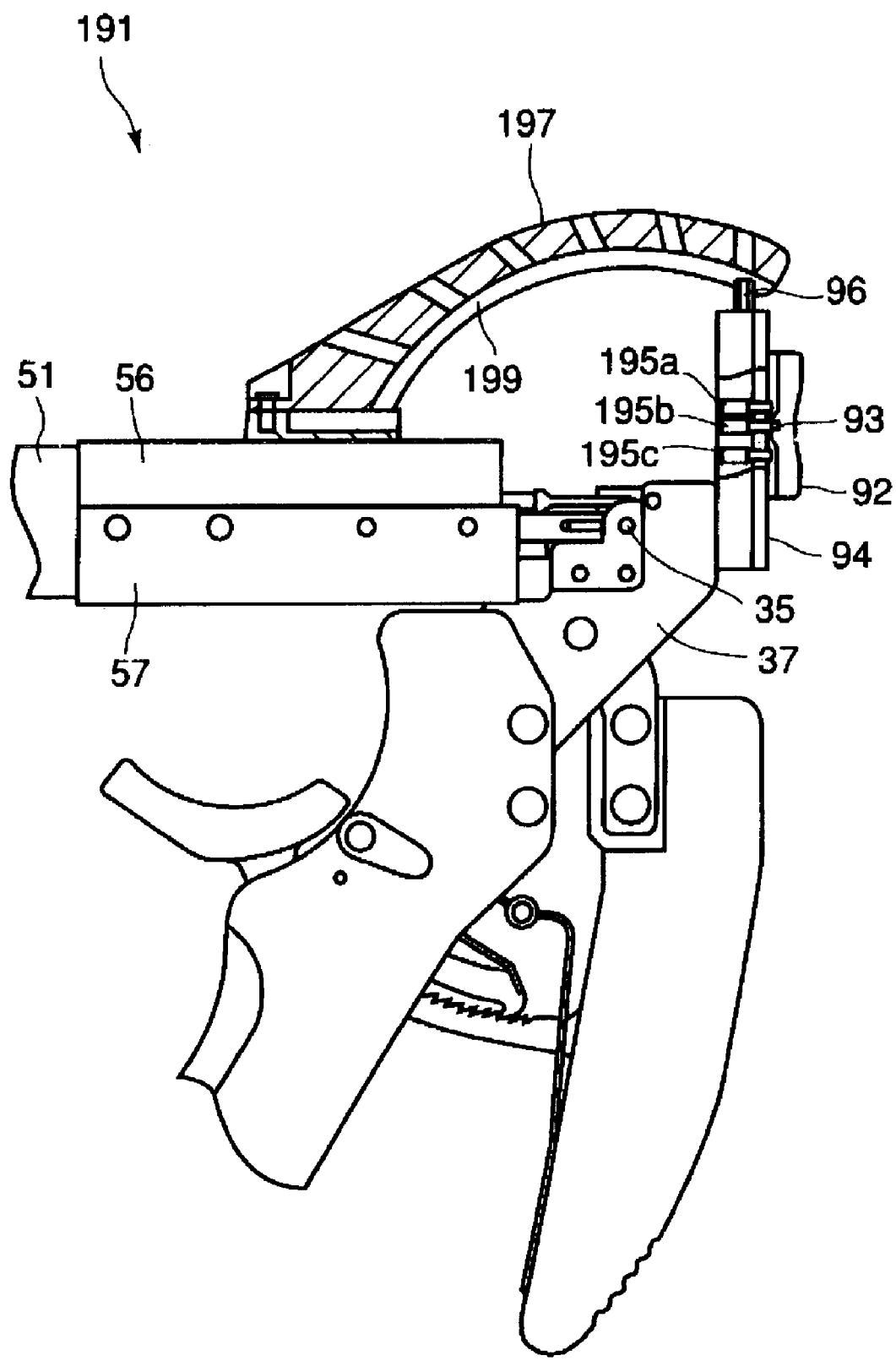
FIG. 31 is a side view showing the half opened state of the handle fixing portion of the manipulating part of the surgical therapeutic instrument shown in FIG. 29.

Referring to FIG. 31, the lever groove 93 of the slide lever 92 to which the slide key 96 is connected is engaged with the intermediate housing pin 195b, whereby the forward and backward movements of the slide key 96 are fixed. Accordingly, the tip portion of the slide key 96 is disengaged from the key accommodating portions 198a to 198f and the key accommodating portion 98, but is accommodated in the concave groove 199 formed along the inner peripheral side wall of the key accommodating housing 197. Namely, the first handle 37 is in a half opened state where its rightward and leftward turns are restricted but its upward and downward turns are not restricted. This fixed state can be used in a case such as the case where part of the degree of turning freedom of the therapeutic part 3 is not needed during an actual surgical manipulation.

Figure 32:
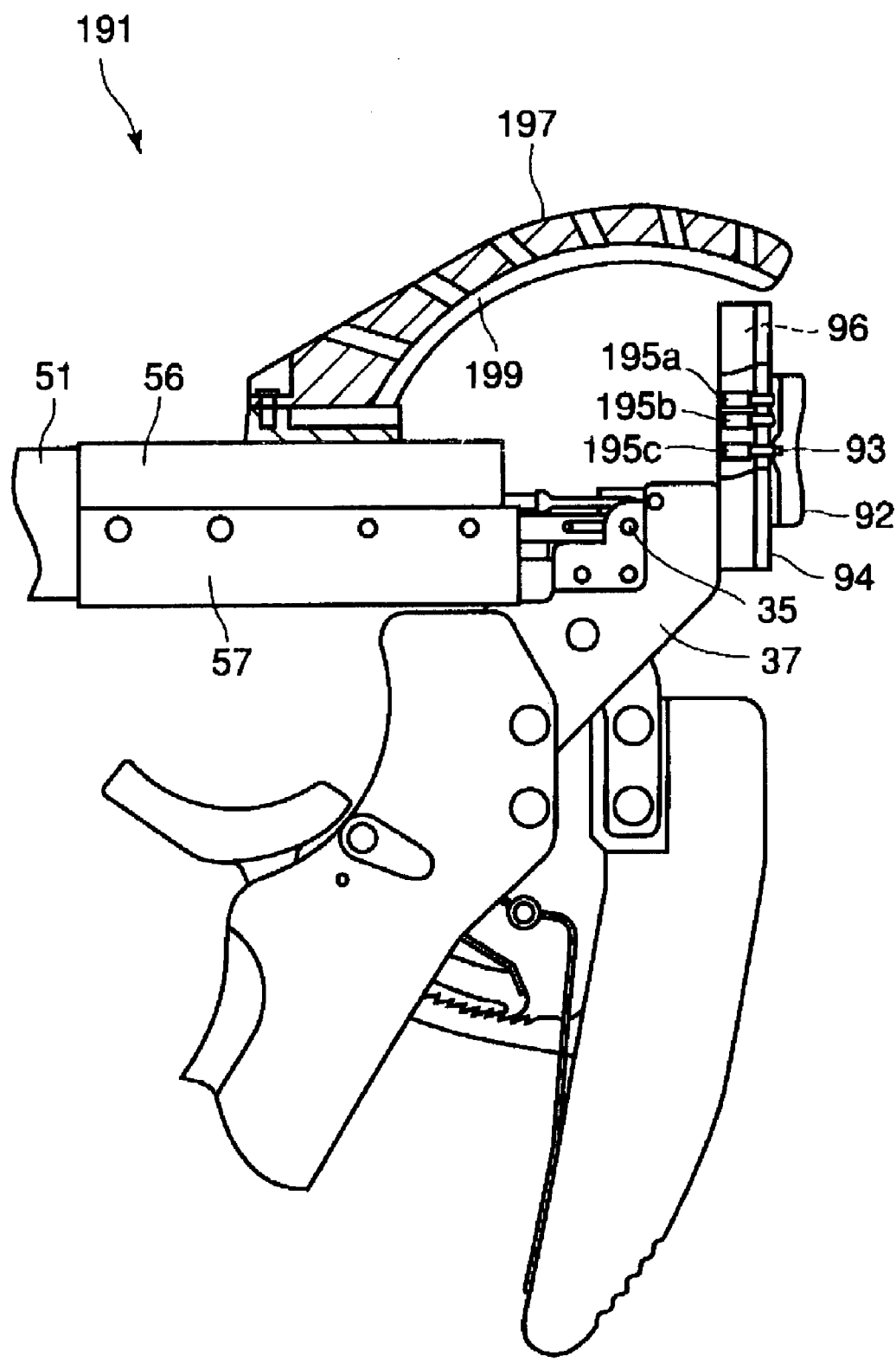
FIG. 32 is a side view showing the fully opened state of the handle fixing portion of the manipulating part of the surgical therapeutic instrument shown in FIG. 29.

Referring to FIG. 32, the lever groove 93 of the slide lever 92 to which the slide key 96 is connected is engaged with the housing pin 195c on the proximal side, whereby the forward and backward movements of the slide key 96 are fixed. Accordingly, the tip portion of the slide key 96 is disengaged not only from the key accommodating portions 198a to 198f and the key accommodating portion 98, but also is completely disengaged from the concave groove 199 formed along the inner peripheral side wall of the key accommodating housing 197. Namely, the first handle 37 is in a fully opened state where the upward, downward, rightward and leftward turns are not restricted. This state can be used in the case where the original degree of turning freedom of the therapeutic part 3 is needed during an actual surgical manipulation.

As described above, according to the sixth embodiment, the turning handles 37 and 39 can be fixed, half opened and fully opened by a comparatively simple manipulation, whereby it is possible to realize a further improvement in manipulability in actual use.

A seventh embodiment of the invention will be described below with reference to FIGS. 33 to 42. The seventh embodiment relates to a modification of each of the first handle 37 and second handle 39 of the first embodiment. Incidentally, in the following description of the seventh embodiment, the same reference numerals are used to denote constituent parts common to the first embodiment, and the description of the same constituent parts is omitted.

Figure 33:
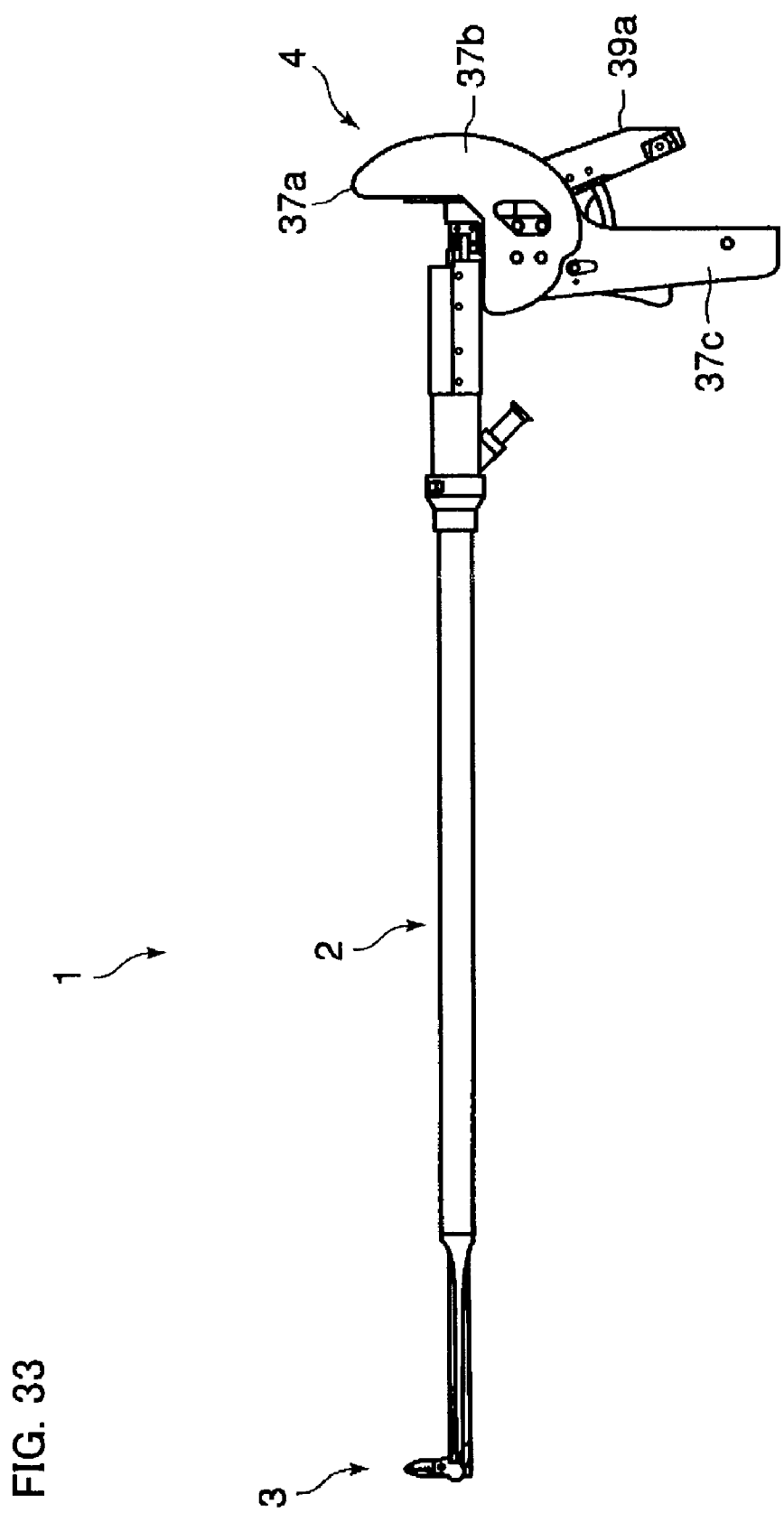
FIG. 33 is a perspective view showing the entire construction of the surgical therapeutic instrument according to a seventh embodiment of the invention.
Figure 34:
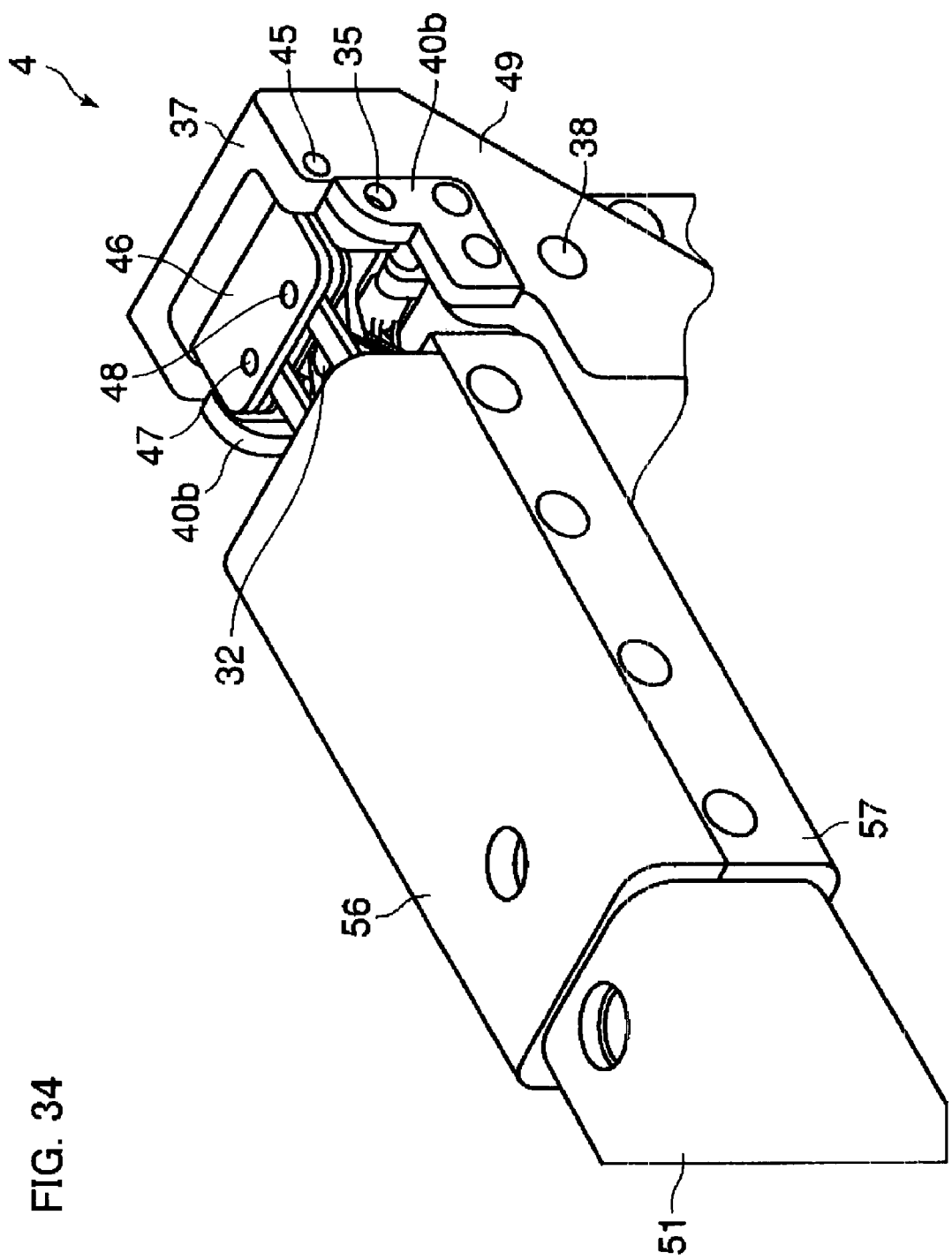
FIG. 34 is a perspective view (viewed from above) showing the manipulating part of the surgical therapeutic instrument of FIG. 33 with grips of the manipulating part removed.
Figure 35:
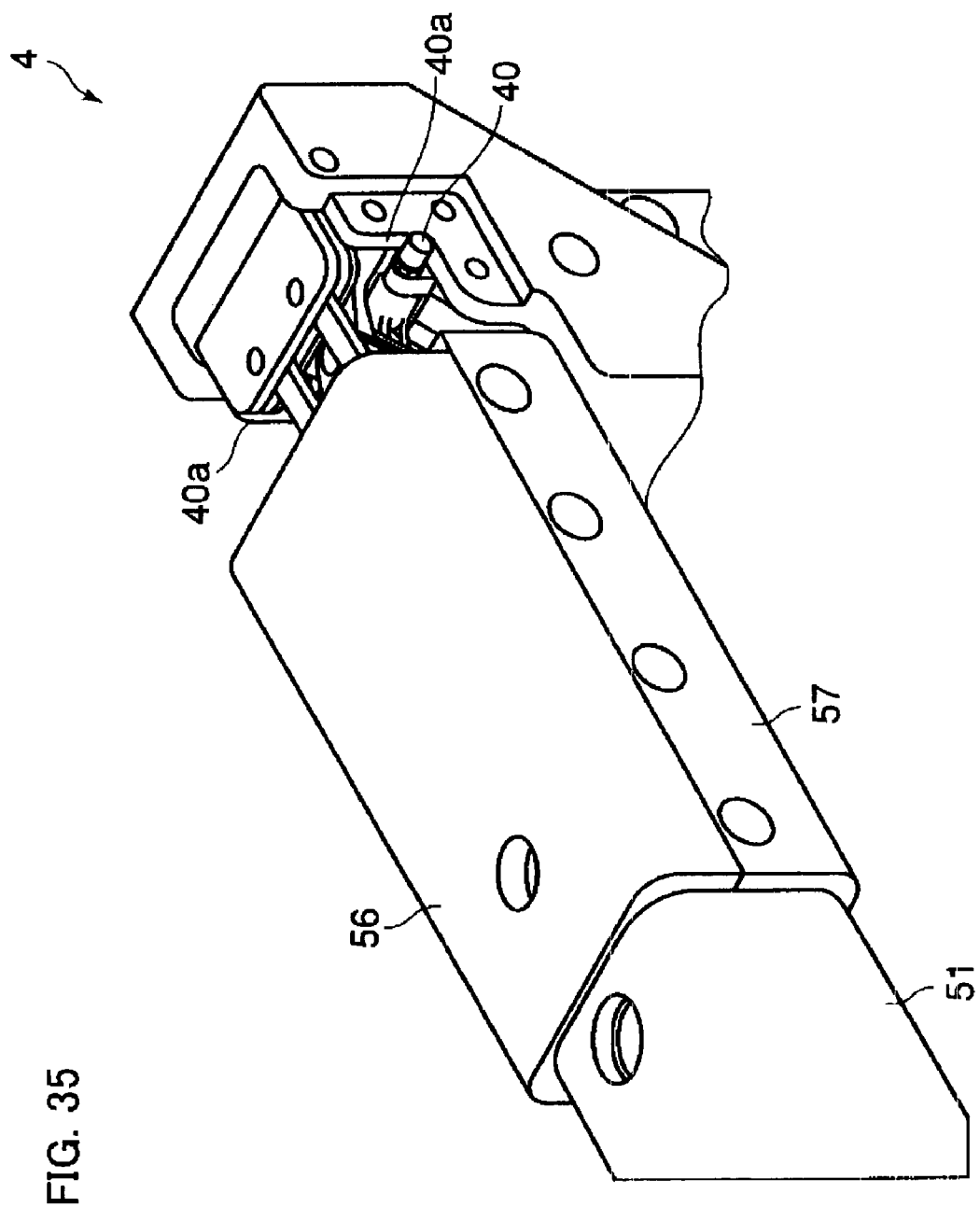
FIG. 35 is a perspective view (viewed from above) showing the manipulating part of the surgical therapeutic instrument of FIG. 33 with the grips and a handle cover of the manipulating part partly removed.
Figure 36:
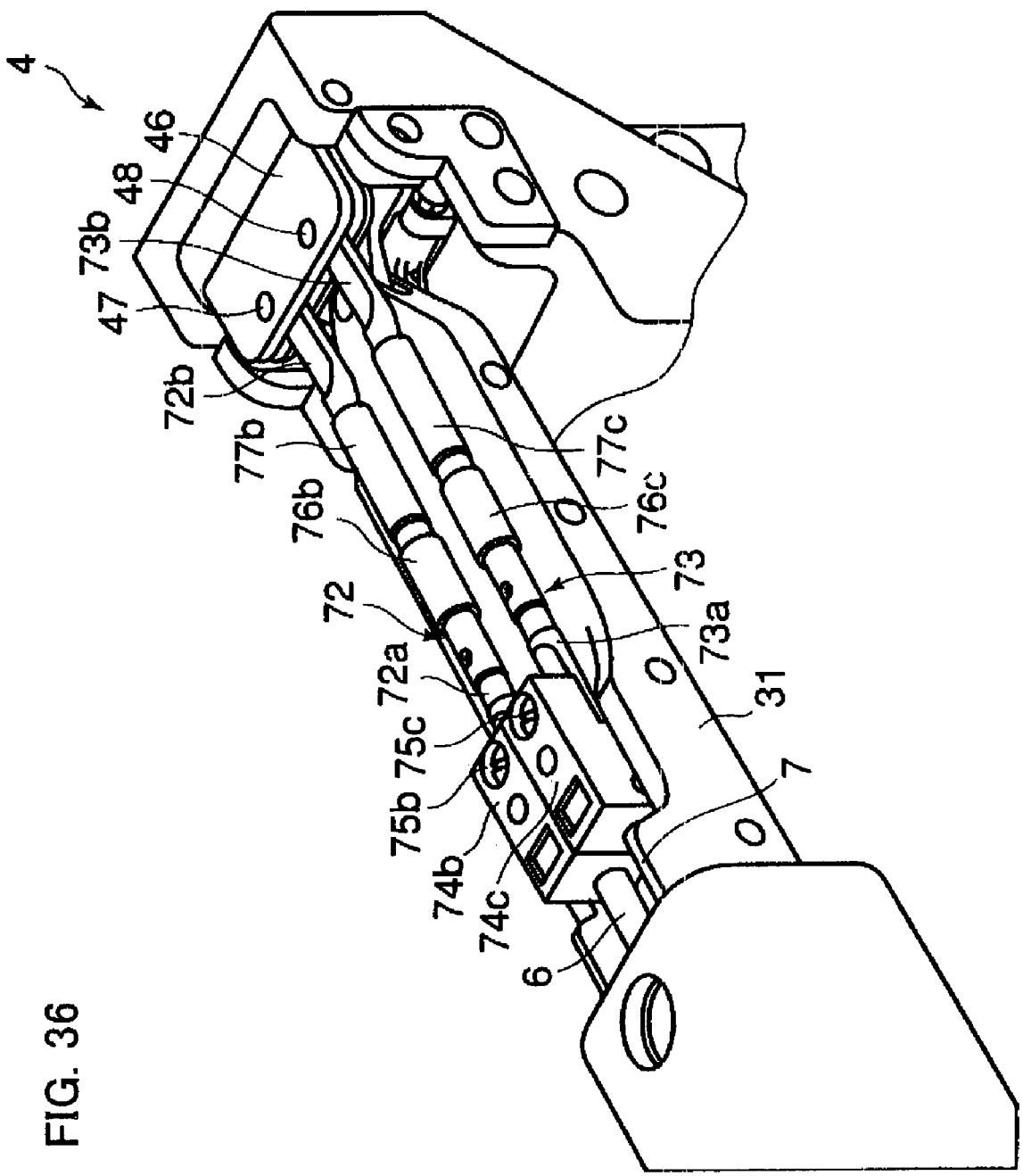
FIG. 36 is a perspective view (viewed from above) showing the manipulating part of the surgical therapeutic instrument of FIG. 33 with the grips and a guard of the manipulating part removed.
Figure 37:
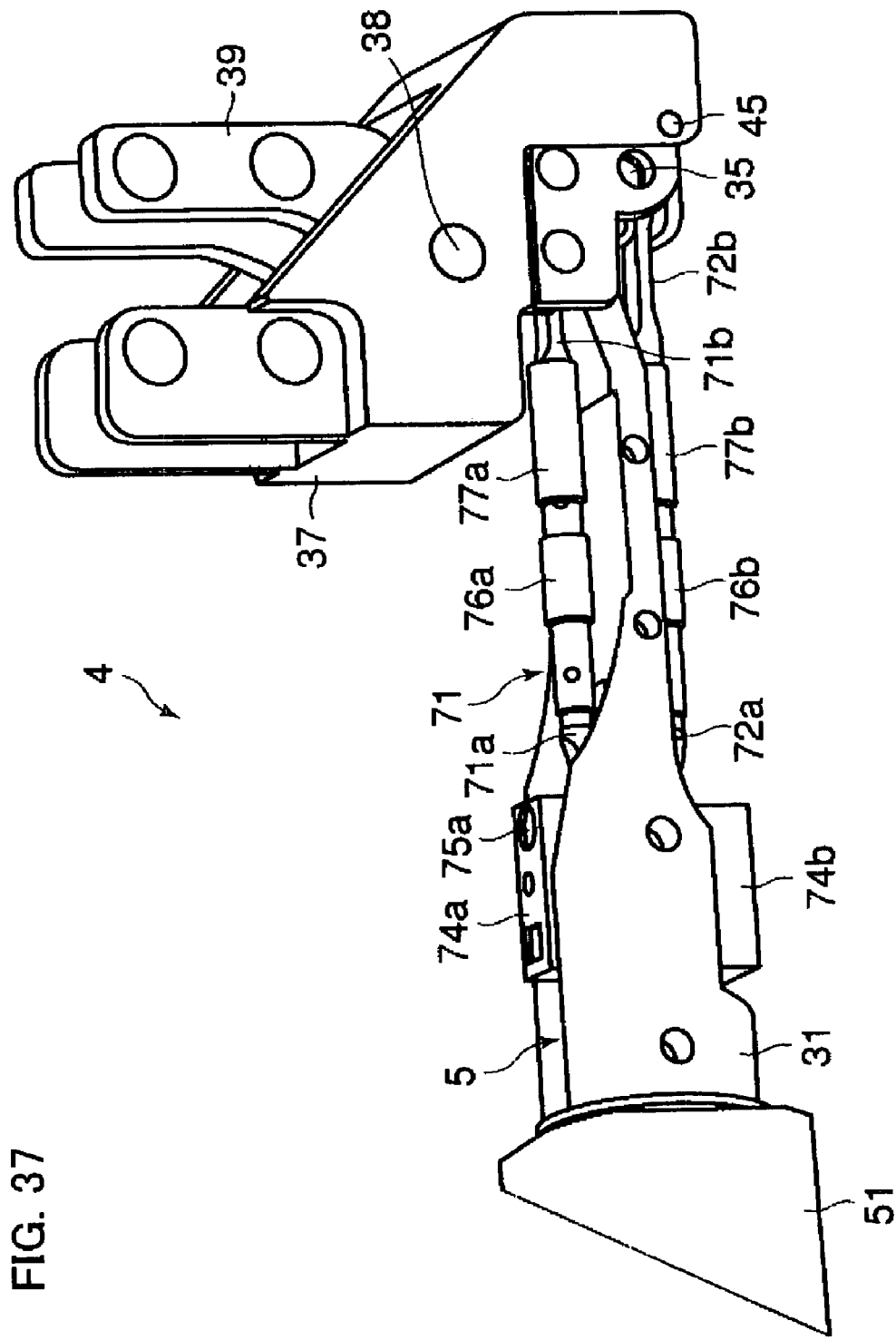
FIG. 37 is a perspective view (viewed from below) showing the manipulating part of the surgical therapeutic instrument of FIG. 33 with the grips and the guard of the manipulating part removed.

FIG. 33 is a side view showing the entire surgical therapeutic instrument according to the seventh embodiment. As compared with the first embodiment, the forms of the first handle 37 and the second handle 39 are particularly different. In addition, in the seventh embodiment, the handle fixing mechanism is not disposed at the same position as that of the first embodiment. FIGS. 34 to 37 are explanatory views of the manipulating part 4, and FIGS. 34, 35, 36 and 37 correspond to FIGS. 5, 6, 7 and 8 of the first embodiment. As is apparent from a comparison between FIGS. 34 to 37 and FIGS. 5 to 8, both embodiments do not greatly differ in the structure of the manipulating part 4 except that the handle fixing mechanisms are not disposed at the same position.

Figure 38:
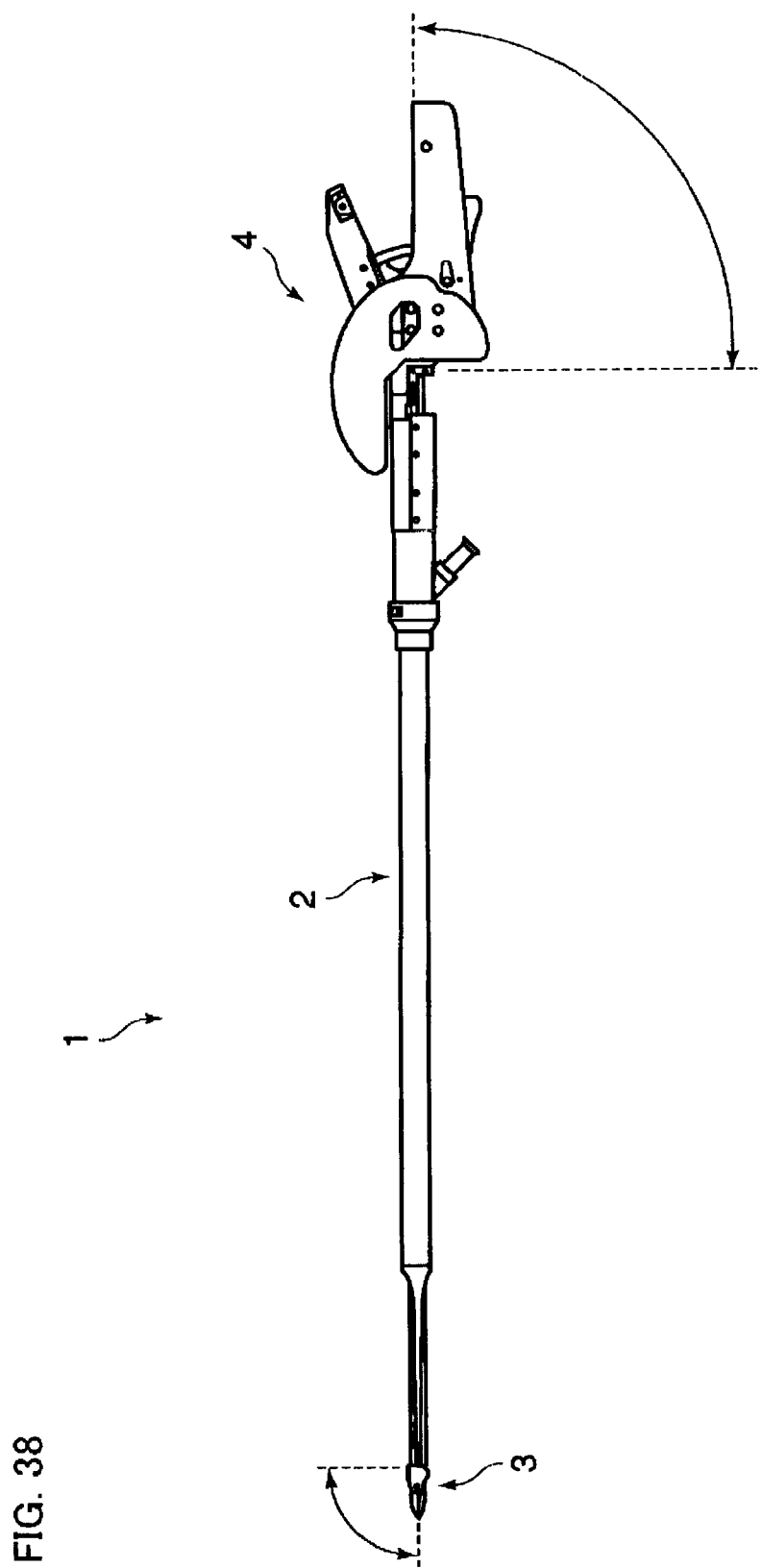
FIG. 38 is a side view of the surgical therapeutic instrument of FIG. 33 in which the therapeutic part is made horizontal.
Figure 39:
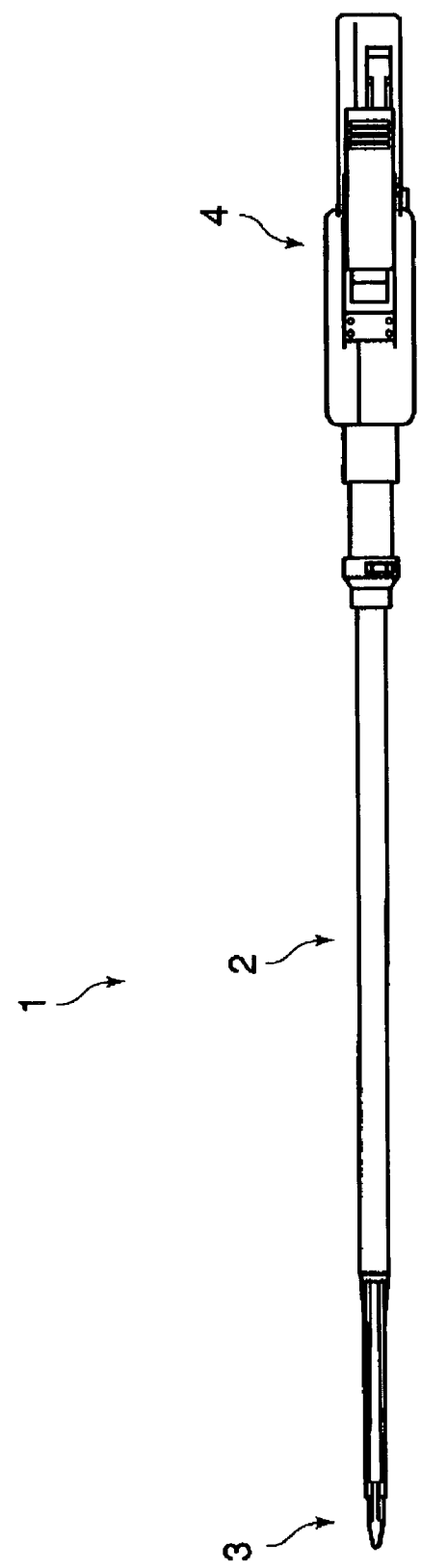
FIG. 39 is a plan view of the surgical therapeutic instrument of FIG. 33 in which the therapeutic part is made horizontal.
Figure 40:
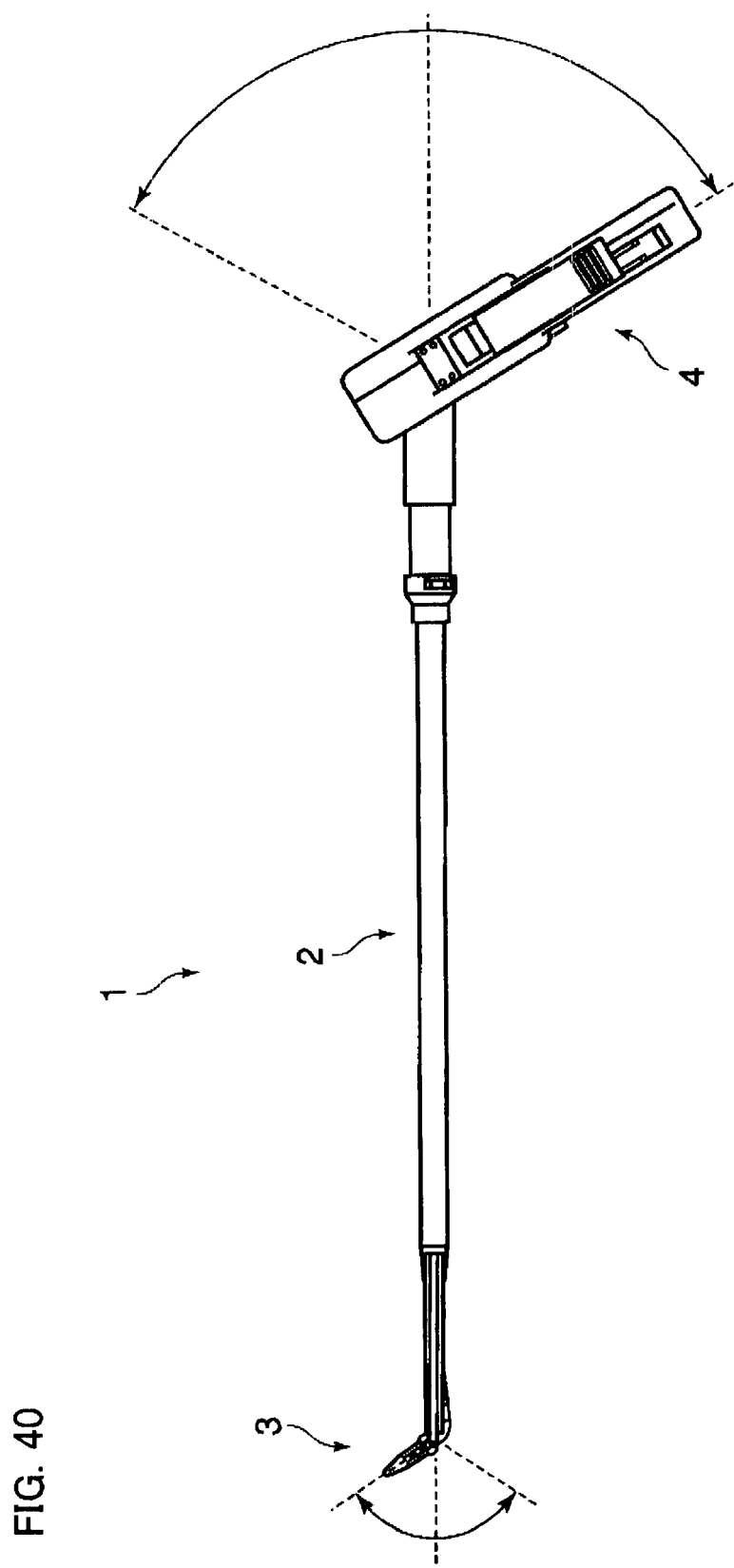
FIG. 40 is a plan view of the surgical therapeutic instrument of FIG. 33 in which the therapeutic part is made horizontal and turned to the right or left.
Figure 41:
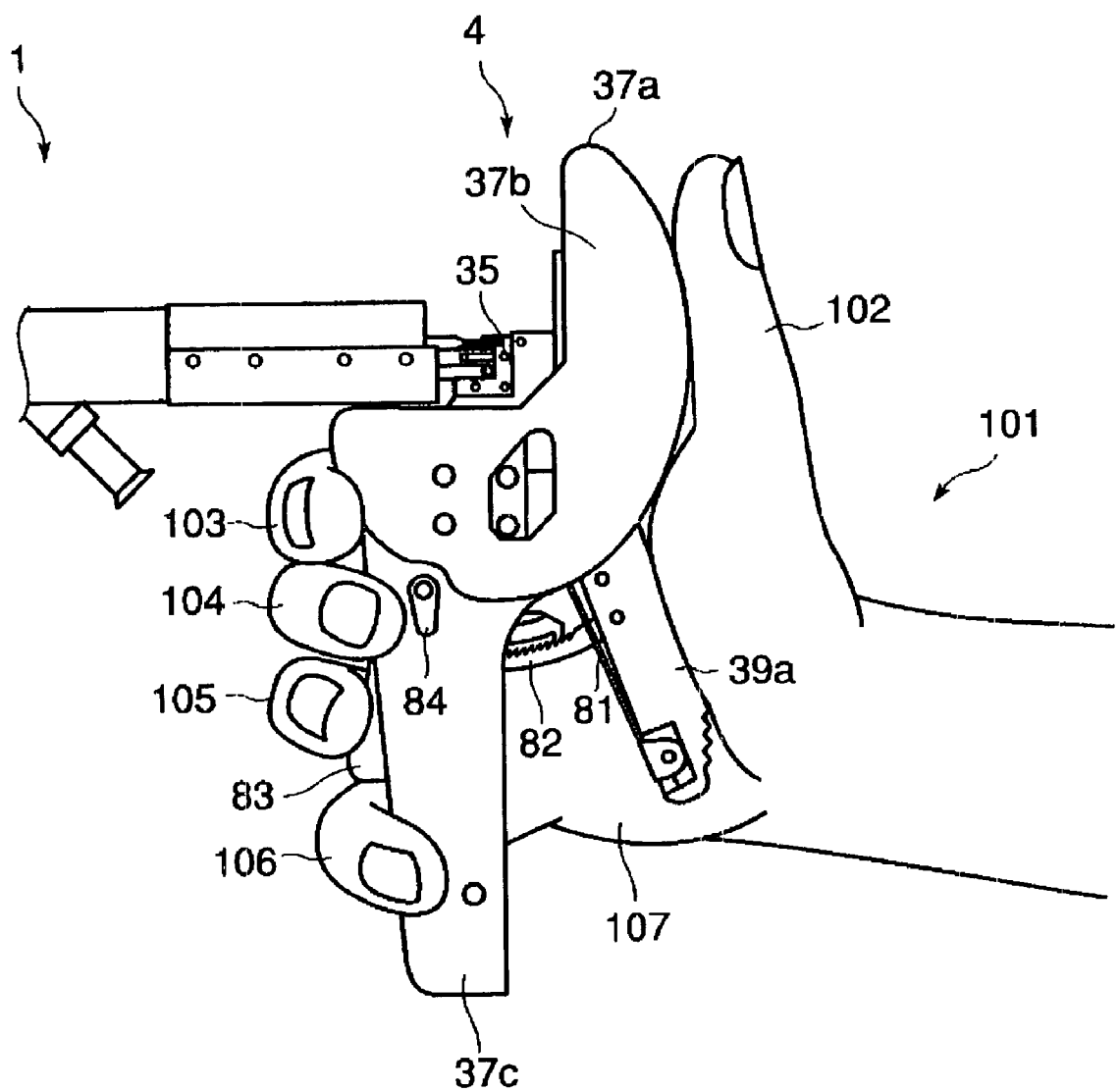
FIG. 41 is a schematic view showing the state in which the grips of the manipulating part are held from a first direction.

FIGS. 38 to 40 show the external appearance of the entire surgical therapeutic instrument according to the seventh embodiment. FIG. 41 shows the external appearance of the manipulating part 4 according to the seventh embodiment. As shown in FIG. 41, the first handle 37 has the first grip 37a. The first grip 37a has a first grip base 37b and a first grip leg 37c. The first grip base 37b has a side shape formed by an ellipse which is partly cut away, and the center of the first grip base 37b (the center of the ellipse) coincides with the third pivotal pin 35 which is a pivotal shaft for upward and downward turns. The first grip leg 37c extends beyond the side shape of the first grip base 37b. The second handle 39 has the second grip 39a.

A handle opening spring 81 and a ratchet 82 are provided between the first grip leg 37c and the second grip 39a. The handle opening spring 81 urges the second grip 39a in an opening direction with respect to the first grip leg 37c, and the ratchet 82 fixes the second grip 39a at a constant opening angle with respect to the first grip leg 37c. The first grip leg 37c has a lever 83 for arbitrarily releasing the engagement of the ratchet 82, and a ratchet disengaging lever 84 for disengaging the mechanism of the ratchet 82 to keep the ratchet mechanism constantly inactive.

Figure 42:
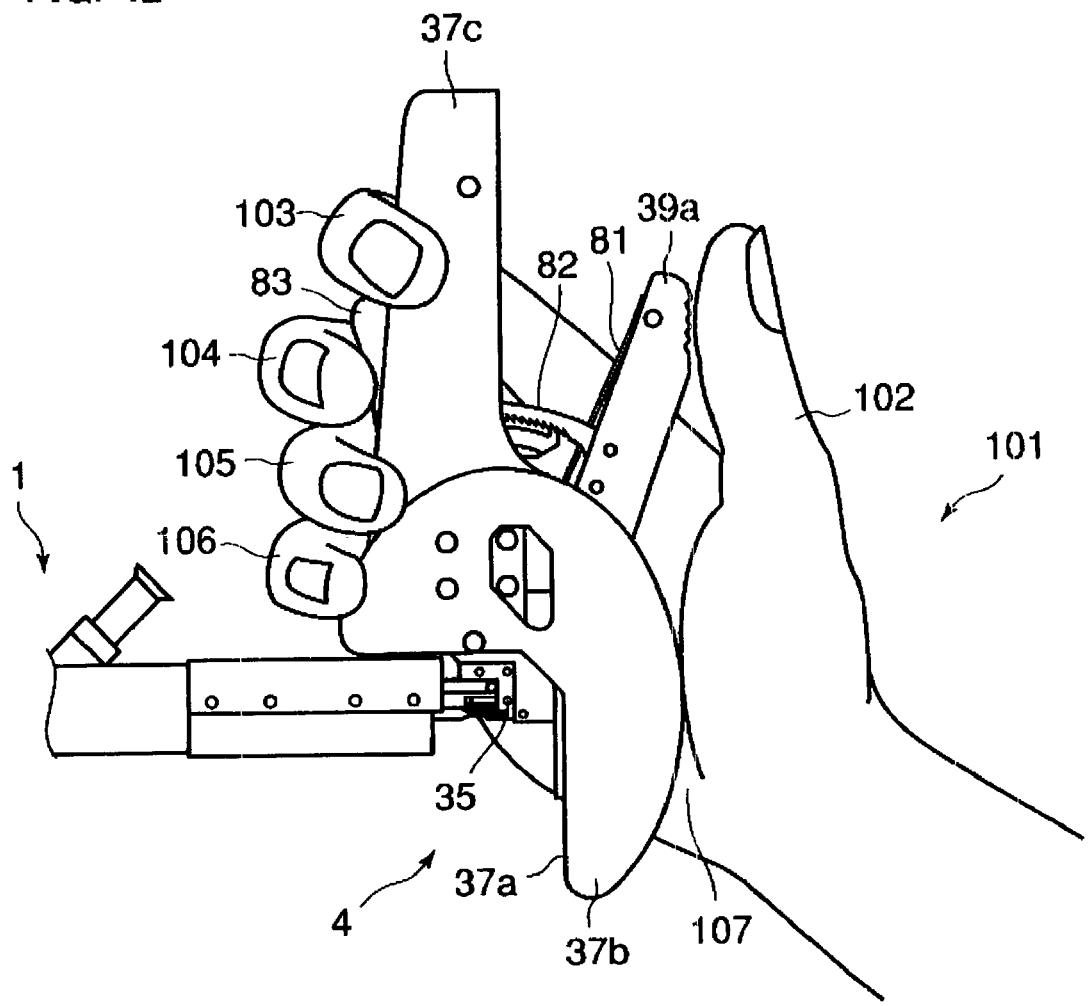
FIG. 42 is a schematic view showing the state in which the grips of the manipulating part are held from a second direction.

In actual manipulation, as shown in FIGS. 41 and 42, the operator manipulates the first and second handles 37 and 39 to activate the therapeutic part 3, by holding the first grip 37a and the second grip 39a connected to the first handle 37 and the second handle 39, for example in a right hand 101.

This manipulation will be described below with reference to FIGS. 41 and 42.

Referring to FIG. 41 which shows the state in which the first and second grips 37a and 39a are held from a first direction, the first and second grips 37a and 39a are held from a peripheral side portion of the first grip base 37b to the first grip leg 37c by a first finger 103, a second finger 104, a third finger 105 and a little finger 106, and the opposite peripheral side portion of the first grip base 37b is held by a thumb 102. The second grip 39a is manipulated by a palm 107. At this time, since the first grip leg 37c and the second grip 39a extend from the second opening and closing pivotal pin 38 to a sufficient extent, a sufficient gripping force can be transmitted to the therapeutic part 3.

FIG. 42 shows the state in which the first and second grips 37a and 39a are held from a second direction directly opposite to the first direction with respect to the longitudinal central axis of the inserting part 2. As shown in FIG. 42, the first and second grips 37a and 39a are held from the peripheral side portion of the first grip base 37b to the first grip leg 37c by the little finger 106, the third finger 105, the second finger 104 and the first finger 103, and the opposite peripheral side portion of the first grip base 37b is held by the palm 107. The second grip 39a is manipulated by the thumb 102.

In addition to the above-described two directions, both side surfaces of the first grip base 37b can be held in the state of being gripped by the thumb 102 and the other four fingers. Accordingly, the operator can execute a turning manipulation far more easily in the case where the manipulation of opening and closing the second grip 39a is not needed; for example, only the manipulation of turning the therapeutic part 3 is required when the first and second therapeutic halves 12 and 14 of the therapeutic part 3 are in the state of being fixed at a desired opening/closing angle by the activation of the ratchet 82.

As described above, in the seventh embodiment, the first and second handles 37 and 39 have portions to which the palm 107 and the thumb 102 can be put (the first grip base 37b and the second grip 39a). Specifically, the first grip base 37b which forms a portion of the external shape of the manipulating part 4 forms a circular arc or an approximately circular arc. In addition, the center of the circular arc coincides with the third pivotal pin 35 which serves as a turning shaft of the manipulating part 4 with respect to the inserting part 2, i.e., a shaft on which the manipulating part 4 is turned upwardly and downwardly. Accordingly, in whatever attitude the first and second handles 37 and 39 are turned or held, the center of turning, i.e., the pivotal shafts 32 and 35 for upward, downward, rightward and leftward turns of the first and second handles 37 and 39, is located inside or approximately inside the palm 107, whereby the amount of movement of the wrist can be minimized (the turning radius of the hand that is required during the turning manipulation of the first and second handles 37 and 39). Accordingly, in actual use, it is possible to prevent a burden from being imposed on the wrist. Incidentally, for ease of gripping, it is desirable that the radius of the above-described circular arc be not greater than 100 mm.

In this manner, the external shapes of the grips for holding the first and second handles 37 and 39 are appropriately arranged with respect to the turning pivotal shafts 32 and 35, and there is provided a grip shape capable of being held in the state of being manipulable for turning, opening and closing purposes from at least two directions. Accordingly, it is possible to reduce a burden which is imposed on the wrist during turning manipulation. Therefore, it is possible to easily perform manipulation such as moving a suturing needle in an arbitrary direction, tying a suture, or gripping, peeling and cutting a living tissue.

In addition, since the operator can stably manipulate the manipulating part 4 while holding the manipulating part 4 in the palm, a force acting in the direction of the longitudinal central axis of the surgical therapeutic instrument 1 can be reliably transmitted, and the turning attitude of the therapeutic part 3 is prevented from accidentally varying owing to the transmission of the force in the direction of the longitudinal central axis (force acting in the direction of the longitudinal central axis of the surgical therapeutic instrument 1 can be accurately transmitted in all turning attitudes that the therapeutic part 3 is placed, whereby the manipulability of the surgical therapeutic instrument 1 is improved).

In addition, since the first grip leg 37c and the second grip 39a of the first and second handles 37 and 39 of the manipulating part 4 extend from the second opening and closing pivotal pin 38 to a sufficient extent, a sufficient gripping force can be transmitted to the therapeutic part 3.

An eighth embodiment of the invention will be described below with reference to FIGS. 43 and 44. The eighth embodiment relates to a modification of the first handle 37 of the seventh embodiment. Incidentally, in the following description of the eighth embodiment, the same reference numerals are used to denote constituent parts common to the seventh embodiment, and the description of the same constituent parts is omitted.

Figure 43:
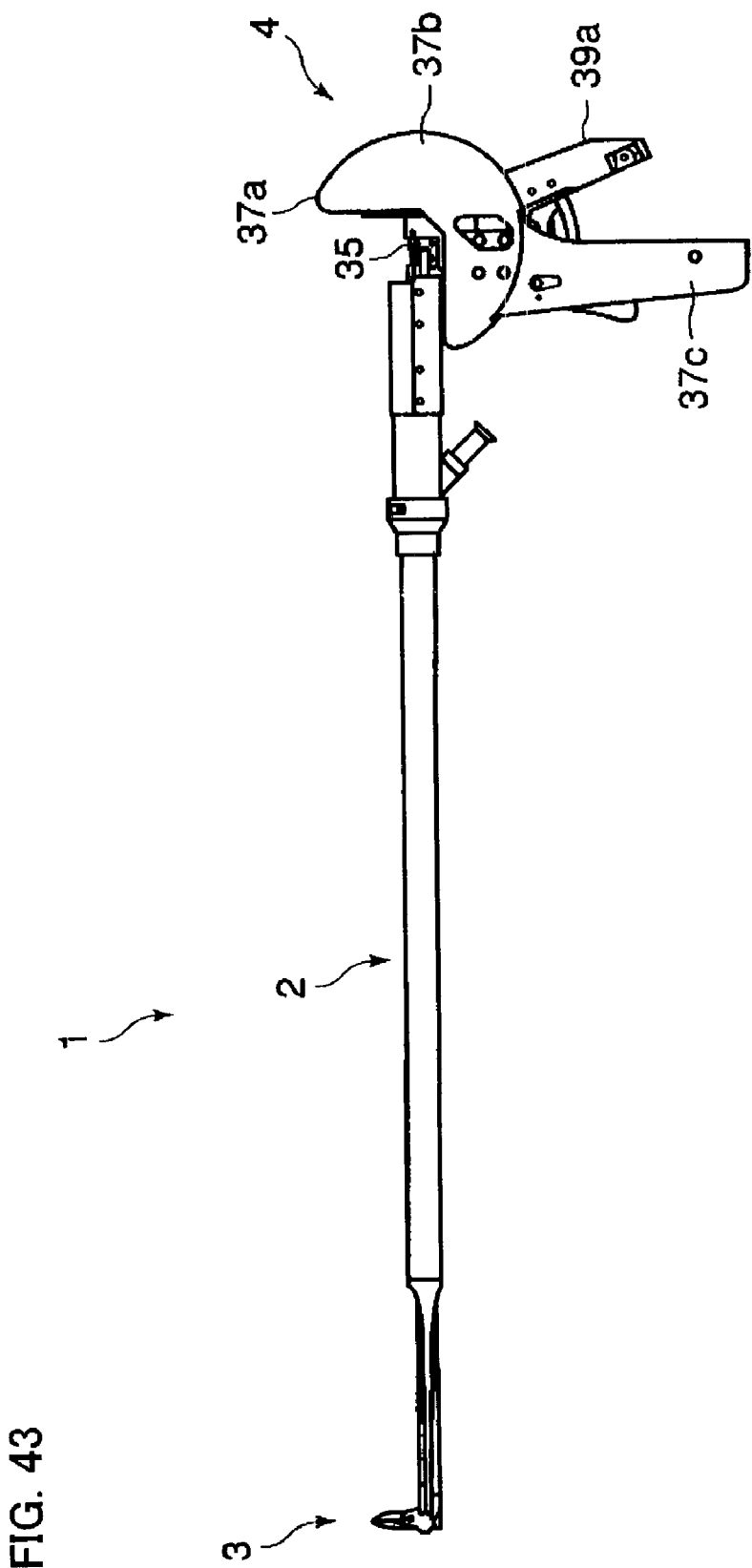
FIG. 43 is a side view of the entire construction of a surgical therapeutic instrument according to an eighth embodiment of the invention, showing the state in which the therapeutic part is turned up.
Figure 44:
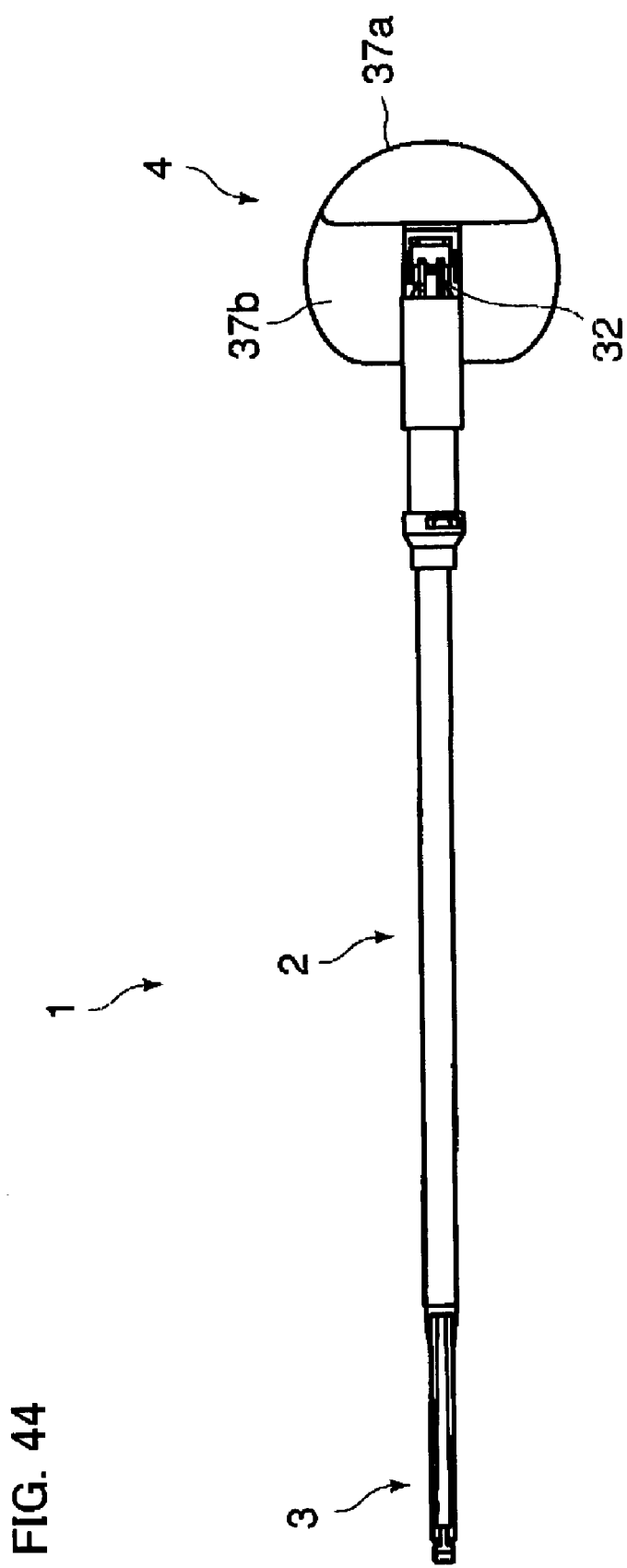
FIG. 44 is a plan view of the surgical therapeutic instrument shown in FIG. 43.

As shown in FIG. 43 in side view, the first grip base 37b of the first grip 37a has a side shape formed by a circle which is partly cut away, and the center of the first grip base 37b (the center of the circular side) coincides with the third pivotal pin 35 which is a pivotal shaft for upward and downward turns. As shown in FIG. 44 in plan view, the first grip base 37b has a plane shape formed by a circle which is partly cut away (the top surface of the first grip base 37b forms a plane), and when the therapeutic part 3 is placed in the attitude of being turned up, the center of the first grip base 37b (the center of the circular top surface) coincides with the pivotal shaft 32 which is a pivotal shaft for rightward and leftward turns. Incidentally, the other constructions are the same as those of the first embodiment. As described above, the first grip base 37b has an external shape a portion of which adopts a portion of a sphere.

According to this construction, the operator can hold the surgical therapeutic instrument 1 in a state equivalent to that in the first embodiment, and in addition, it is possible to improve the degree of holding freedom with which the first grip base 37b is held in the state of being gripped with the thumb 102 and the other four fingers.

As described above, according to the eighth embodiment, since it is possible to easily execute the turning motion of the therapeutic part 3, it is possible to improve the manipulability of the surgical therapeutic instrument.

A ninth embodiment of the invention will be described below with reference to FIG. 45. The ninth embodiment relates to another modification of the first handle 37 of each of the seventh and eighth embodiments. Incidentally, in the following description of the ninth embodiment, the same reference numerals are used to denote constituent parts common to the seventh and eighth embodiments, and the description of the same constituent parts is omitted.

Figure 45:
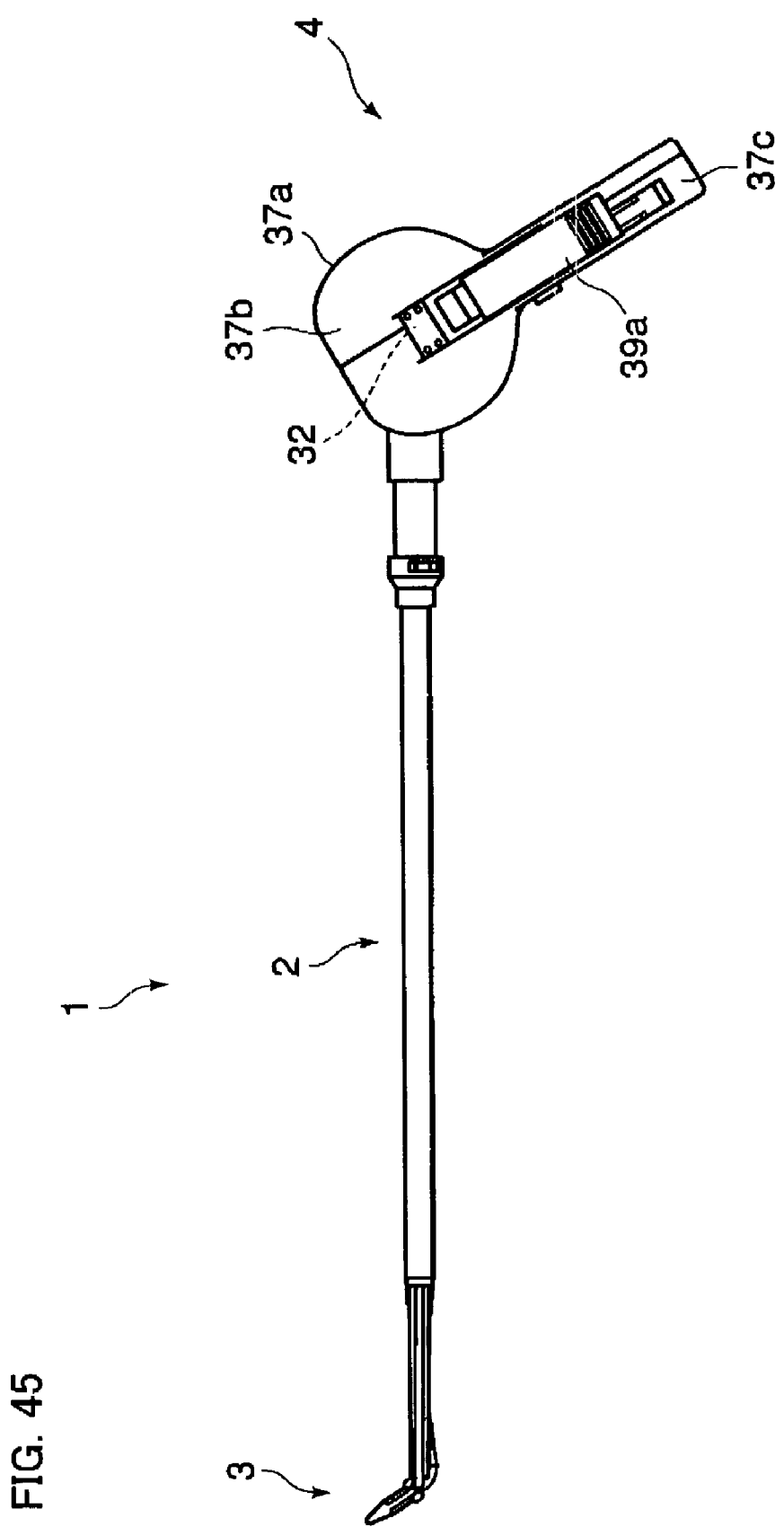
FIG. 45 is a side view of the entire construction of a surgical therapeutic instrument according to a ninth embodiment of the invention, showing the state in which the therapeutic part is made horizontal and turned to the right or left.

As shown in FIG. 45, the first grip base 37b has a plane shape formed by a circle which is partly cut away, and when the therapeutic part 3 is placed in the attitude of being made horizontal, the center of the first grip base 37b (the center of the circular top surface) coincide's with the pivotal shaft 32 which is a pivotal shaft for rightward and leftward turns. Incidentally, the other constructions are the same as those of the first embodiment.

According to this construction, the operator can hold the surgical therapeutic instrument 1 in a state equivalent to that in the eighth embodiment.

According to the ninth embodiment, since it is possible to easily execute the turning motion of the therapeutic part 3, it is possible to improve the manipulability of the surgical therapeutic instrument.

While there has been shown and described what is considered to be preferred embodiments of the invention, it will, of course, be understood that various modifications and changes in form or detail could readily be made without departing from the spirit of the invention. It is therefore intended that the invention be not limited to the exact forms described and illustrated, but should be constructed to cover all modifications that may fall within the scope of the appended claims.

What is claimed is:

1. A surgical therapeutic instrument comprising:

an inserting part to be inserted into a body;

a therapeutic part provided on a distal tip of the inserting part and having a movable portion;

a manipulating part provided on a proximal side of the inserting part for manipulating the movable portion of the therapeutic part;

a first link part connected to the therapeutic part;

a second link part provided proximal of the first link part, and connected to the manipulating part;

a first transmission shaft connected to the first link part;

a second transmission shaft connected to the second link part;

a first rotation joint for connecting the first transmission shaft and the second transmission shaft such that the first transmission shaft and the second transmission shaft can rotate relative to each other;

a position restricting member, provided on the distal side to the first rotation joint, for allowing the first transmission shaft to move in a longitudinal direction of the inserting part within the inserting part;

a third link part connected to the therapeutic pad;

a fourth link part provided proximal of the third link part, and connected to the manipulating part;

third transmission shafts including two shafts, connected to the third link part;

fourth transmission shafts including as many shafts as the third transmission shafts, connected to the fourth link part; and second rotation joints for connecting each shaft of the third transmission shafts to a corresponding shaft of the fourth transmission shafts such that each shaft of the third transmission shafts and the corresponding shaft of the fourth transmission shafts can rotate relative to each other, wherein:

the movable portion of the therapeutic part is turnable and has an openable and closable gripping mechanism, the manipulating part having an openable, closable and turnable structure, the open and close movements of the manipulating part are transmitted to the therapeutic part through the second link part, the second transmission shaft, the first rotation joint, the first transmission shaft and the first link part to make the therapeutic part open and close, and the rotation movements of the manipulating part are transmitted to the therapeutic part through the fourth link part, the fourth transmission shafts, the second rotation joints, the third transmission shafts and the third link part to make the therapeutic part rotate.

2. A surgical therapeutic instrument according to claim 1, wherein the inserting part and therapeutic part are constructed to be passed through a trocar and inserted into a living body.

3. A surgical therapeutic instrument according to claim 1, wherein the first transmission shaft and the third transmission shafts are supported in parallel with one another by the position restricting member.

4. A surgical therapeutic instrument according to claim 1, wherein the position restricting member has a guide hole elongated parallel to a longitudinal axis of the inserting part, the first transmission shaft being penetrated into the guide hole.

* * * * *